(12) United States Patent
Bettenga

(10) Patent No.: US 9,827,112 B2
(45) Date of Patent: Nov. 28, 2017

(54) SURGICAL ALIGNMENT USING REFERENCES

(71) Applicant: Smith & Nephew, Inc., Memphis, TN (US)

(72) Inventor: Mason James Bettenga, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/922,370

(22) Filed: Oct. 26, 2015

(65) Prior Publication Data

US 2016/0038307 A1 Feb. 11, 2016

Related U.S. Application Data

(62) Division of application No. 13/495,693, filed on Jun. 13, 2012, now Pat. No. 9,168,153.

(Continued)

(51) Int. Cl.
*A61F 2/46* (2006.01)
*A61B 19/00* (2006.01)
(Continued)

(52) U.S. Cl.
CPC .............. *A61F 2/46* (2013.01); *A61B 19/46* (2013.01); *A61B 34/20* (2016.02);
(Continued)

(58) Field of Classification Search
CPC ....... A61F 2/4607; A61F 2/4609; A61B 34/20
See application file for complete search history.

(56) References Cited

U.S. PATENT DOCUMENTS 3,219,969 A 11/1965 Snavely
4,353,110 A 10/1982 Ellis
(Continued)

FOREIGN PATENT DOCUMENTS

CA 2571508 1/2006
CN 2698283 Y 5/2005
(Continued)

OTHER PUBLICATIONS

International Preliminary Report on Patentability for International Application No. PCT/US2011/040042, dated Dec. 27, 2012.
(Continued)

*Primary Examiner* — David Bates
*Assistant Examiner* — Olivia C Chang
(74) *Attorney, Agent, or Firm* — Fish & Richardson P.C.

(57) ABSTRACT

Methods, systems, and apparatus, including computer-readable storage media, for surgical alignment using references. In one general aspect, a method includes coupling a guide to a joint, the guide defining an axis and having an outer contour formed to substantially conform to a portion of the joint. The first reference is attached at a fixed position relative to the joint. A positioning system is used to determine a position of the axis relative to the first reference, where the position of the axis is determined based upon the position of the guide while the guide is coupled to the joint. The guide is removed from the joint, and after the guide is removed from the joint, an instrument is positioned relative to the axis based on a position of a second reference relative to the first reference.

19 Claims, 44 Drawing Sheets

Related U.S. Application Data

(60) Provisional application No. 61/497,604, filed on Jun. 16, 2011, provisional application No. 61/497,601, filed on Jun. 16, 2011.

(51) Int. Cl.
  *A61B 34/20* (2016.01)
  *A61F 2/32* (2006.01)
  *A61B 90/00* (2016.01)

(52) U.S. Cl.
  CPC . *A61B 2034/2051* (2016.02); *A61B 2090/065* (2016.02); *A61F 2/32* (2013.01); *A61F 2/4607* (2013.01); *A61F 2/4609* (2013.01); *A61F 2002/4632* (2013.01)

(56) References Cited

U.S. PATENT DOCUMENTS

| | | |
|---|---|---|
| 4,528,980 A | 7/1985 | Kenna |
| 4,532,599 A | 7/1985 | Smith |
| 4,621,628 A | 11/1986 | Brudermann |
| 4,633,862 A | 1/1987 | Petersen |
| D297,047 S | 8/1988 | Hon et al. |
| 4,794,930 A | 1/1989 | Machida et al. |
| 4,803,976 A | 2/1989 | Frigg et al. |
| 5,049,151 A | 9/1991 | Durham et al. |
| 5,127,913 A | 7/1992 | Thomas |
| 5,129,908 A | 7/1992 | Petersen |
| 5,217,009 A | 6/1993 | Kronberg |
| 5,234,433 A | 8/1993 | Bert et al. |
| 5,251,127 A | 10/1993 | Raab |
| 5,281,224 A | 1/1994 | Faccioli et al. |
| 5,299,893 A | 4/1994 | Salyer et al. |
| 5,320,529 A | 6/1994 | Pompa |
| 5,320,625 A | 6/1994 | Bertin |
| 5,361,766 A | 11/1994 | Nichols et al. |
| 5,380,332 A | 1/1995 | Ferrante |
| 5,383,917 A | 1/1995 | Desai et al. |
| 5,411,503 A | 5/1995 | Hollstien et al. |
| 5,417,688 A | 5/1995 | Elstrom et al. |
| 5,425,368 A | 6/1995 | Brandt |
| 5,433,720 A | 7/1995 | Faccioli et al. |
| 5,514,145 A | 5/1996 | Durham et al. |
| 5,575,793 A | 11/1996 | Carls et al. |
| 5,580,156 A | 12/1996 | Suzuki et al. |
| 5,584,838 A | 12/1996 | Rona et al. |
| 5,585,783 A | 12/1996 | Hall |
| 5,682,886 A | 11/1997 | Delp |
| 5,709,689 A | 1/1998 | Ferrante et al. |
| 5,798,924 A | 8/1998 | Eufinger et al. |
| 5,951,605 A | 9/1999 | Dennis et al. |
| 5,957,836 A | 9/1999 | Johnson |
| 5,957,934 A | 9/1999 | Rapoport |
| 6,009,878 A | 1/2000 | Weijand et al. |
| 6,036,696 A | 3/2000 | Lambrecht et al. |
| 6,039,742 A | 3/2000 | Krettek et al. |
| 6,074,394 A | 6/2000 | Krause |
| 6,081,741 A | 6/2000 | Hollis |
| 6,106,528 A | 8/2000 | Durham et al. |
| 6,157,853 A | 12/2000 | Blume et al. |
| 6,162,228 A | 12/2000 | Durham |
| 6,174,335 B1 | 1/2001 | Varieur et al. |
| 6,205,411 B1 | 3/2001 | DiGola et al. |
| 6,212,419 B1 | 4/2001 | Blume et al. |
| 6,233,490 B1 | 5/2001 | Kasevich |
| 6,267,770 B1 | 7/2001 | Truwit |
| 6,304,091 B1 | 10/2001 | Shahoian et al. |
| 6,311,082 B1 | 10/2001 | Creighton et al. |
| 6,327,491 B1 | 12/2001 | Franklin et al. |
| 6,423,077 B2 | 7/2002 | Carol et al. |
| 6,474,341 B1 | 11/2002 | Hunter et al. |
| 6,503,249 B1 | 1/2003 | Krause |
| 6,529,762 B1 | 3/2003 | Ladbeck |
| 6,575,973 B1 | 6/2003 | Shekalim |
| 6,636,757 B1 | 10/2003 | Jascob et al. |
| 6,675,491 B2 | 1/2004 | Sasaki et al. |
| 6,694,168 B2 | 2/2004 | Traxel et al. |
| 6,718,194 B2 | 4/2004 | Kienzle |
| 6,747,253 B1 | 6/2004 | Firth et al. |
| 6,768,486 B1 | 7/2004 | Szabo et al. |
| 6,807,446 B2 | 10/2004 | Fenn et al. |
| 6,890,332 B2 | 5/2005 | Truckai et al. |
| 6,991,655 B2 | 1/2006 | Iverson |
| 7,001,346 B2 | 2/2006 | White |
| 7,029,478 B2 | 4/2006 | Hollstien et al. |
| 7,060,075 B2 | 6/2006 | Govari et al. |
| D528,211 S | 9/2006 | Solar et al. |
| 7,130,676 B2 | 10/2006 | Barrick |
| 7,152,608 B2 | 12/2006 | Hunter et al. |
| 7,217,276 B2 | 5/2007 | Henderson et al. |
| 7,253,611 B2 | 8/2007 | Ma |
| 7,294,133 B2 | 11/2007 | Zink et al. |
| 7,295,184 B2 | 11/2007 | Suprun et al. |
| 7,358,481 B2 | 4/2008 | Yeoh et al. |
| 7,427,200 B2 | 9/2008 | Noble et al. |
| 7,477,926 B2 | 1/2009 | McCombs |
| 7,532,997 B2 | 5/2009 | Li et al. |
| 7,534,263 B2 | 5/2009 | Burdulis et al. |
| 7,542,791 B2 | 6/2009 | Mire et al. |
| 7,549,960 B2 | 6/2009 | Govari |
| 7,559,931 B2 | 7/2009 | Stone |
| 7,575,550 B1 | 8/2009 | Govari |
| 7,618,451 B2 | 11/2009 | Berez et al. |
| 7,634,306 B2 | 12/2009 | Sarin et al. |
| 7,686,818 B2 | 3/2010 | Simon et al. |
| 7,702,379 B2 | 4/2010 | Avinash et al. |
| 7,727,240 B1 | 6/2010 | Benton |
| 7,729,742 B2 | 6/2010 | Govari |
| 7,780,681 B2 | 8/2010 | Sarin et al. |
| 7,785,330 B2 | 8/2010 | Sherman et al. |
| 7,835,785 B2 | 11/2010 | Scully et al. |
| 7,840,254 B2 | 11/2010 | Glossop |
| 7,846,162 B2 | 12/2010 | Nelson et al. |
| 7,918,853 B2 | 4/2011 | Watanabe |
| 7,925,068 B2 | 4/2011 | Hoctor et al. |
| 7,927,338 B2 | 4/2011 | Laffargue et al. |
| 7,949,386 B2 | 5/2011 | Buly et al. |
| 7,955,280 B2 | 6/2011 | Radinsky et al. |
| 8,007,448 B2 | 8/2011 | Moctezuma de La Barrera |
| 8,057,479 B2 | 11/2011 | Stone |
| 8,066,706 B2 | 11/2011 | Schlienger et al. |
| 8,167,823 B2 | 5/2012 | Nycz et al. |
| 8,176,922 B2 | 5/2012 | Sherman et al. |
| 8,197,494 B2 | 6/2012 | Jaggi |
| 8,211,108 B2 | 7/2012 | Matityahu |
| 8,241,296 B2 | 8/2012 | Wasielewski |
| 8,251,994 B2 | 8/2012 | McKenna et al. |
| 8,301,262 B2 | 10/2012 | Mi et al. |
| 8,337,426 B2 | 12/2012 | Nycz |
| 8,400,312 B2 | 3/2013 | Hotokebuchi et al. |
| 8,425,524 B2 | 4/2013 | Aker et al. |
| 8,623,023 B2 | 1/2014 | Ritchey et al. |
| 2001/0001120 A1 | 5/2001 | Masini |
| 2002/0032445 A1 | 3/2002 | Fujiwara |
| 2002/0052604 A1 | 5/2002 | Simon et al. |
| 2002/0055783 A1 | 5/2002 | Tallarida et al. |
| 2002/0077540 A1 | 6/2002 | Kienzle |
| 2002/0115934 A1 | 8/2002 | Tuke |
| 2002/0173792 A1 | 11/2002 | Severns et al. |
| 2002/0180760 A1 | 12/2002 | Rubbert et al. |
| 2003/0000535 A1 | 1/2003 | Galloway et al. |
| 2003/0045885 A1 | 3/2003 | Margulies et al. |
| 2003/0060890 A1 | 3/2003 | Tarabishy |
| 2003/0078587 A1 | 4/2003 | Lechot et al. |
| 2003/0105470 A1 | 6/2003 | White |
| 2003/0120150 A1 | 6/2003 | Govari |
| 2003/0135211 A1 | 7/2003 | Cho |
| 2003/0153829 A1 | 8/2003 | Sarin et al. |
| 2003/0163137 A1 | 8/2003 | Smucker et al. |
| 2003/0164172 A1 | 9/2003 | Chumas et al. |
| 2003/0208122 A1 | 11/2003 | Melkent et al. |
| 2004/0011365 A1 | 1/2004 | Govari et al. |
| 2004/0030245 A1 | 2/2004 | Noble |

(56) References Cited

U.S. PATENT DOCUMENTS

| | | |
|---|---|---|
| 2004/0034355 A1 | 2/2004 | Govari et al. |
| 2004/0097952 A1* | 5/2004 | Sarin .................. A61B 5/103 606/102 |
| 2004/0147926 A1 | 7/2004 | Iversen |
| 2004/0153079 A1 | 8/2004 | Tsougarakis et al. |
| 2004/0230199 A1 | 11/2004 | Jansen et al. |
| 2004/0243148 A1 | 12/2004 | Wasielewski |
| 2004/0254584 A1 | 12/2004 | Sarin et al. |
| 2004/0260301 A1 | 12/2004 | Lionberger et al. |
| 2005/0027301 A1 | 2/2005 | Stihl |
| 2005/0027304 A1 | 2/2005 | Leloup et al. |
| 2005/0035115 A1 | 2/2005 | Anderson et al. |
| 2005/0035116 A1 | 2/2005 | Brown et al. |
| 2005/0043726 A1 | 2/2005 | McHale et al. |
| 2005/0059885 A1 | 3/2005 | Melkent et al. |
| 2005/0070916 A1 | 3/2005 | Hollstien et al. |
| 2005/0075562 A1 | 4/2005 | Szakelyhidi et al. |
| 2005/0075632 A1 | 4/2005 | Russell et al. |
| 2005/0075649 A1 | 4/2005 | Bova et al. |
| 2005/0080335 A1 | 4/2005 | Simon et al. |
| 2005/0080427 A1 | 4/2005 | Govari et al. |
| 2005/0085714 A1 | 4/2005 | Foley et al. |
| 2005/0085715 A1 | 4/2005 | Dukesherer et al. |
| 2005/0099290 A1 | 5/2005 | Govari |
| 2005/0124988 A1 | 6/2005 | Terrill-Grisoni et al. |
| 2005/0143726 A1 | 6/2005 | Bortkiewicz |
| 2005/0148843 A1 | 7/2005 | Roose |
| 2005/0148855 A1 | 7/2005 | Kienzle |
| 2005/0149050 A1 | 7/2005 | Stifter et al. |
| 2005/0197569 A1 | 9/2005 | McCombs |
| 2005/0228270 A1 | 10/2005 | Lloyd et al. |
| 2005/0242087 A1 | 11/2005 | Anderson et al. |
| 2005/0245821 A1 | 11/2005 | Govari et al. |
| 2005/0261700 A1 | 11/2005 | Tuma et al. |
| 2006/0015031 A1 | 1/2006 | Kienzle |
| 2006/0029186 A1 | 2/2006 | De Villiers et al. |
| 2006/0052782 A1 | 3/2006 | Morgan et al. |
| 2006/0074405 A1 | 4/2006 | Malackowski et al. |
| 2006/0084867 A1 | 4/2006 | Tremblay |
| 2006/0095047 A1 | 5/2006 | de la Barrera |
| 2006/0106400 A1 | 5/2006 | Fernandez et al. |
| 2006/0122541 A1 | 6/2006 | Tuma |
| 2006/0142656 A1 | 6/2006 | Malackowski et al. |
| 2006/0142657 A1 | 6/2006 | Quaid et al. |
| 2006/0161051 A1 | 7/2006 | Terrill-Grisoni et al. |
| 2006/0184177 A1 | 8/2006 | Echeverri |
| 2006/0190011 A1 | 8/2006 | Ries |
| 2006/0264731 A1 | 11/2006 | Murphy |
| 2006/0276786 A1 | 12/2006 | Brinker |
| 2006/0282168 A1 | 12/2006 | Sherman et al. |
| 2006/0287613 A1 | 12/2006 | Amiot et al. |
| 2006/0293593 A1 | 12/2006 | Govari et al. |
| 2006/0293614 A1 | 12/2006 | Radinsky et al. |
| 2007/0093709 A1 | 4/2007 | Abernathie |
| 2007/0106299 A1 | 5/2007 | Manspeizer |
| 2007/0123912 A1 | 5/2007 | Carson et al. |
| 2007/0129629 A1 | 6/2007 | Beauregard et al. |
| 2007/0162018 A1 | 7/2007 | Jensen et al. |
| 2007/0167744 A1 | 7/2007 | Beauregard et al. |
| 2007/0191827 A1 | 8/2007 | Lischinsky et al. |
| 2007/0198022 A1 | 8/2007 | Lang et al. |
| 2007/0208251 A1 | 9/2007 | Anderson et al. |
| 2007/0219639 A1 | 9/2007 | Otto et al. |
| 2007/0225595 A1 | 9/2007 | Malackowski et al. |
| 2007/0249967 A1 | 10/2007 | Buly et al. |
| 2007/0255132 A1 | 11/2007 | Shalgi et al. |
| 2007/0270680 A1 | 11/2007 | Sheffer et al. |
| 2007/0276224 A1 | 11/2007 | Lang et al. |
| 2007/0276370 A1 | 11/2007 | Altarac et al. |
| 2007/0282440 A1 | 12/2007 | Visentin |
| 2008/0009952 A1 | 1/2008 | Hodge |
| 2008/0015551 A1 | 1/2008 | Feine et al. |
| 2008/0021309 A1 | 1/2008 | Amiot et al. |
| 2008/0039857 A1 | 2/2008 | Giersch et al. |
| 2008/0051910 A1 | 2/2008 | Kammerzell et al. |
| 2008/0071142 A1 | 3/2008 | Gattani et al. |
| 2008/0086145 A1 | 4/2008 | Sherman et al. |
| 2008/0097450 A1 | 4/2008 | Brown et al. |
| 2008/0146969 A1 | 6/2008 | Kurtz |
| 2008/0154266 A1 | 6/2008 | Protopsaltis et al. |
| 2008/0154269 A1 | 6/2008 | Roger et al. |
| 2008/0171932 A1 | 7/2008 | Yan et al. |
| 2008/0188855 A1 | 8/2008 | Brown et al. |
| 2008/0221628 A1 | 9/2008 | Milbocker et al. |
| 2008/0228195 A1 | 9/2008 | von Jako et al. |
| 2008/0242953 A1 | 10/2008 | Dew et al. |
| 2008/0243127 A1 | 10/2008 | Lang et al. |
| 2008/0255560 A1 | 10/2008 | Myers et al. |
| 2008/0255584 A1* | 10/2008 | Beverland .............. A61B 5/103 606/130 |
| 2008/0269596 A1 | 10/2008 | Revie et al. |
| 2008/0281326 A1 | 11/2008 | Watanabe et al. |
| 2008/0281334 A1 | 11/2008 | Zheng et al. |
| 2008/0281426 A1 | 11/2008 | Fitz et al. |
| 2008/0312663 A1 | 12/2008 | Haimerl et al. |
| 2008/0319448 A1 | 12/2008 | Lavallee et al. |
| 2008/0319491 A1 | 12/2008 | Schoenefeld |
| 2009/0024023 A1 | 1/2009 | Welches et al. |
| 2009/0054910 A1 | 2/2009 | Zheng et al. |
| 2009/0088753 A1 | 4/2009 | Aram et al. |
| 2009/0088755 A1 | 4/2009 | Aker et al. |
| 2009/0088756 A1 | 4/2009 | Anderson |
| 2009/0088763 A1 | 4/2009 | Aram et al. |
| 2009/0093816 A1 | 4/2009 | Roose et al. |
| 2009/0099404 A1 | 4/2009 | Kraus et al. |
| 2009/0099570 A1 | 4/2009 | Paradis et al. |
| 2009/0099665 A1 | 4/2009 | Taylor et al. |
| 2009/0125117 A1 | 5/2009 | Paradis et al. |
| 2009/0138019 A1 | 5/2009 | Wasielewski |
| 2009/0138020 A1 | 5/2009 | Park et al. |
| 2009/0157083 A1 | 6/2009 | Park et al. |
| 2009/0163922 A1 | 6/2009 | Meridew et al. |
| 2009/0165573 A1 | 7/2009 | Ledoux et al. |
| 2009/0171184 A1 | 7/2009 | Jenkins et al. |
| 2009/0171370 A1 | 7/2009 | Yoon et al. |
| 2009/0177080 A1 | 7/2009 | Kristan et al. |
| 2009/0227862 A1 | 9/2009 | Smith et al. |
| 2009/0227905 A1 | 9/2009 | Warkentine et al. |
| 2009/0281415 A1 | 11/2009 | Cupps et al. |
| 2009/0306665 A1 | 12/2009 | Lerner et al. |
| 2009/0306666 A1 | 12/2009 | Czartoski et al. |
| 2009/0318976 A1 | 12/2009 | Gabriel et al. |
| 2009/0326537 A1 | 12/2009 | Anderson |
| 2010/0023015 A1 | 1/2010 | Park |
| 2010/0030223 A1 | 2/2010 | Keller |
| 2010/0030231 A1 | 2/2010 | Revie et al. |
| 2010/0041985 A1 | 2/2010 | Simon et al. |
| 2010/0063508 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0076563 A1 | 3/2010 | Otto et al. |
| 2010/0100011 A1 | 4/2010 | Roche |
| 2010/0137869 A1 | 6/2010 | Borja et al. |
| 2010/0137871 A1 | 6/2010 | Borja |
| 2010/0145337 A1 | 6/2010 | Janna et al. |
| 2010/0152566 A1 | 6/2010 | Rains et al. |
| 2010/0152573 A1 | 6/2010 | Ritchey et al. |
| 2010/0185202 A1 | 7/2010 | Lester et al. |
| 2010/0211177 A1 | 8/2010 | Abdou |
| 2010/0249657 A1 | 9/2010 | Nycz et al. |
| 2010/0249796 A1 | 9/2010 | Nycz |
| 2010/0261998 A1 | 10/2010 | Stiehl |
| 2010/0274121 A1 | 10/2010 | Ritchey et al. |
| 2010/0274253 A1 | 10/2010 | Ure |
| 2010/0274256 A1 | 10/2010 | Ritchey et al. |
| 2010/0274306 A1 | 10/2010 | Pastore et al. |
| 2010/0289491 A1 | 11/2010 | Budker et al. |
| 2010/0312245 A1 | 12/2010 | Tipirneni et al. |
| 2011/0060339 A1 | 3/2011 | de Wekker |
| 2011/0082366 A1 | 4/2011 | Scully |
| 2011/0109311 A1 | 5/2011 | Walsh |
| 2011/0130765 A1 | 6/2011 | Fernandez et al. |
| 2011/0208037 A1 | 8/2011 | Rains et al. |

(56) References Cited

U.S. PATENT DOCUMENTS

| | | |
|---|---|---|
| 2011/0230886 A1 | 9/2011 | Gustilo et al. |
| 2011/0257518 A1 | 10/2011 | Buly et al. |
| 2011/0270080 A1 | 11/2011 | Crane |
| 2011/0276053 A1 | 11/2011 | Birkbeck et al. |
| 2011/0288600 A1 | 11/2011 | Ritchey et al. |
| 2011/0295108 A1 | 12/2011 | Cox |
| 2011/0295253 A1 | 12/2011 | Bonutti et al. |
| 2012/0010500 A1 | 1/2012 | Couture et al. |
| 2012/0022406 A1 | 1/2012 | Hladio et al. |
| 2012/0035468 A1 | 2/2012 | Ritchey et al. |
| 2012/0091122 A1 | 4/2012 | Ahmad et al. |
| 2012/0101361 A1 | 4/2012 | Rains et al. |
| 2012/0130279 A1 | 5/2012 | Stone |
| 2012/0136402 A1 | 5/2012 | Burroughs |
| 2012/0143047 A1 | 6/2012 | Kimura |
| 2012/0157887 A1 | 6/2012 | Fanson et al. |
| 2012/0184844 A1 | 7/2012 | Gielen |
| 2012/0209117 A1 | 8/2012 | Mozes et al. |
| 2012/0220107 A1 | 8/2012 | Fukuda et al. |
| 2012/0226094 A1 | 9/2012 | Ritchey et al. |
| 2012/0227542 A1 | 9/2012 | Koch |
| 2012/0232561 A1 | 9/2012 | Fernandez |
| 2012/0245647 A1 | 9/2012 | Kunz et al. |
| 2012/0253354 A1 | 10/2012 | Arlettaz et al. |
| 2012/0277752 A1 | 11/2012 | Wasielewski |
| 2012/0283599 A1 | 11/2012 | Borja |
| 2012/0323247 A1 | 12/2012 | Bettenga |
| 2012/0330319 A1 | 12/2012 | Birkbeck et al. |
| 2013/0046310 A1 | 2/2013 | Ranawat et al. |
| 2013/0053856 A1 | 2/2013 | Penenberg |
| 2013/0053858 A1 | 2/2013 | Penenberg |
| 2013/0053904 A1 | 2/2013 | Penenberg |
| 2013/0066323 A1 | 3/2013 | Nycz et al. |
| 2013/0131679 A1 | 5/2013 | Janna et al. |
| 2013/0218007 A1 | 8/2013 | Petteys et al. |
| 2013/0289573 A1 | 10/2013 | Heilala et al. |

FOREIGN PATENT DOCUMENTS

| | | |
|---|---|---|
| CN | 1913844 | 2/2007 |
| CN | 201029876 | 3/2008 |
| DE | 102008023760 | 12/2009 |
| EP | 523905 | 5/1993 |
| EP | 628287 | 4/1995 |
| EP | 1391181 | 2/2004 |
| EP | 1570782 | 9/2005 |
| EP | 1382308 | 11/2005 |
| EP | 1803394 | 7/2007 |
| EP | 1570781 | 9/2009 |
| EP | 2130511 | 12/2009 |
| EP | 1563810 | 3/2010 |
| EP | 1743590 | 10/2010 |
| EP | 2294980 | 3/2012 |
| GR | 1005791 | 1/2008 |
| WO | WO9325157 | 12/1993 |
| WO | WO9400056 | 1/1994 |
| WO | WO9421209 | 9/1994 |
| WO | WO9500085 | 1/1995 |
| WO | WO9625114 | 8/1996 |
| WO | WO9713467 | 4/1997 |
| WO | WO9832387 | 7/1998 |
| WO | WO9947052 | 9/1999 |
| WO | WO0134016 | 10/2001 |
| WO | WO02062250 | 8/2002 |
| WO | WO02063236 A2 | 8/2002 |
| WO | WO03044556 | 5/2003 |
| WO | WO03073951 | 9/2003 |
| WO | WO03041611 | 12/2003 |
| WO | WO03105659 | 12/2003 |
| WO | WO2004030556 | 4/2004 |
| WO | WO2004001569 | 7/2004 |
| WO | WO2004069063 | 8/2004 |
| WO | WO2004078078 | 9/2004 |
| WO | WO2004091419 | 11/2004 |
| WO | WO2004112610 | 12/2004 |
| WO | WO2005000140 | 1/2005 |
| WO | WO2005009303 | 2/2005 |
| WO | WO2005023110 | 3/2005 |
| WO | WO2005051241 | 6/2005 |
| WO | WO2005084572 | 9/2005 |
| WO | WO2005087125 | 9/2005 |
| WO | WO2005120203 | 12/2005 |
| WO | WO2006060632 | 6/2006 |
| WO | WO2006067634 | 6/2006 |
| WO | WO2006078236 | 7/2006 |
| WO | WO2006109983 | 10/2006 |
| WO | WO2006128301 | 12/2006 |
| WO | WO2006129087 | 12/2006 |
| WO | WO2007009088 | 1/2007 |
| WO | WO2007025191 | 3/2007 |
| WO | WO2007061890 | 5/2007 |
| WO | WO2006094119 | 11/2007 |
| WO | WO2007133168 | 11/2007 |
| WO | WO2008014618 | 2/2008 |
| WO | WO2008105874 | 9/2008 |
| WO | WO2008106593 | 9/2008 |
| WO | WO2009001083 | 12/2008 |
| WO | WO2009046547 | 4/2009 |
| WO | WO2009062314 | 5/2009 |
| WO | WO2009075562 | 6/2009 |
| WO | WO2009106816 | 9/2009 |
| WO | WO2009108214 | 9/2009 |
| WO | WO2009131999 | 10/2009 |
| WO | WO2010011978 | 1/2010 |
| WO | WO2010028046 | 3/2010 |
| WO | WO2010030809 | 3/2010 |
| WO | WO2010052500 | 5/2010 |
| WO | WO2010063117 | 6/2010 |
| WO | WO2010099231 | 9/2010 |
| WO | WO2010099247 | 9/2010 |
| WO | WO2010111272 | 9/2010 |
| WO | WO2010124164 A2 | 10/2010 |
| WO | WO2010129141 | 11/2010 |
| WO | WO2010129308 | 11/2010 |
| WO | WO2011060536 | 5/2011 |
| WO | WO2011124661 | 10/2011 |
| WO | WO2012080840 | 6/2012 |
| WO | WO2012084739 | 6/2012 |
| WO | WO2012100825 | 8/2012 |
| WO | WO2013025927 | 2/2013 |
| WO | WO2013049534 | 4/2013 |

OTHER PUBLICATIONS

International Search Report and Written Opinion for International Application No. PCT/US2011/040031, dated Feb. 17, 2012.
International Preliminary Report on Patentability for International Application No. PCT/US2011/040031, dated Dec. 27, 2012.
Office Action for Chinese Application 201180039329.3, dated Oct. 10, 2014.
International Search Report and Written Opinion for International Application No. PCT/US2011/040042, dated Feb. 17, 2012.
Office Action for U.S. Appl. No. 13/158,200, dated Mar. 12, 2014.
International Search Report for International Application No. PCT/US2012/040373, dated Oct. 23, 2012.
Visionaire Patient Matched Instrumentation—A technology from Smith & Nephew Design Rationale, 7 pages (2008).
Office Action for U.S. Appl. No. 12/746,272, dated Jun. 18, 2013.
International Search Report for International Application No. PCT/US2011/047897, dated Mar. 27, 2012.
International Search Report for International Application No. PCT/US2011/047860, dated Mar. 19, 2012.
International Search Report for International Application No. PCT/US2011/047936, dated Mar. 26, 2012.
International Search Report for International Application No. PCT/US201/047671, dated Mar. 28, 2012.
International Search Report for International Application No. PCT/US2011/047675, dated Feb. 29, 2012.
International Search Report for International Application No. PCT/US2011/047674, dated Mar. 5, 2012.

(56) References Cited

OTHER PUBLICATIONS

International Preliminary Report on Patentability for International Application No. PCT/US2011/047674, dated Feb. 19, 2013.
International Search Report for International Application No. PCT/US2011/047670, dated Mar. 19, 2012.
International Preliminary Report on Patentability for International Application No. PCT/US2011/047670, dated Feb. 19, 2013.
International Search Report for International Application No. PCT/US2011/056380, dated May 21, 2012.
International Preliminary Report on Patentability for International Application No. PCT/US2011/056380, dated Apr. 16, 2013.
International Search Report for International Application No. PCT/US2011/085897, dated May 28, 2009.
International Preliminary Report on Patentability for International Application No. PCT/US2011/085897, dated Jun. 8, 2010.
Office Action for U.S. Appl. No. 12/770,532 dated Oct. 9, 2012.
Office Action for U.S. Appl. No. 12/770,532, dated May 23, 2013.
U.S. Office Action issued in U.S. Appl. No. 12/770,532 (McGuan, filed Apr. 29, 2010), dated Oct. 9, 2012.
Office Action for U.S. Appl. No. 13/157,991, dated Jan. 15, 2014.
Office Action for U.S. Appl. No. 13/158,200, dated Sep. 5, 2014.
"S-ROM® Noiles™ Rotating Hinge: Surgical Technique and Reference Guide," © 2002 DePuy Orthopaedics, Inc.
Extended European Search Report for European Application No. 08859728.1, dated Oct. 11, 2013.
Office Action for U.S. Appl. No. 12/758,747, dated Aug. 11, 2014.
Notice of Reasons for Rejection for Japanese Application No. 2012-508518 dated Dec. 10, 2013.
Office Action in Russian Application No. 2011146914, dated Dec. 16, 2013.
"Guiding Star with the LIDIS module," Ekliptik, 2007.
Ekliptik, LIDIS module, brochure, 2010.
Brochure for GE Healthcare Drapes and Sterile Covers, accessed on Jun. 21, 2012, at http://www.gehealthcare.com/usen/xr/surgery/docs/SurgeryDrapes&Film.pdf.
Ekliptik, "User Manual: Guiding Star/LIDIS," Jun. 16, 2010, reprinted from http://www.ekliptik.si/html/downloads/documents/manuals/LIDIS_user_manual.pdf.
Medtronic, "Orthopaedic Navigation Soluations," 2005, reprinted from http://behzadisportsdoc.com/wordpress/wp-content/uploads/2011/05/medtronic_orthonavsolutions.pdf.
GE Healthcare, "Interventional X-ray, OEC C-arm," 2012.
Notice of Reasons for Rejection for Japanese Application No. 2012-508611, dated Jan. 28, 2014.
European Search Report for European Application No. 07830964.7, dated Jun. 18, 2010, 4 pages.
Ekliptik, Guiding Star, Lidis: The Best Solution for Distal Interlocking, 2008, 2 pages.
Ekliptik, "Guiding Star", reprinted from http://ekliptik.si/content/view/37/42, on Jul. 1, 2010, 2 pages.
Office Action for U.S. Appl. No. 13/323,010, dated Jun. 4, 2013.
Office Action for U.S. Appl. No. 12/527,997, dated May 21, 2013.
International Search Report and Written Opinion for International Application No. PCT/US2013/027042, dated Jun. 12, 2013.
Communication Pursuant to Article 94(3) EPC for European Application No. 07757660.1, dated Jun. 5, 2013.
Decision of Rejection for Japanese Application No. 2009-551851, dated Jun. 11, 2013.
Communication Pursuant to Article 94(3) EPC for European Application No. 08730964.7, dated Jun. 6, 2013.
Office Action for U.S. Appl. No. 13/123,792, dated Jul. 2, 2013.
International Search Report and Written Opinion for International Application No. PCT/US2012/041613, dated Feb. 15, 2013.
Office Action for Russian Application No. 2011146669/14 dated Apr. 3, 2014.
Office Action for U.S. Appl. No. 13/358,065, dated Jun. 3, 2014.
First Office Action for Chinese Application No. 201080028779.8 dated May 23, 2014.
Office Action for U.S. Appl. No. 12/768,689, dated Jul. 9, 2014.
Office Action for Japanese Application No. 2014-515887 dated Jul. 4, 2016.
Patent Examination Report No. 1 for Australian Application No. 2012270983, dated Jan. 8, 2016.
Extended European Search Report for European Application No. 12800328.2, dated May 27, 2015.
Office Action for Russian Application No. 2013158108/14(090488), dated Apr. 14, 2016, with English-Language Synopsis.
Communication Pursuant to Article 94(3) EPC for European Application No. 12800328.2, dated Feb. 22, 2017.

* cited by examiner

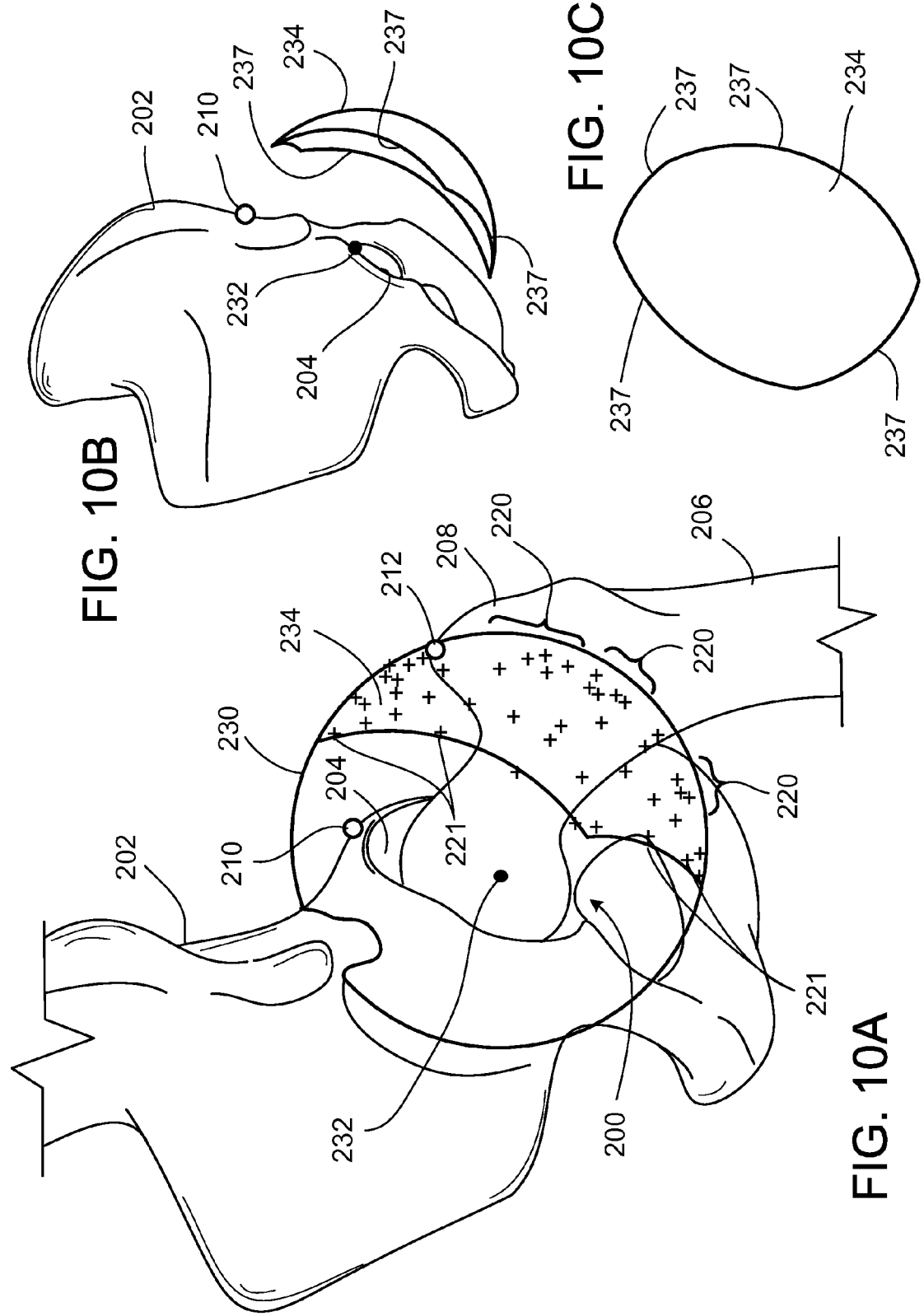

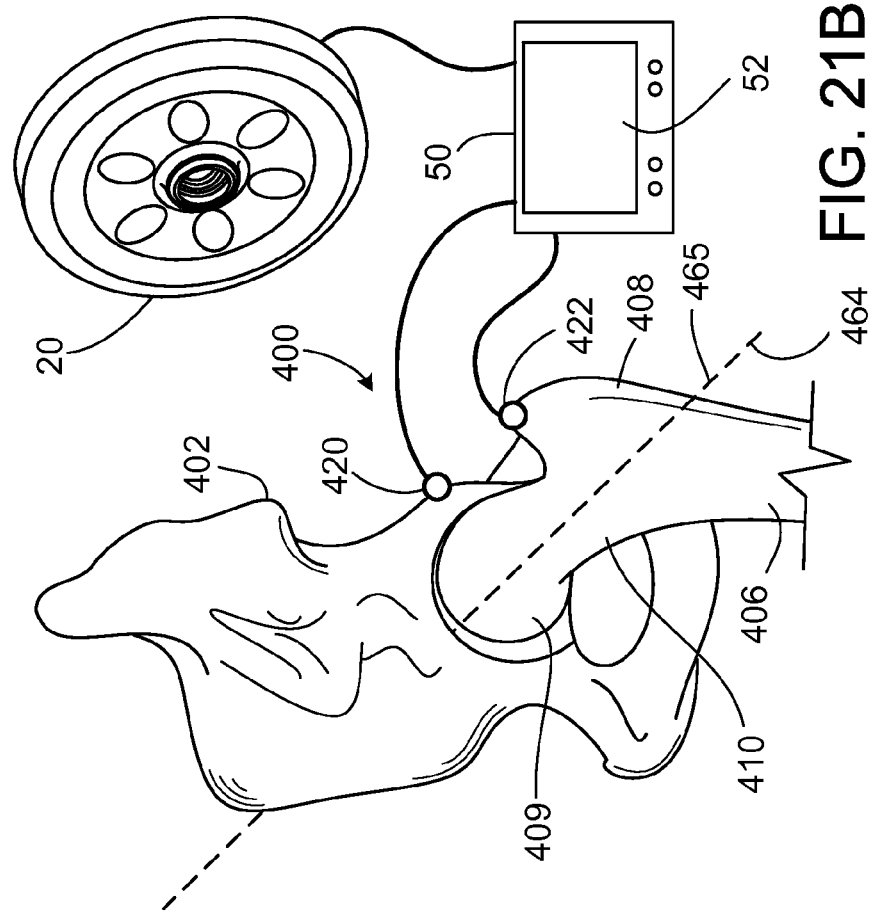
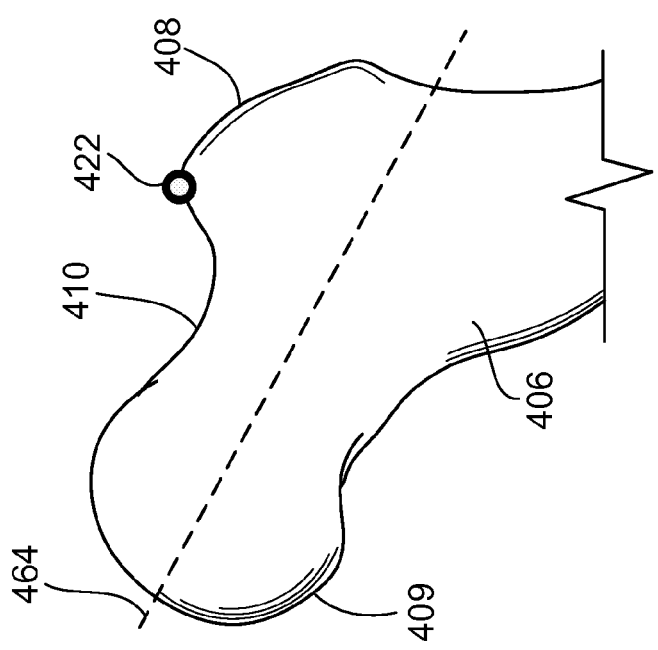
FIG. 21B
FIG. 21A

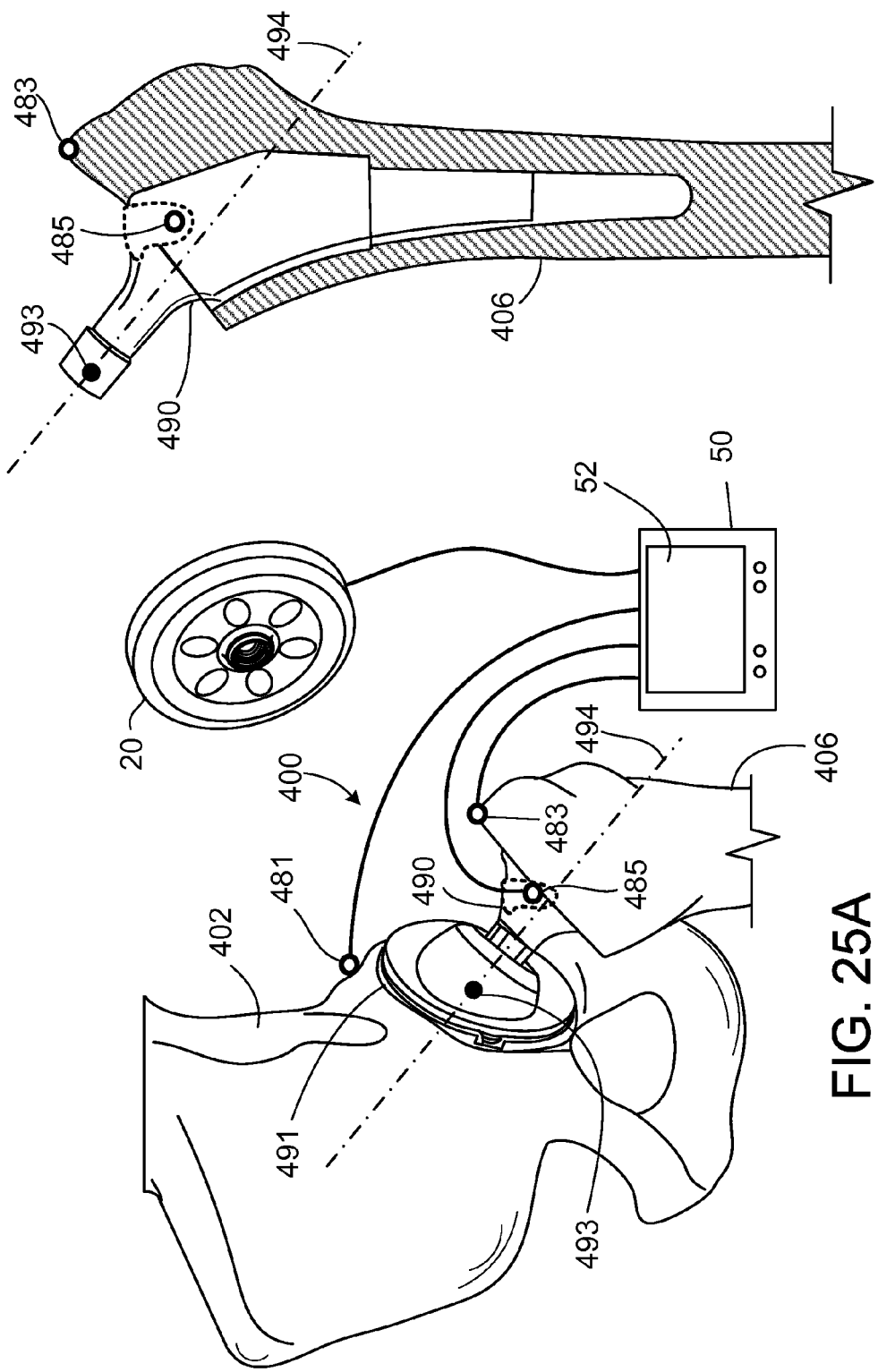

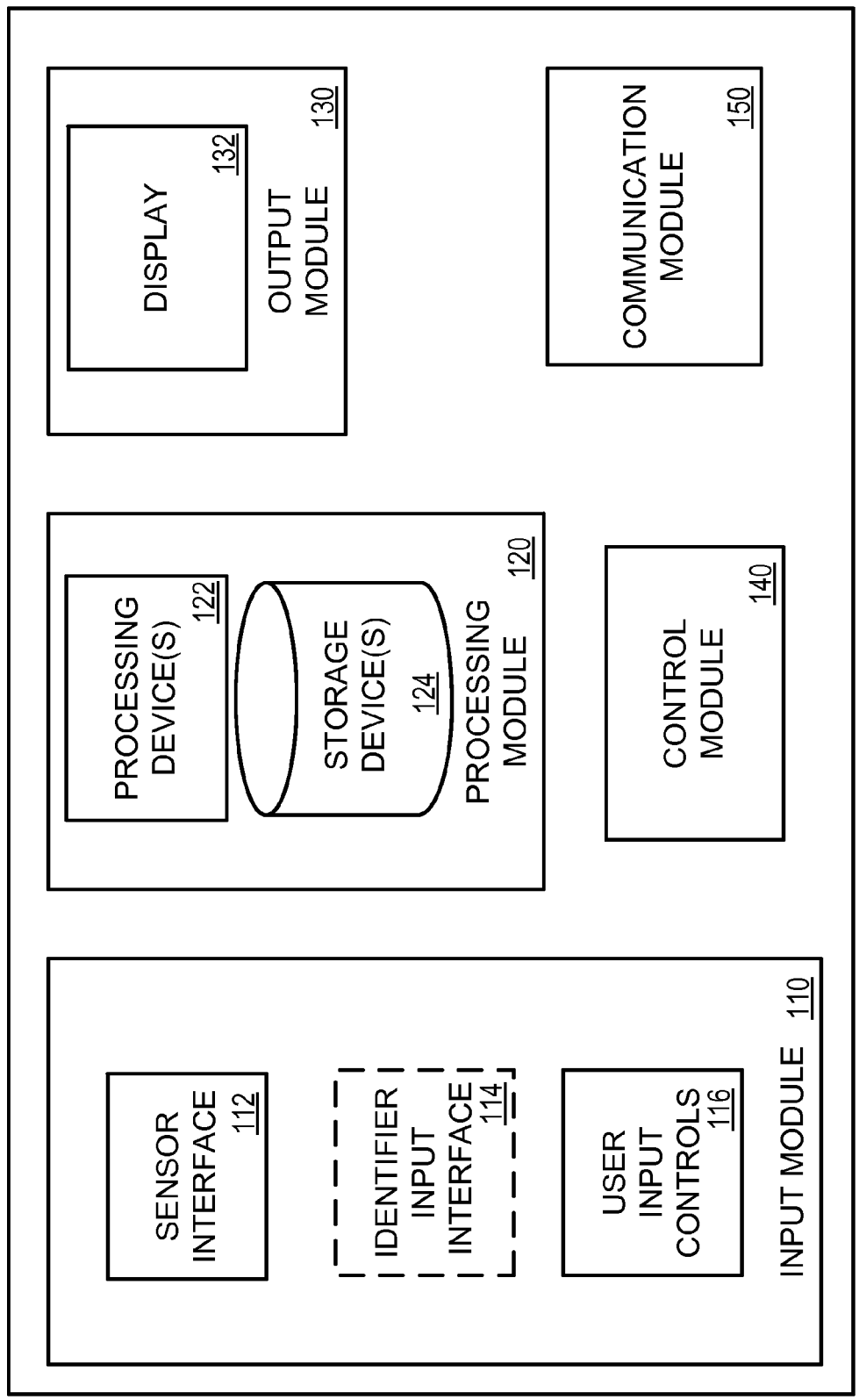

1300

```
┌─────────────────────────────────────────────────┐
│ RECEIVE INFORMATION INDICATING A POSITION OF A  │
│ FIRST REFERENCE RELATIVE TO A SECOND REFERENCE  │
│     ALIGNED RELATIVE TO AN AXIS            1302 │
└─────────────────────────────────────────────────┘
                        │
                        ▼
┌─────────────────────────────────────────────────┐
│  DETERMINE THE POSITION OF THE AXIS RELATIVE TO │
│            THE FIRST REFERENCE                  │
│                                            1304 │
└─────────────────────────────────────────────────┘
                        │
                        ▼
┌─────────────────────────────────────────────────┐
│ RECEIVE INFORMATION INDICATING THE POSITION OF AN│
│ INSTRUMENT RELATIVE TO THE FIRST REFERENCE 1306 │
└─────────────────────────────────────────────────┘
                        │
                        ▼
┌─────────────────────────────────────────────────┐
│    DETERMINE THE POSITION OF THE INSTRUMENT     │
│              RELATIVE TO THE AXIS               │
│                                            1308 │
└─────────────────────────────────────────────────┘
```

FIG. 36

SURGICAL ALIGNMENT USING REFERENCES

CROSS-REFERENCE TO RELATED APPLICATIONS

This application is a divisional of U.S. patent application Ser. No. 13/495,693, filed Jun. 13, 2012, which claims priority from, and the full benefit of, U.S. Provisional Application Ser. No. 61/497,604, filed Jun. 16, 2011, and titled "Surgical Alignment Using References," and U.S. Provisional Application Ser. No. 61/497,601, filed Jun. 16, 2011, and titled "Surgical Alignment Using References." The entire contents of the prior applications are incorporated herein by reference.

TECHNICAL FIELD

This disclosure relates to orthopaedic surgery.

BACKGROUND

Arthroplasty, commonly known as joint replacement, can restore function to damaged joints. Joint damage caused by injury, disease, or wear can restrict the function of a joint and can cause extreme pain. A damaged joint can be replaced or enhanced with a prosthesis that provides similar function to a natural joint. For example, in a hip arthroplasty procedure, an implant may be placed at the acetabulum, the femoral head, or both.

SUMMARY

In one general aspect, a method for determining alignment of an instrument relative to a joint includes: coupling a guide to the joint, the guide defining an axis and having an outer contour formed to substantially conform to a portion of the joint; attaching a first reference at a fixed position relative to the joint; using a positioning system to determine a position of the axis relative to the first reference, the position of the axis being determined based upon the position of the guide while the guide is coupled to the joint; removing the guide from the joint; and after removing the guide from the joint, positioning an instrument relative to the axis based on a position of a second reference relative to the first reference.

Implementations may include one or more of the following features. For example, the axis has a known inclination angle and a known anteversion angle relative to the joint when the guide is coupled to the joint. Using the positioning system to determine a position of the axis relative to the first reference includes positioning a reference at a position having a known offset relative to the axis. The outer contour of the guide is formed prior to use of the guide such that the outer contour substantially conforms to a receiving portion of the joint, and the guide mates with the receiving portion of the joint in a single orientation. Using the positioning system to determine a position of the axis relative to the first reference includes aligning an identifier relative to the axis, where the identifier includes at least one of an electromagnetic field generator, a magnetic sensor, and a fiducial. Using the positioning system to determine a position of the axis relative to the first reference includes engaging the instrument to the guide while the guide is coupled to the joint, and while the second reference is coupled to the instrument. The second reference includes an infrared detector, the first reference includes a fiducial, and using the positioning system to determine a position of the axis relative to the first reference includes using the positioning system such that the positioning system determines a relative position between the infrared detector and the fiducial. The second reference includes an electromagnetic field generator, the first reference includes an electromagnetic field sensor, using the positioning system to determine a position of the axis relative to the first reference includes using the positioning system such that the positioning system determines a relative position between the electromagnetic field generator and the electromagnetic field sensor. The outer contour of the guide is dimensioned to mate with an acetabulum of a particular patient in a single predetermined orientation. Coupling the guide to the joint includes mating the guide to the acetabulum in the single predetermined orientation. Attaching the first reference at a fixed position relative to the joint includes affixing an electromagnetic field sensor or a fiducial to a pelvis that includes the acetabulum. Using the positioning system to determine the position of the axis relative to the first reference includes engaging the instrument to the guide while the guide is mated to the acetabulum in the single predetermined orientation, the instrument being oriented in a first orientation relative to the acetabulum when in engagement with the guide. Positioning the instrument relative to the axis includes returning the instrument to the first orientation relative to the acetabulum after removing the guide from the joint. The position of the axis defined by the guide is determined using imaging data for the joint.

In another general aspect, a system includes: a guide having an outer contour that substantially conforms to a receiving portion of a joint, the guide defining an axis that has a known position relative to the joint when the guide is mated to the joint; a first reference device for attachment to a bone of the joint; a second reference device for coupling at a known alignment relative to the guide; and a control unit in communication with the first reference device and the second reference device, the control unit being configured to determine the position of the axis relative to the first reference device based on data that indicates a position of the second reference device relative to the first reference device when the second reference device is in a known alignment with the guide and the guide is mated to the joint.

Implementations may include one or more of the following features. For example, the axis has a known inclination angle and a known anteversion angle relative to the joint when the guide is coupled to the joint. The second reference is configured to be attached to the guide at a position having a known offset relative to the axis. The outer contour of the guide is formed prior to use of the guide such that the outer contour substantially conforms to a receiving portion of the joint, and the guide mates with the receiving portion of the joint in a single orientation. The joint is a hip joint of a particular patient, the axis is an acetabular impaction axis for the hip joint determined based on imaging data for the hip joint, and the guide is a patient-specific guide having the outer contour defined for the particular patient, the outer contour substantially conforming to one or more portions of an acetabulum of the hip joint such that the guide mates with the acetabulum in a single orientation. The system includes an electromagnetic field generator, the first reference device includes a first electromagnetic field sensor, and the second reference device includes the electromagnetic field generator or a second electromagnetic field sensor. The system includes an infrared detector, the first reference device includes a first fiducial, and the second reference device includes a second fiducial. To determine the position of the axis relative to the first reference device, the control unit is configured to determine the position of the axis in a reference frame, the first reference having a fixed position relative to the reference frame. The control unit is configured to (i) determine a position of an instrument relative to the axis while the second reference device or a third reference device is coupled to the instrument, and (ii) output, on a user interface, data indicating the position of the instrument relative to the axis. The control unit is configured to determine the position of the instrument after the guide is removed from the joint. To determine the position of the instrument relative to the axis, the control unit is configured to determine a rotational position of the instrument about the axis, and to output data indicating the position of the instrument relative to the axis, the control unit is configured to output data indicating the rotational position of the instrument about the axis. To determine the position of the axis relative to the first reference device, the control unit is configured to (i) access first data indicating a position of the axis relative to the guide, and (ii) access second indicating an offset between the second reference and the guide when the second reference device is in the known alignment with the guide. The control unit is further configured to determine a position of an instrument relative to a center of rotation of the joint or a surface of the joint based on the information indicating a position of the instrument relative to the first reference, calculate a reaming depth along the axis relative to the position of the instrument, and provide information indicating the reaming depth. To calculate the reaming depth, the control unit is configured to access information indicating one or more characteristics of an implant, determine a preferred reaming depth based on the one or more characteristics of the implant, and determine a difference between a current position of the instrument and a preferred position for the instrument, the preferred position corresponding to the preferred reaming depth. To provide information indicating the reaming depth, the control unit is configured to provide information indicating the difference between the current position of the instrument and the preferred position of the instrument.

In another general aspect, an apparatus for determining alignments relative to a joint includes one or more processing devices and one or more storage devices storing instructions that are operable, when executed by the one or more processing devices, to cause the one or more processing devices to perform operations. The operations include receiving information indicating a measured position of a first reference relative to a second reference, the measured position occurring while (i) the first reference is attached at a fixed location relative to a bone of the joint, (ii) a patient-specific guide having an outer contour that substantially conforms to a portion of the joint is coupled to the bone, and (iii) the second reference is coupled at a known position relative to the patient-specific guide. The operations include determining a position of a surgical axis relative to the first reference based on the measured position, receiving information indicating a position of an instrument relative to the first reference, after the guide is removed from the joint, determining the position of the instrument relative to the surgical axis using the position of the instrument relative to the first reference.

In another general aspect, a method of determining alignment of an instrument relative to a joint includes: receiving information indicating the position of a first reference relative to a second reference, the first reference being attached at a fixed location relative to the joint, the second reference being aligned at a known position relative to an axis that is defined by a guide coupled to the joint and formed prior to use such that outer contours of the guide substantially conform to a portion of the joint; determining the position of the axis relative to the first reference using the known position of the second reference; receiving information indicating the position of the instrument relative to the first reference; and determining the position of the instrument relative to the axis using the position of the instrument relative to the first reference.

Implementations may include one or more of the following features. For example, the information indicating the position of the instrument relative to the first reference is generated after removal of the guide from the joint. The second reference includes an electromagnetic field generator or an infrared detector. The second reference includes an electromagnetic field sensor, an infrared reflector, or an infrared emitter. Receiving information indicating the position of the instrument relative to the first reference includes receiving information indicating the position of a third reference relative to the first reference, the third reference being coupled to the instrument at a known position. The method includes accessing information indicating an offset between the position of the second reference and a center of rotation of the joint or a surface of the joint and determining the location of the center of rotation of the joint or the surface of the joint relative to the first reference. The method includes: determining a position of the instrument relative to the center of rotation of the joint or the surface of the joint based on the information indicating the position of the instrument relative to the first reference; calculating a reaming depth along the axis relative to the position of the instrument; and providing information indicating the reaming depth. Calculating a reaming depth includes: accessing information indicating one or more characteristics of an implant; calculating a preferred reaming depth using the one or more characteristics of the implant; and calculating the position of the instrument relative to a position corresponding to the preferred reaming depth. Providing information indicating the reaming depth includes providing information indicating the position of the instrument relative to the preferred reaming depth. Providing information indicating the position of the instrument relative to the preferred reaming depth includes providing information indicating a distance to be reamed to reach the preferred reaming depth. Receiving information indicating the position of a first reference relative to a second reference includes receiving information indicating a rotational position of the second reference about the axis, receiving information indicating the position of the instrument relative to the first reference includes receiving information indicating a rotational position of the instrument, and determining the position of the instrument relative to the axis includes determining a rotational position of the instrument about the axis.

In another general aspect, a control unit for determining alignment of an instrument relative to a joint, includes: an input module configured to receive information indicating the position of a first reference relative to a second reference, the first reference being attached at a fixed location relative to the joint, the second reference being aligned at a known position relative to an axis that is defined by a guide coupled to the joint and formed prior to use such that outer contours of the guide substantially conform to a portion of the joint, and information indicating the position of the instrument relative to the first reference; a processing module configured to determine the position of the axis relative to the first reference using the known position of the second reference, and the position of the instrument relative to the axis using the position of the instrument relative to the first reference;

and an output module configured to indicate the position of the instrument relative to the axis.

In another general aspect, an alignment system includes: a guide substantially conforming to a receiving portion of a joint, the guide defining an axis determined using imaging data for the joint; a first electromagnetic field sensor coupled to the guide and aligned at a known position relative to the axis; a second electromagnetic field sensor; an identifier including an electromagnetic field generator, the identifier being operatively coupled to the first electromagnetic field sensor and the second electromagnetic field sensor; and a control unit in communication with the identifier, the first electromagnetic field sensor, and the second electromagnetic field sensor, the control unit configured to determine the position of the axis relative to the second reference.

In another general aspect, a method for determining a position of an axis relative to a joint includes: attaching a first reference at a first fixed position relative to the joint; attaching a second reference at a second fixed position relative to the joint such that movement of the joint changes the position of the second reference relative to the first reference; measuring a plurality of locations of the second reference relative to the first reference, each of the plurality of locations corresponding to a different position of the joint; and determining the position of an axis relative to the first reference based on the plurality of locations and positions of axes relative to other joints.

Implementations may include one or more of the following features. For example, the location of the point is determined relative to the first reference and the position of the axis is determined relative to the first reference. The method includes measuring a position of the instrument relative to the first reference; and determining a position of the instrument relative to the axis. Measuring a plurality of locations of the first reference relative to the second reference occurs during movement of the joint.

In another general aspect, a method of calculating the position of an axis relative to a joint includes: receiving information indicating a range of motion of the joint; calculating a first point substantially corresponding to a center of rotation of the joint using the information indicating the range of motion; calculating a second point using one or more correlations between the range of motion of the joint and the ranges of motion of one or more other joints; and determining an axis between the first point and the second point.

In another general aspect, a method of determining an alignment of an instrument relative to a joint includes: receiving information identifying a plurality of locations of a first reference relative to a second reference, the first reference and the second reference being located such that movement of a joint changes the position of the second reference relative to the first reference, each of the plurality of locations corresponding to a different position of the joint; calculating a center of rotation of the joint using the plurality of locations; calculating an axis intersecting the center of rotation of the joint using the plurality of locations and information about other joints, the position of the axis being known relative to the first reference; receiving information identifying the position of the instrument relative to the first reference; and determining a position of the instrument relative to the axis.

Implementations may include one or more of the following features. For example, the method includes indicating the position of the instrument relative to the axis based on the position of the instrument relative to the second reference. The first reference is affixed to a first bone, the second reference is affixed to a second bone, and one or more of the plurality of locations correspond to an extremity of the range of motion of the joint. The first reference is affixed to the pelvis, the second reference is affixed to the femur, and the plurality of locations are measured at different positions of the femur relative to the pelvis, the different positions including positions corresponding to extremities of the range of motion of the femur relative to the pelvis. One or more of the plurality of locations are measured during movement of the femur relative to the pelvis. Calculating a center of rotation of the joint using the plurality of locations includes generating a representation of a sphere as a data fitting to the plurality of locations, and determining a location of a point corresponding to the center of the sphere. Determining the position of an axis intersecting the center of rotation of the joint using the plurality of locations and information about other joints includes: generating a first representation of the range of motion of the joint using the plurality of locations; accessing a composite representation based on measured ranges of motion of a plurality of joints, the composite representation indicating the position of a composite axis, the position of the composite axis being determined using positions of axes corresponding to the respective measured ranges of motion of the plurality of joints; and calculating a position of the axis for the joint based on one or more correlations between the first representation and the composite representation. Calculating a position of the axis for the joint includes identifying the one or more correlations between the first representation and the composite representation or preforming a data fitting of the first representation relative to the composite representation. The first representation includes a representation of a trace substantially corresponding to extremities of the range of motion of the joint, the trace being a data fitting to locations of the plurality of locations. The axes corresponding to the respective measured ranges of motion are determined using imaging data for the respective joints of the plurality of joints. The axes corresponding to the respective measured ranges of motion have known inclination angles and anteversion angles relative to the respective joints of the plurality of joints. Calculating the position of an axis intersecting the center of rotation of the joint using the plurality of locations and information about other joints includes: accessing data indicating, for each of a plurality of joints, a relationship between (i) a representation of a range of motion of a particular joint and (ii) an axis having a known inclination angle and anteversion angle for the particular joint; and calculating the position of the axis using correlations between a representation based on the plurality of locations and the accessed data.

In another general aspect, a method of analyzing joint data, includes: accessing data indicating, for each of a plurality of joints, (i) a range of motion of the corresponding joint, and (ii) the position of an axis determined for the corresponding joint relative to the range of motion of the corresponding joint; identifying relationships between the ranges of motion of the joints and the positions of the axes of the plurality of joints; and storing information indicating the identified relationships.

Implementations may include one or more of the following features. For example, for each of the plurality of joints, the position of the axis is determined using tomography data for the corresponding joint. For each of the plurality of joints, the inclination angle and anteversion angle of the position of the axis is known relative to its corresponding joint. The position of each for each axis has substantially the same nominal inclination angle and anteversion angle relative to its corresponding joint. Identifying relationships between the ranges of motion of the joints and the axes of the plurality of joints includes mapping a representation of each range of motion to a common coordinate system. Mapping a representation of each range of motion to a common coordinate system includes identifying one or more landmarks of each range of motion and aligning corresponding landmarks relative to reference positions in the coordinate system. Identifying relationships between the ranges of motion of the joints and the axes of the plurality of joints includes data fitting the data indicating the ranges of motion of the plurality of joints relative to each other. Generating a composite representation based on the ranges of motion corresponding to the plurality of joints; determining the position of a composite axis relative to the composite representation using the identified relationships; and storing information indicating the composite range of motion and the position of the composite axis relative to the composite range of motion. The method includes determining, based on the identified relationships, information indicating a tolerance about the composite axis, the tolerance indicating that a particular set of records, when oriented relative to the composite range of motion, have a corresponding axis within the tolerance. The data indicating a range of motion of each of the plurality of joints includes a representation indicating a trace substantially corresponding to extremities of the ranges of motion of the corresponding joints.

In another general aspect, a control unit for determining alignment of an instrument relative to a joint includes: an input module configured to receive information indicating a range of motion of the joint, and information indicating a position of an instrument relative to a reference; a processing module configured to calculate a location of a first point using the information indicating the range of motion, the first point substantially corresponding to a center of rotation of the joint, access data indicating one or more relationships between, for each of a plurality of joints, a range of motion and an axis having a known position relative to the range of motion, and calculate a location of a second point using the information indicating the range of motion and the accessed data; and an output module configured to provide information indicating the position of the instrument relative to an axis defined through the first point and the second point.

Implementations may include one or more of the following features. For example, a data storage module storing the data indicating one or more relationships, and the processing module is further configured to access the data indicating the one or more relationships from the data storage module. The information indicating the range of motion of the joint is a plurality of locations of representing different positions of the joint.

In another general aspect, an alignment system includes: a first reference; a second reference; an identifier operatively coupled to the first reference and the second reference; a control unit in communication with the identifier, the control unit configured to calculate a center of rotation of a joint using information indicating a plurality of locations of the first reference relative to the second reference, calculate an axis intersecting the center of rotation of the joint using the plurality of locations and information indicating positions of axes relative to the respective ranges of motion of other joints, and determine a position of an instrument relative to the axis.

In another general aspect, a method of aligning an instrument relative to a femur includes: attaching a reference at a fixed position relative to the femur; measuring a plurality of locations about a neck of the femur relative to the reference; determining a position of an axis relative to the reference using the measured plurality of locations; determining a position of an instrument relative to the reference; and aligning the instrument relative to the axis based on the measured position. The method includes inserting a pin into the femur along the axis. Attaching the reference at the fixed position relative to the femur includes attaching the reference at a greater trochanter of the femur. Determining a position of an axis relative to the reference using the measured plurality of locations includes generating a cylindrical representation extrapolated from the plurality of locations and determining a substantially central axis of the cylindrical representation.

In another general aspect, a method of indicating a position of an instrument relative to a femur includes: receiving information indicating a plurality of locations about a neck of the femur relative to a reference, the reference being located at a fixed position relative to the femur; determining a position of an axis relative to the reference using the measured plurality of locations; receiving information indicating a position of an instrument relative to the reference; and providing information indicating the position of the instrument relative to the axis.

Implementations may include one or more of the following features. For example, determining a position of an axis relative to the reference using the measured plurality of locations includes generating a representation of a cylinder extrapolated from the plurality of locations and determining a position of a substantially central axis of the cylinder. Determining a radius of the cylinder and providing information indicating the radius of the cylinder. One or more of the plurality of locations are measured by engaging a moveable probe with the neck of the femur. One or more of the plurality of locations is measured in response to activation of a triggering mechanism of the moveable probe while the moveable probe is in contact with the neck of the femur. One or more of the plurality of locations is measured in response to the moveable probe contacting the neck of the femur. Receiving information indicating a plurality of locations about a neck of the femur relative to a reference includes determining that a triggering mechanism of a moveable probe is activated and, in response to determining that the triggering mechanism is activated, recording information indicating a position of the moveable probe relative to the reference.

In another general aspect, a control unit for indicating a position of an instrument relative to a femur includes: an input module configured to receive (i) information indicating a plurality of locations about a neck of the femur relative to a reference, the reference being located at a fixed position relative to the femur, and (ii) information indicating a position of an instrument relative to the reference; a processing module configured to determine a position of an axis relative to the reference using the measured plurality of locations; and an output module configured to indicate the position of the instrument relative to the axis.

In another general aspect, a positioning system includes: a first reference; a moveable probe including a second reference; an identifier operatively coupled to the first reference and the second reference; and a control unit in communication with the identifier, the control unit configured to receive (i) information indicating a plurality of locations about a neck of a femur relative to a reference, the reference being located at a fixed position relative to the femur, and (ii) information indicating a position of an instrument relative to the reference, determine a position of an axis relative to the reference using the measured plurality of locations, and indicate the position of the instrument relative to the axis.

In another general aspect, a method for determining a difference in one or more joint characteristics includes: fixedly attaching a first reference at a first location; fixedly attaching a second reference at a second location such that movement of the joint changes the position of the second reference relative to the first reference; measuring a first plurality of locations of the second reference relative to the first reference; measuring a second plurality of locations of the second reference relative to the first reference; and determining a difference in one or more joint characteristics using the first plurality of locations and the second plurality of locations.

In another general aspect, a method for determining a difference in one or more joint characteristics includes: receiving information indicating a first plurality of locations of a first reference relative to a second reference; receiving information indicating a second plurality of locations of the first reference relative to the second reference; and determining a difference in one or more joint characteristics using the first plurality of locations and the second plurality of locations.

Implementations may include one or more of the following features. For example, the first plurality of locations indicates different positions of a joint before a surgical procedure, and the second plurality of locations indicate different positions of the joint after the surgical procedure. The first plurality of locations and the second plurality of locations are measured while the first reference is secured at a first position relative to a first bone and the second reference is secured at a second position relative to a second bone. Determining a difference in leg length using the first plurality of locations and the second plurality of locations includes: generating a first representation of a first surface using the first plurality of locations; generating a second representation of a second surface using the second plurality of locations; and comparing the first representation to the second representation. The first surface includes a portion of a sphere having a first radius, the second surface includes a portion of a sphere having a second radius, and comparing the first representation to the second representation includes determining a difference between the first radius and the second radius. The method includes determining a difference in a center of rotation of the joint based on the first plurality of locations and the second plurality of locations. The method includes determining a difference in a range of motion of the joint based on the first plurality of locations and the second plurality of locations. Determining a difference in one or more joint characteristics includes one or more of: determining a difference in leg length, determining a difference in a center of rotation of the joint, determining an offset of a range of motion of the joint, determining a difference in the size of a range of motion of the joint, and determining a difference in a shape of a range of motion of the joint. Determining a difference in one or more joint characteristics using the first plurality of locations and the second plurality of locations includes: generating a representation indicating limits of the range of motion of the joint using the first plurality of locations; generating a representation indicating limits of the range of motion of the joint using the second plurality of locations; and comparing the first representation to the second representation.

The joint is a hip joint, the first location is a fixed location relative to a pelvis of the hip joint, and the second location is a fixed location relative to a femur of the hip joint. The joint is a shoulder joint, the first location is a fixed location relative to a scapula of the shoulder joint, and the second location is a fixed location relative to a humerus of the shoulder joint.

In another general aspect, a control unit for determining a difference in joint characteristics includes: an input module configured to receive information indicating a first plurality of locations of a first reference relative to a second reference, and information indicating a second plurality of locations of the first reference relative to the second reference; a processing module configured to determine a difference in one or more joint characteristics using the first plurality of locations and the second plurality of locations; and an output module configured to indicate the difference in one or more joint characteristics.

In another general aspect, a system for determining a difference in joint characteristics includes: a first reference configured to be attached to a first bone; a second reference configured to be attached to a second bone; an identifier operatively coupled to the first reference and the second reference; and a control unit in communication with the identifier, the control unit being configured to receive (i) information indicating a first plurality of locations of a first reference relative to a second reference and (ii) information indicating a second plurality of locations of the first reference relative to the second reference, and determine a difference in one or more joint characteristics using the first plurality of locations and the second plurality of locations.

The details of one or more implementations are set forth in the accompanying drawings and the description below. Other features, objects, and advantages of the disclosure will be apparent from the description and drawings.

BRIEF DESCRIPTION OF THE DRAWINGS

FIGS. 8, 9, 10A to 10C, and 11A and 11B are illustrations of a process for acquiring data for a joint.

FIGS. 21A and 21B are perspective views illustrating a process for determining an alignment for a joint based on an alignment known relative to a bone of the joint.

FIGS. 25A, 25B, 26A, and 26B are illustrations of a process of determining alignment for a revision arthroplasty.

FIG. 27 is a block diagram of a control unit of a control unit of the system of FIG. 1 or FIG. 1.

FIGS. 29 to 31, 36 to 38, and 40 are flow diagrams illustrating example processes for determining an alignment relative to a joint.

DETAILED DESCRIPTION

Figure 1:
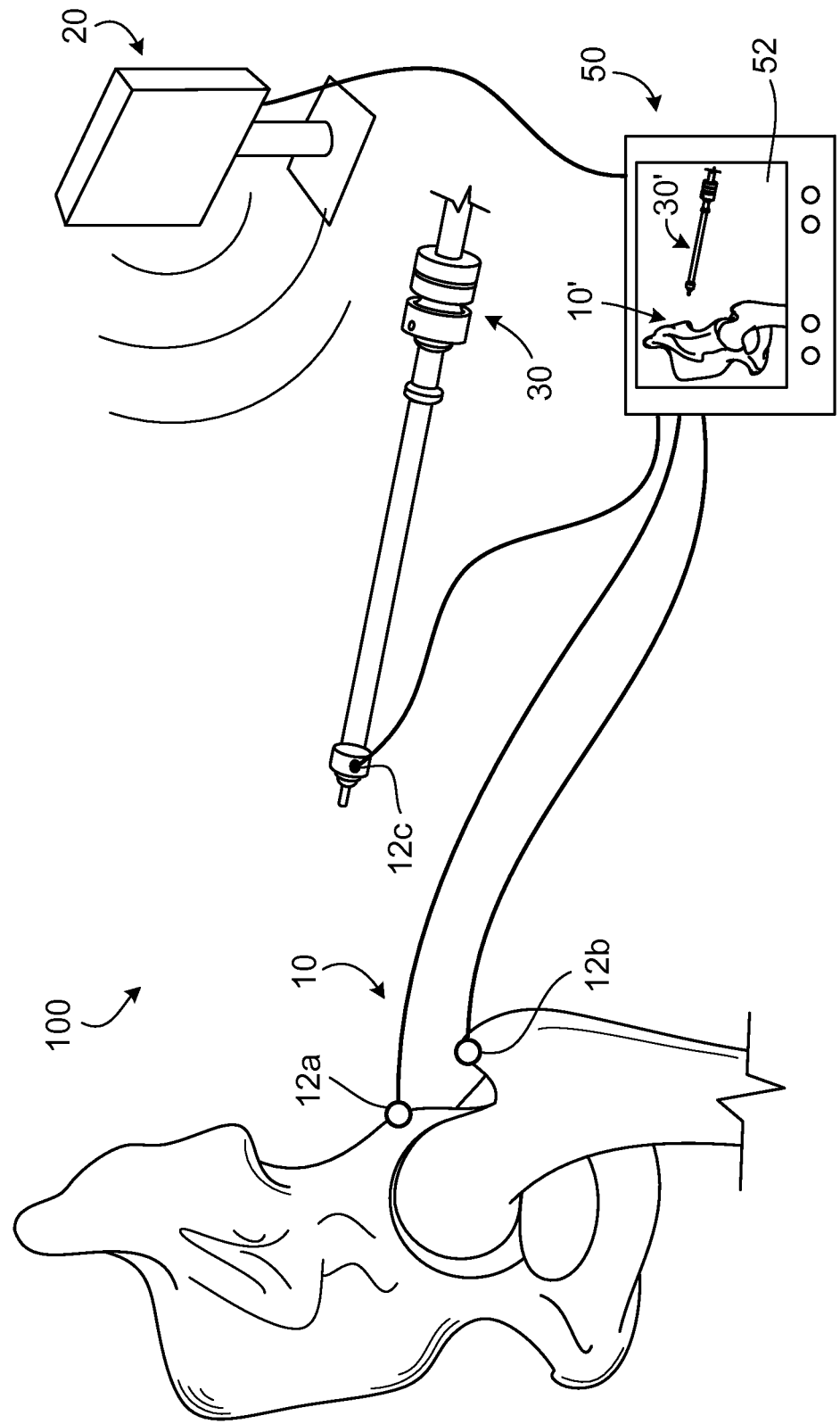
FIGS. 1 and 2 are illustrations of an alignment system.

Referring to FIG. 1, an alignment system 100 can be used to facilitate proper alignment of instruments, implants, and tissues during a surgical procedure. For example, the alignment system 100 can be used to align tissues and surgical instruments 30 during, for example, an arthroplasty of a hip joint 10. While many techniques are described below with respect to the hip joint, the same techniques are applicable to arthroplasty of other joints, including other ball and socket joints such as a shoulder joint. The techniques can also be applied to surgical procedures other than arthroplasty.

During a hip arthroplasty, the surgeon can use the system 100 to determine the position of an impaction axis relative to a hip joint. The impaction axis and other alignments can be used to, for example, prepare the surface of an acetabulum, install an acetabular implant, and prepare the femur to receive an implant. The system 100 can indicate differences between current alignments of instruments and preferred alignments, thus assisting surgeons in positioning instruments at the preferred alignments.

The system 100 includes one or more references. Positions of tissues and instruments are determined relative to one or more of the references, and positions of references are determined relative to each other. Examples of references include an identifier 20 and sensors 12a-12c. The system 100 includes an identifier 20 that communicates with one or more of the sensors 12a-12c. When in communication with the identifier 20, each sensor 12a-12c produces a signal that indicates the relative position of the sensor 12a-12c from the identifier 20.

The identifier 20, which will be described in further detail below, produces electromagnetic fields that can be detected by the sensors 12a-12c. The identifier 20 can have a generally plate-like shape and can also have other shapes. The identifier 20 can be supported by a floor-standing mount, as illustrated. The identifier 20 can alternatively be placed under a patient or at another location. As shown in other figures and as described below, the identifier 20 can be handheld or can be coupled to moveable instruments.

As used herein, a position can include both a location and an orientation. For example, data indicating a position of one reference relative to another reference can indicate a translational offset between the references as well as an angular offset and a rotational offset.

The control unit 50 receives information indicating positions of the references relative to each other. Based on the positions of the identifier 20 and the sensors 12a-12c and other known spatial relationships, the control unit 50 determines preferred alignments relative to the joint 10 and current alignments relative to the joint 10.

Relative positions of two references (e.g., the position of one reference relative to the other) can be determined directly or indirectly. For example, the relative position of a first reference and a second reference can be determined by determining the position of each reference relative to a third reference. Thus determining the position of one reference relative to another does not require measurements to occur in a reference frame defined by either of the references.

Similarly, a position can be known relative to a reference even though it is known indirectly. For example, when a relative position of a reference A and a reference B is known, and a relative position of the reference B and a reference C is known, the relative position of reference A and reference C is also known, even if that relative position is not directly stored or calculated.

The control unit 50 includes a control module configured to, for example, supply power and control signals to regulate the operation of sensors and identifiers in communication with the control unit 50. The control unit 50 includes an input module to receive signals from sensors, identifiers, and other systems. Using the information received, a processing module of the control unit 50 calculates preferred alignments of instruments 30 and tissues. The processing module also calculates the current positions of instruments and tissues relative to the preferred alignments. The control unit 50 also includes an output module that can indicate on a user interface 52 preferred alignments and actual alignments of instruments and tissues, as well as other information described below. For example, the user interface 52 can display an image that includes a representation 10' of the joint 10 and a representation 30' of the instrument 30 and can indicate the position of the instrument 30 relative to the joint 10.

Figure 2:
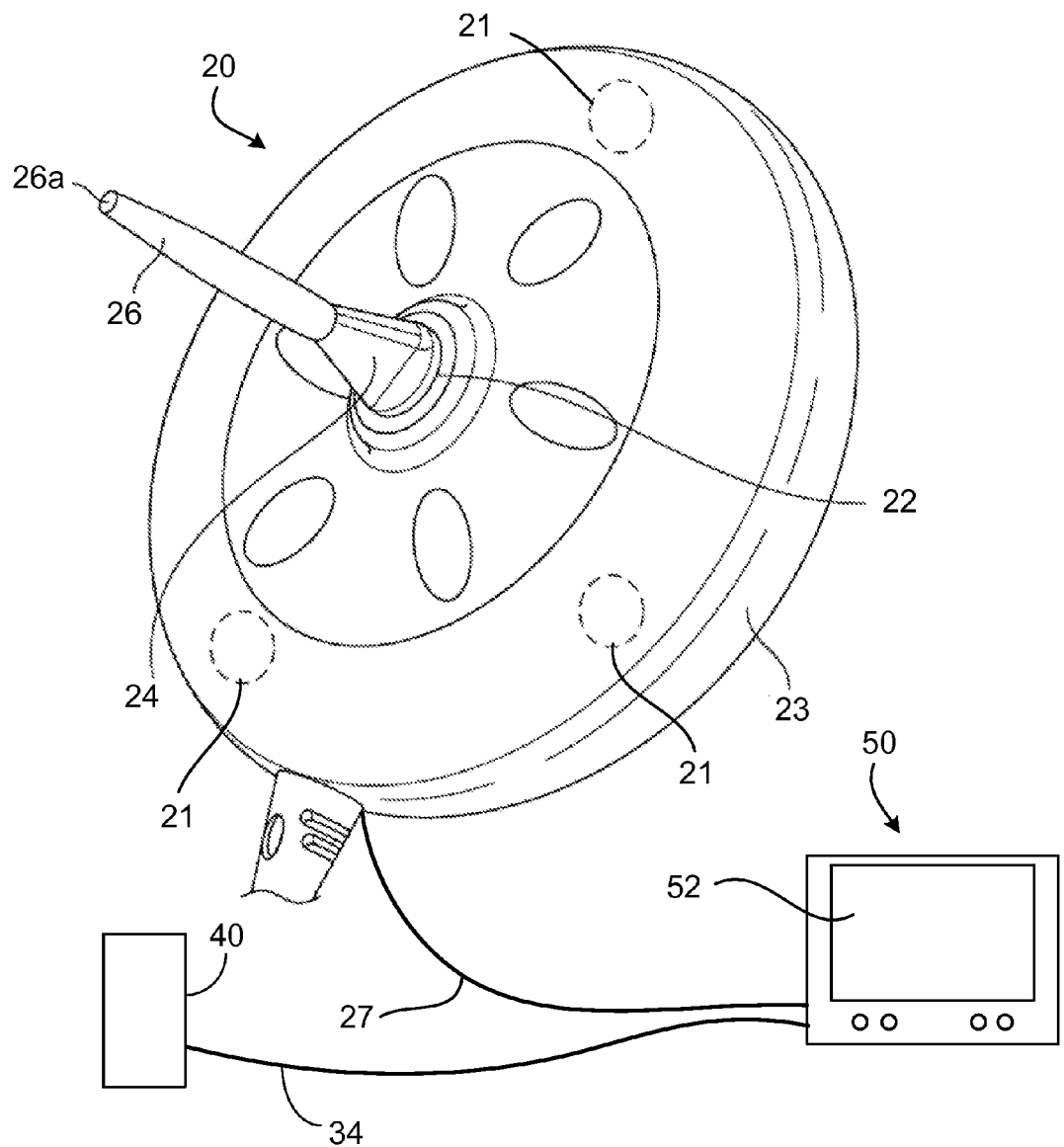

Referring to FIG. 2, in further detail, the identifier 20 includes an electromagnetic (EM) field generator 21 operable to produce an EM field that has known characteristics. The EM field generator 21 is located within a housing 23 of the identifier 20. The EM field generator 21 includes one or more coils or other components that produce EM fields. The generated EM fields are detected by one or more magnetic sensors, such as EM field sensors 40, which each produce output signals based on the EM fields detected. Any of a variety of different magnetic sensors can be used as an EM field sensor 40, for example, one or more of an inductive coil, a Hall effect sensor, a fluxgate magnetic field sensor, and a magneto-resistive sensor. When the EM field sensor 40 detects sufficient EM field energy, the EM field sensor 40 produces signals indicating the position of the EM field sensor 40 relative to the EM field generator 21.

The control unit 50 drives the EM field generator 21, receives output signals from the EM field sensors 40, and displays relative positions of the EM field sensors 40 and the identifier 20. For example, the identifier 20, sensors 40, and control unit 50 can include features as described in WIPO International Publication Nos. WO2008/106593 and WO2009/108214, each of which is incorporated herein by reference in its entirety, and as described in U.S. patent application Ser. Nos. 12/758,747 and 12/768,689, each of which is incorporated herein by reference in its entirety.

The useful range of the identifier 20 is a three-dimensional region around the identifier 20, referred to as the working volume of the identifier 20. The size and shape of the working volume is based on the characteristics of the EM fields produced by the EM field generator 21 and can be modified to be larger or smaller based on the need for targeting accuracy. The shape and size of the working volume of the identifier 20 depends in part on the configuration of the EM field generator 21, specific characteristics of the operation of the EM field generator 21, such as characteristics of a driving signal, and other factors.

In some implementations, the working volume is a region that surrounds the identifier 20. For example, the identifier 20 can be generally centrally located within the working volume. The working volume for some implementations, such as those used during alignment for arthroplasty, can extend approximately 50 cm or more in width and approximately 40 cm or more in depth and be located at a distance of about 5 cm from the identifier 20. Accordingly, a drill guide or other instrument coupled to the identifier 20 will extend, for example, more than 5 cm from the identifier 20 to ensure proper positioning within the working volume. Alternatively, for some uses, a working volume with smaller dimensions may be used to increase precision and accuracy.

The sensor 40 communicates with the EM field generator 21 of the identifier 20, for example, by receiving EM fields produced by the EM field generator 21 when the sensor 40 is located within the working volume of the EM field generator 21. The sensor 40 generates output signals that indicate strength or intensity of the EM fields detected. The sensor 40 includes, for example, an inductive sensor that is configured to respond to an EM field produced by the identifier 20 by outputting one or more induced electrical currents. The sensor 40 can include two or more inductive coils located at known, fixed positions relative to each other, and each coil can output an induced electrical current.

The sensor 40 includes a connection, such as a sensor lead 34, to transmit the output signals, or data related to the signals. The sensor lead 34 provides a wired connection for transmission of an output of the sensor 40. The sensor lead 34 can carry signals produced by the sensor 40 in response to EM fields. In some implementations, the connection can include a wireless transmitter. Additionally, the sensor lead 34 can include more than one connection, and the sensor lead 34 can carry power and control signals in addition to signals or data, and bi-directional communication is possible. For example, information regarding calibration of the sensor 40 can be stored in a storage device coupled to the sensor 40.

The signals produced by the sensor 40 allow the relative position of the identifier 20 and the sensor 40 to be determined. At different positions within the working volume of the EM field generator 21, the sensor 40 detects different EM field energy, resulting in different output signals. The output signals can be used to accurately determine the position of the identifier 20 relative to the sensor 40. A sensor 40 located outside the working volume of the identifier 20 may not receive adequate EM energy from the field generator 21 to generate output signals that can be used to accurately determine the relative position of the sensor 40 and the identifier 20.

The outputs of the sensor 40 allow determination of the position of the sensor 40 in up to six degrees of freedom, such as along three translational axes, generally called X, Y, and Z, and three angular orientations, generally called pitch, yaw, and roll, which are each defined as rotation about one of the three translational axes. Thus the signal produced by a single sensor 40 can define an axis relative to the identifier 20. A sensor indicating as few as three degrees of freedom can be used to measure a location in a reference system. To define the position of an axis, a sensor permitting determination of at least five degrees of freedom can be used. When information about the position of an axis and a rotational position about the axis is desired, a sensor indicating data for six degrees of freedom can be used.

References, such as the sensor 40 and the identifier 20, can be coupled to tissues or to instruments so that the positions of the tissues or instruments can be determined based on the positions of the references. A reference can be attached at a known position relative to an instrument or tissue, or to a position that is not known.

For some measurements, the dimensions of a tissue or instrument and the position at which a reference is initially attached need not be known. For example, a first reference may be attached at an arbitrary position relative to the instrument or tissue. While the first reference remains in a fixed position relative to the instrument (e.g., the first reference moves with the instrument), the instrument can be positioned relative to a bone coupled to a second reference. At a particular position, the control unit 50 determines offsets between the positions of the references, and stores the offsets. When the relative position of the instrument and the bone changes, the control unit 50 can indicate deviations from the previously measured relative position. Thus even when the references have not been calibrated relative to each other and the references are not located at known positions of the instrument or tissue, the control unit 50 can assist the operator of the system 100 to return the instrument to the measured position relative to the bone.

For other measurements, the sensor 40 can be coupled at a known position relative to the instrument or tissue. For example, the sensor 40 can be located at a landmark of the instrument 30 and oriented at a known orientation relative to the instrument 30. The operator of the system 100 inputs to the control unit 50 information indicating the location and orientation of the sensor relative to the instrument 30, for example, by inputting information that identifies the landmark. The control unit 50 accesses information indicating the dimensions of the instrument 30 and the position of the landmark relative to features of the instrument 30. For example, the control unit 50 can access information indicating an offset between the landmark and an end of the instrument 30 that is configured to engage tissue.

Because the position of the sensor 40 is known relative to the instrument 30, the control unit 50 can determine the position of the instrument 30 based on the position of the sensor 40. For example, to determine the position of the end of the instrument 30, the control unit 50 determines the position of the sensor 40, and adjusts the position by the offset between the sensor 40 and the end. Thus when the position of the sensor 40 is determined relative to a reference, the position of the end of the instrument 30 can also be determined relative to the same reference.

In some implementations, a surgeon or other operator of the system 100 can grip the identifier 20 by the housing 23 to position the identifier 20 relative to a patient, an instrument, and/or a sensor 40. The identifier 20 can include a coupling member 22 to which instruments and other attachments are coupled. By orienting the identifier 20 relative to an operation site, the operator also orients the coupled instrument relative to the operation site. For example, the coupling member 22 can receive a drill guide attachment 24 coupled to a drill guide 26. The identifier 20 can be used to position the drill guide 26 so that a drill bit or guide pin inserted through the drill guide 26 is guided to the position required by or appropriate for a medical procedure. Attachments can also be included to couple a reamer, broach, impactor, and other instruments at known positions relative to the identifier 20. The instruments can be comprised of non-ferritic materials to limit interference with the EM communication between the identifier 20 and the sensors 40.

In some implementations, the identifier 20 that includes the EM field generator 21 is a standalone unit or is mounted to a chassis. The identifier 20 may thus remain in a stationary position while instruments are positioned relative to an operation site, or may be moved independent of the movement of instruments. A second sensor 40 is coupled to a surgical instrument and communicates with the EM field generator 21. The control unit 50 receives output signals of both the sensor 40 coupled to the instrument and the sensor 40 coupled to the instrument. The control unit 50 can determine position of the identifier 20 relative to the instrument 30 based on the signals of the two sensors 40. In some implementations, additional sensors 40 can be used.

The control unit 50 controls the operation of the identifier 20 and receives inputs from one or more sensors 40. The control unit 50 can communicate with the identifier 20 over a wired or wireless link to transmit power and control signals controlling the operation of the EM field generator 21. For example, the identifier 20 can include a cable 27 that provides a connection to the control unit 50.

The control unit 50 includes one or more processing devices that are configured to determine relative positions of the EM field generator 21 of the identifier 20 and each of the sensors 40. Because the position of each sensor 40 is determined relative to the same reference, the EM field generator 21, the one or more processing devices can determine the position of each sensor 40 relative to each other sensor 40. Using the signals from the sensors 40, the control unit 50 determines positions of the instruments 30 relative to one or more references.

The control unit 50 includes a display on which a graphical user interface 52 is presented to a surgeon. In some implementations, the control unit 50 outputs on the user interface 52 an indication whether a current position of the instrument 30 is acceptable relative to a preferred position. For example, the output on the user interface 52 can include one or more elements, such as an element representing the angle of the instrument 30 relative to a surgical alignment, one or more elements representing acceptable positions of the instrument 30 relative to the surgical alignment, one or more elements representing unacceptable positions of the instrument 30 relative to the surgical alignment, a numeric indication of the angle of the instrument 30 relative to anatomical axes, an element indicating that the current position of the instrument 30 is acceptable, and an element indicating that the current position of the instrument 30 is unacceptable.

The system 100 can be used for a number of measurements and procedures, including, for example: (1) determining a surgical alignment using a patient-specific guide; (2) determining a surgical alignment using stored data; (3) determining a surgical alignment by measuring locations about a bone of a joint; (4) determining a surgical alignment based on a known position of a joint; (5) trialing components to select an implant; (6) determining characteristics of a joint and identifying changes in characteristics of a joint; and (7) determining alignments for revision procedures. Examples of methods of using the system 100 are described below.

1. Alignment Using a Patient-Specific Guide

A surgeon can use the system 100 to determine the position of a surgical alignment relative to a joint. For example, the surgeon can use the system 100 to determine the position of an impaction axis having a known position relative to the anatomy of a patient.

In hip arthroplasty, an acetabular implant, such as a cup, is often installed along an impaction axis. The impaction axis used during the procedure determines the installed orientation of the acetabular implant, for example, an acetabular cup. A surgeon prepares the acetabulum to receive the acetabular cup by reaming the acetabulum, often by orienting a reamer relative to the impaction axis. The surgeon then drives the acetabular cup into the prepared acetabulum along the impaction axis. The impaction axis used during the arthroplasty procedure can significantly affect the performance of the reconstructed joint.

The preferred orientation in which the acetabular cup should be installed can be indicated by a cup anteversion angle and a cup inclination angle. The face or rim of the acetabular cup can define a plane. The cup inclination angle can be an angle in the coronal plane between the face of the cup and the sagittal plane. The cup anteversion angle can be an angle in the transverse plane between the face of the cup and the sagittal plane. A preferred installed orientation for an acetabular cup can be, for example, 45 degrees cup inclination and 20 degrees cup anteversion.

The impaction axis passes through the center of the acetabular cup and is oriented orthogonal to the face of the acetabular cup when the cup is in the preferred orientation. Installing the acetabular cup along the impaction axis positions the acetabular cup in the preferred orientation.

For simplicity in description, anteversion and inclination for the impaction axis are referred to herein as corresponding to orientations with equivalent cup anteversion and cup inclination values. For example, the anteversion angle for the impaction axis can be measured as an angle between the coronal plane and a projection of the impaction axis onto the transverse plane. The inclination angle for the impaction axis can be measured as an angle between the transverse plane and a projection of the impaction axis onto the coronal plane. Under such definitions, a cup anteversion angle of 20 degrees corresponds to an impaction axis anteversion angle of 20 degrees, even though such angles are not measured relative to the same reference planes. The definitions described above are given as examples to simplify description. In implementations, other definitions for inclination and anteversion (e.g., standard anatomic, operative, or radiological definitions) and other anatomic reference systems to define implant placement can alternatively be used.

To determine the position of the impaction axis relative to a patient's joint, a surgeon can use a patient-specific guide that is custom-shaped to be received into the joint. The guide can be pre-operatively shaped to conform to the joint. When located in the joint, the guide can indicate the alignment of an impaction axis having a known inclination angle and a known anteversion angle relative to the joint, or rather, relative to the anatomical planes of the body of which the joint is a part.

As an example, using the guide and the system 100, a surgeon can determine the position of the impaction axis relative to the joint. The surgeon places a first reference at a fixed position relative to the joint, for example, at the pelvis of a hip joint. The surgeon places the guide in the joint, and aligns a second reference relative to the impaction axis indicated by the guide. In this alignment, the second reference marks the position of the impaction axis relative to the first reference. The control unit 50 determines the positions of the references relative to each other, and records the position of the impaction axis relative to the first reference. The surgeon then removes the guide from the joint. Because the guide is removed from the joint, the surgeon has unobstructed access when preparing the acetabulum and implanting an acetabular implant.

The system 100 uses the recorded position of the impaction axis relative to the first reference to indicate the positions of instruments relative to the position of the impaction axis. For example, the second reference can be coupled to an instrument. As the second reference and the instrument move together, the control unit 50 calculates differences between the current position of the second reference and the previously determined position of the second reference, which corresponds to the alignment along the impaction axis. The control unit 50 outputs information that assists the surgeon to align the instrument along the impaction axis, for example, by returning the second reference to its position when aligned relative to the guide or to a particular offset from the measured position. Thus assisted by the system 100, the surgeon can orient instruments to perform a surgical procedure relative to the impaction axis, without physical contact with the guide during reaming and impaction.

The system 100 assists the surgeon in achieving the alignment indicated by the guide, while allowing the surgeon to make adjustments to address changed conditions and discoveries made during surgery.

1.1 Pre-Operatively Shaping a Guide

Figure 3A:
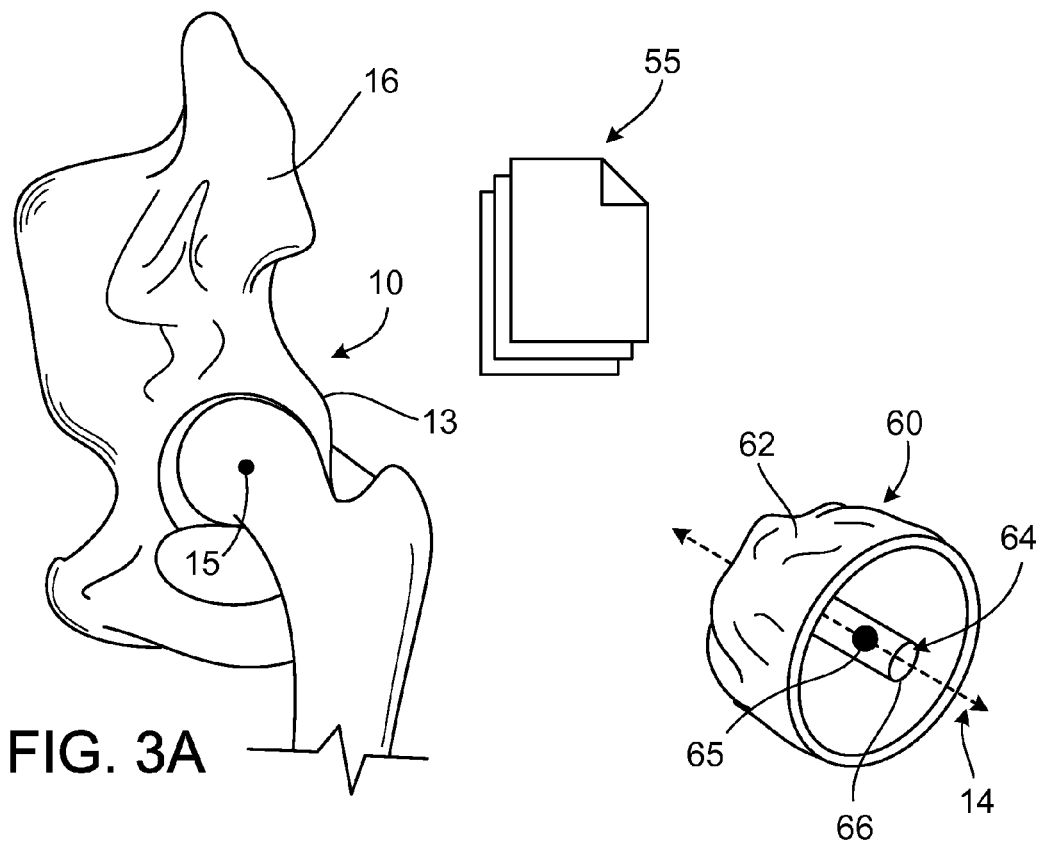
FIG. 3A is a perspective view illustrating a joint.

Referring to FIG. 3A, information indicating the contours of the hip joint 10 is acquired. The information can include imaging data 55 for the hip joint 10 acquired prior to surgery. The joint 10 can be imaged using tomography techniques such as computerized tomography (CT) or magnetic resonance imaging (MRI). Other examples of imaging data include X-ray images and ultrasound scan data.

Figure 3B:
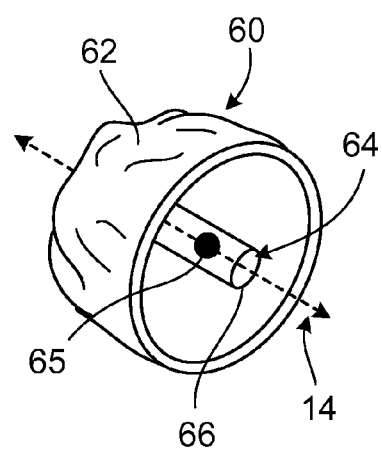
FIG. 3B is a perspective view of an acetabular guide for the joint.

Referring to FIG. 3B, using the imaging data 55, a guide 60 is fabricated to substantially conform to a receiving portion of the joint 10, such as one or more portions of the acetabulum 13. The acetabulum of each hip joint is unique. Outer contours 62 of the guide 60 are formed to substantially match contours of the acetabulum 13 such that the guide 60 mates with the acetabulum 13. Features of the acetabulum 13 determined from the imaging data 55 are used to shape corresponding mating surfaces (e.g., the outer contours 62) of the guide 60. Thus the guide 60 is patient-specific, as a result of custom-fitting to the particular joint 10 described in the imaging data 55.

The guide 60 can conform to the acetabulum 13 such that the guide 60 mates with the acetabulum 13 in a single orientation. The guide 60 can be formed of a rigid material, for example, plastic, metal, or ceramic. The guide 60 can be shaped, dimensioned, and contoured such that the outer contours 62 conform to a sufficient portion of the acetabulum 13 to form a stable engagement when the guide 60 is received to the acetabulum 13. In some implementations, the guide conforms to the majority of the surface of the acetabulum 13.

In addition to, or as an alternative to matching surfaces of the acetabulum 13, the guide 60 can also conform to other features, including portions of the pelvis near the acetabulum 13. The guide 60 can also conform to all of or portions of, for example, the acetabulum rim, the greater sciatic notch, a portion of the ilium, and/or the anterior inferior iliac spine.

Because pre-operative imaging data 55 is used to form the guide 60, the guide 60 can be shaped to conform to the acetabulum 13 prior to surgery. The guide 60 can be delivered to the surgeon as a pre-formed unit having generally non-adjustable outer contours 62. For example, the guide 60 can be molded, cut, machined, three-dimensionally printed, or otherwise manufactured to an appropriate shape. The guide 60 may be formed as a block or integral unit.

The imaging data 55 is also used to determine the position of an impaction axis 14 relative to the joint 10. The impaction axis 14 is selected using the imaging data 55 to have a known inclination angle and a known anteversion angle relative to the patient's anatomy. The position of the impaction axis 14 can optionally be indicated on the guide 60, thus indicating the position of the impaction axis 14 relative to the contours of the acetabulum. When the guide 60 is received in the joint 10, the position indicated by the guide 60 coincides with the position of the impaction axis 14. For example, the guide 60 can define a guide hole 64 partially or completely through the guide 60 along the impaction axis 14. In addition, or alternatively, markings or features of the guide 60 can indicate the orientation of the axis 14 relative to the guide 60.

The guide 60 optionally includes indicia identifying the patient, for example, a patient name or patient number labeled on the guide 60. Other identifying information can be labeled on or embedded in the guide 60 to associate the guide 60 with, for example, the corresponding joint 10, patient, surgeon, or hospital.

The imaging data 55 can also be used to determine the center of rotation point 15 of the joint 10 (FIG. 3A) (e.g., the center of motion point of the joint 10). The position of a reference point 65 relative to the guide 60 can be determined, where the reference point 65 corresponds to the center of rotation point 15 of the joint 10. For example, the reference point 65 can be determined such that when the guide 60 resides in the acetabulum 13, the reference point 65 coincides with the center of rotation point 15 of the joint 10. Alternatively, the reference point 65 can be determined relative to a landmark or feature of the guide 60, such as a portion 66 configured to engage an instrument 30 or sensor. The position of the reference point 65 can be marked on guide 60 or can be indicated separately.

In some implementations, the distance between a landmark of the guide 60 and outer contours 62 of the guide 60 can be determined. For example, the distance along the impaction axis 14 between the portion 66 and the outer contours 62 can be determined. Alternatively, the portion 66 can be formed or marked at a known distance from the outer contours. Other distances, such as the thickness of the guide 60 at different landmarks of the guide 60, can also be measured and recorded, or alternatively formed to predetermined specifications. Data indicating these distances can be accessed by the control unit 50.

1.2 Determining the Orientation of the Impaction Axis

Figure 3C:
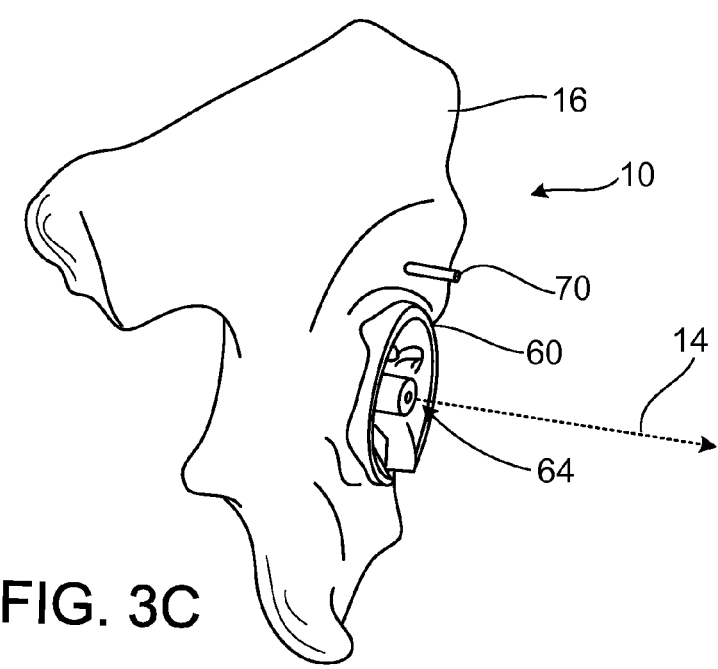
FIG. 3C is a perspective view of the acetabular guide of FIG. 3B received in the joint.

Referring to FIG. 3C, the surgeon creates an incision to access the joint 10 and dislocates the joint 10. The surgeon inserts the guide 60 into the joint 10 such that it mates with the acetabulum 13. Because the guide 60 substantially conforms to portions of the acetabulum 13, the acetabulum 13 mates with the guide 60 in a known orientation. As a result, when the guide 60 is received by the acetabulum 13, the position indicated by the guide hole 64 or other markings of the guide 60 indicates the position of the impaction axis 14 relative to the joint 10.

Using a pre-operatively formed guide 60 can significantly simplify operating procedures and reduce operating time. For example, the surgeon need not reshape or adjust the guide 60 during the procedure. The surgeon is also not required to manually identify features of the acetabulum 13. Thus in many instances the surgeon can quickly position the guide 60 in a stable engagement with the acetabulum 13 based on contact with the acetabulum 13. Thus using the pre-formed guide 60 to determine the position of the impaction axis 14 can be faster and more accurate than determining the position of an axis using anatomical references visually identified during a procedure. In addition, the stability of the guide 60 when received by the acetabulum 13 can provide confirmation to the surgeon that the guide 60 is correctly positioned.

Because the guide 60 need not remain in the acetabulum 13 when reaming and impaction occur, the guide 60 can engage as much of the acetabulum 13 as is useful to provide a precise connection with the acetabulum 13. The guide 60 can achieve a known mating position by engagement with the acetabulum 13, and in some implementations, without engaging other surfaces of the pelvis 16. As a result, to position the guide 60, the surgeon is not required to clear soft tissue from surrounding surfaces of the pelvis 16. Thus the surgeon can quickly position of the guide 60 without causing extensive soft tissue trauma outside the acetabulum 13.

Moreover, the surgeon's access the acetabulum 13 is generally limited due to the tissues surrounding the joint 10. For instance, the surgeon may access the acetabulum 13 through a relatively narrow space, with the acetabulum 13 located at a depth that may be roughly 6 to 9 inches from the incision. Nevertheless, the surgeon can often mate the guide 60 to the acetabulum 13 in a straightforward manner, without requiring unobstructed visibility to place the guide 60.

The surgeon attaches a first reference at a fixed location relative to the joint 10, such as a bone of the joint 10. The first reference can be attached before or after inserting the guide 60 in the joint 10. For example, the surgeon attaches an EM field sensor 70 to the pelvis 16, located outside the acetabulum 13 so as not to interfere with the surgery. The sensor 70 can include a housing with a threaded portion, allowing the sensor 70 to be screwed into the pelvis 16 at a fixed location. The sensor 70 can be installed so that it moves with the pelvis 16. The sensor 70 can be implanted near the acetabulum 13, for example, through the same incision or channel used to access the acetabulum 13. Attaching the sensor 70 at a fixed position relative to the pelvis 16 and maintaining the sensor 70 in its position permits the control unit 50 to use the sensor 70 to establish a consistent reference frame with regard to the pelvis 16.

The position of the sensor 70 need not be known relative to the joint 10 when the sensor 70 is implanted. The position of the axis 14 relative to the sensor 70 is determined later by the system 100, thus the surgeon has flexibility to select the location for the sensor 70. In some implementations, the sensor 70 can be implanted such that the sensor 70 is oriented substantially parallel to the impaction axis 14 using the indications on the guide. As a result, the position of the sensor 70 can provide a visual indication of the orientation of the impaction axis 14. The sensor 70 can thus provide visual confirmation of the trajectory of the impaction axis 14 indicated later by the control unit 50.

Figure 4A:
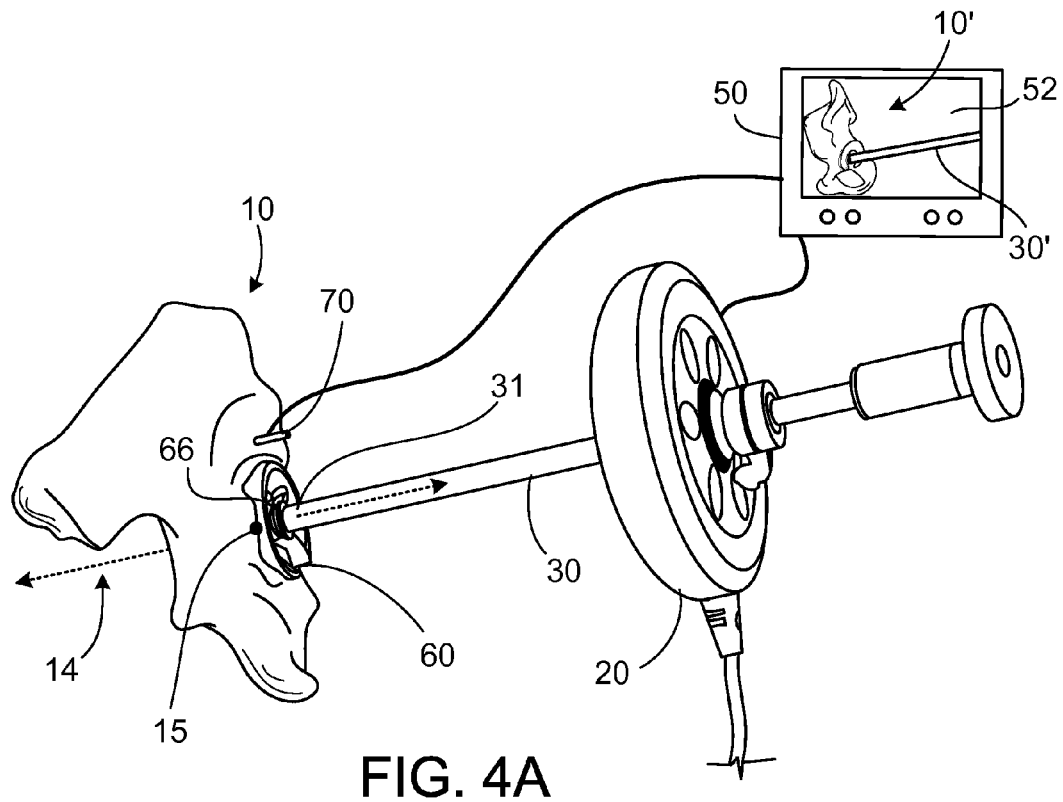
FIGS. 4A and 4B are perspective views illustrating techniques for determining the position of an axis.
Figure 4B:
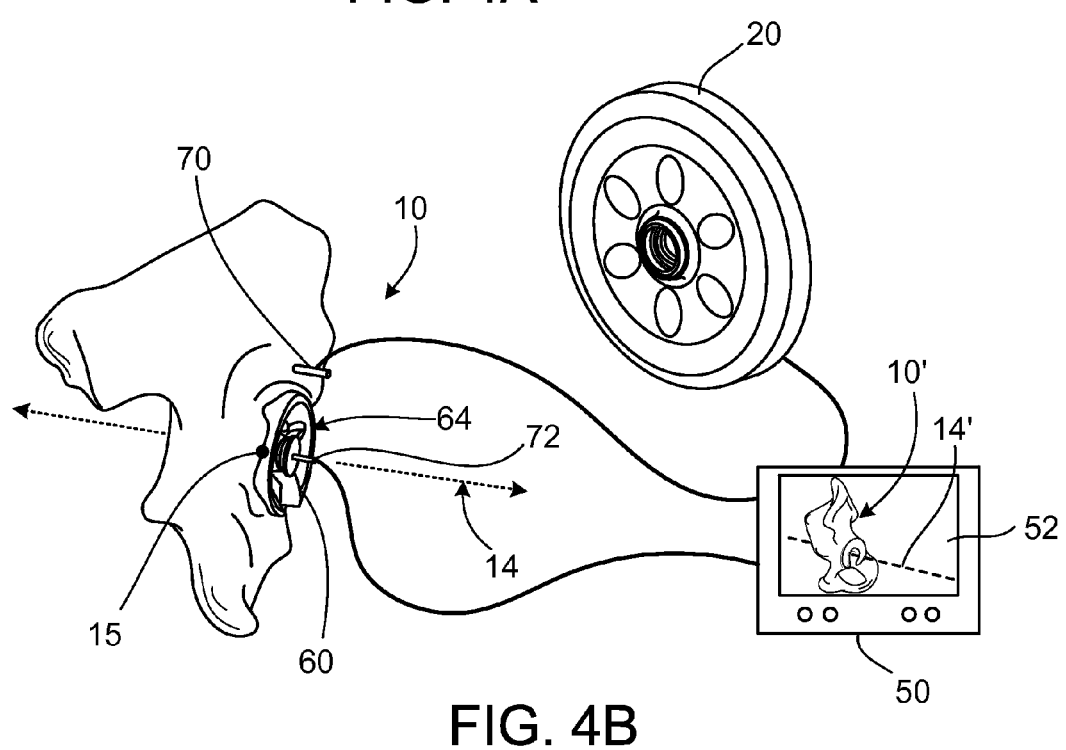

FIGS. 4A and 4B illustrate alternative procedures for determining the position of the impaction axis 14 relative to the joint 10 using the guide 60. The orientation is determined by positioning a second reference at a known alignment relative to the axis 14 and measuring the position of the second reference relative to the first reference (the sensor 70) while in the known alignment. Thus the position of the impaction axis 14 is determined relative to the reference frame of the sensor 70. The second reference can include, for example, the identifier 20 (FIG. 4A) or a second EM field sensor 72 (FIG. 4B). The control unit 50 can indicate on the user interface 52 one or more of the positions of the instrument 30, sensors, and when determined, the impaction axis 14 and the center of rotation point 15. These indications can be displayed with a three-dimensional view of the joint 10.

Referring to FIG. 4A, the surgeon uses the identifier 20 as a reference to determine the position of the axis 14 relative to the sensor 70. An instrument 30, such as a reamer, is coupled to the identifier 20. The surgeon inserts an end 31 of the instrument 30 into the guide hole 64 of the guide 60, thus aligning the instrument 30 and the identifier 20 along the impaction axis 14. The sensor 70 detects the EM fields generated by the EM field generator 21 of the identifier 20 and transmits a signal to the control unit 50. Based on the signal, the control unit 50 determines the position of the identifier 20 relative to the sensor 70. The surgeon selects a control on the user interface 52 indicating that the identifier 20 is aligned relative to the guide 60. In response, the control unit 50 records the position of the identifier 20 as corresponding to the position of the preferred impaction axis 14.

The orientation of the identifier 20 relative to the instrument is known. For example, the coupling member 22 (FIG. 2) can attach the identifier 20 so that the instrument 30 extends in a known position from the identifier 20. In some implementations, additional information about the position of the identifier 20 relative to the instrument 30 is also known, such as the position of the identifier 20 along the length of the instrument 30 and a rotational position of the identifier 20 about the instrument 30.

One or more of the known positions or offsets can be entered on the control unit 50 by the surgeon. For example, the surgeon can indicate that a standard offset or position is used. The surgeon can input information indicating that a particular model of instrument 30 is used. The control unit 50 can access information indicating dimensions of the instrument 30 and positions of various landmarks along the instrument 30. The surgeon can also select a landmark of the instrument 30 that engages the guide 60, or a landmark at which the identifier 20 is coupled. The surgeon can also enter non-standard offsets manually. The control unit 50, having access to dimensions of the instrument 30 and particular landmarks at known positions of the instrument 30, can calculate or access offsets between the landmarks. In some implementations, data that indicates known positions can be accessed from a storage device of the control unit 50 or over a network.

The control unit 50 can determine the location of the center of rotation point 15 of the joint 10 relative to the sensor 70. The position of the identifier 20 relative to the end 31 can also be known. For example, the identifier 20 can be coupled at a landmark of the instrument 30, resulting in a position with a known first offset from the end 31. Based on the imaging data 55 for the joint 10, a second offset between the location of the center of rotation point 15 and the portion 66 of the guide 60 can also be known and accessed by the control unit 50. The instrument 30 can engage the guide 60 at a known position, for example, the end 31 of the instrument 30 can engage the portion 66 of the guide 60. Thus from the position of the identifier 20, measured when the end 31 is engaged with the portion 66, adding the first offset and the second offset results in the position of the center of rotation point 15, relative to the sensor 70.

In a similar manner, the control unit 50 can determine the location of a surface of the acetabulum 13. The guide 60 can have a known offset or thickness along the impaction axis 14 between the portion 66 (which engages the end 31 of the instrument 30) and the outer contours 62 (which engage the acetabulum 13). Data indicating this offset can be accessed by the control unit 50, and together with data indicating the offset between the identifier 20 and the end 31, can be used to determine the position of the surface of the acetabulum 13 along the impaction axis 14 from the position of the identifier 20.

In some implementations, rather than aligning the instrument 30 and the identifier 20 along the impaction axis 14, the identifier 20 can be oriented at a different known position relative to the impaction axis 14. For example, the identifier 20 can engage the guide 60 at a position with a known translational offset and/or angular offset relative to the impaction axis 14. The control unit 50 can use the known offset, entered by the surgeon or accessed from another source, to determine the position of the impaction axis 14.

Referring to FIG. 4B, the position of the axis 14 can alternatively be determined relative to the EM sensor 70 by aligning a second EM sensor 72 relative to the axis 14. The surgeon positions the second sensor 72 at a known position relative to the axis 14. For example, the surgeon couples the second sensor 72 to the guide 60 at the guide hole 64 along the axis 14, for example at the portion 66. The sensors 70, 72 are brought within the working volume of the EM field generator 21 of the identifier 20. In some implementations, the second sensor 72 is attached to the guide 60 prior to coupling the guide 60 to the joint 10. For example, the guide 60 can be provided to the surgeon with the second sensor 72 attached at a known location and/or orientation relative to the axis 14.

Because the position of interest is the position of the sensors 70, 72 relative to each other, the precise position of the identifier 20 is not critical. The instrument 30 can be physically detached from the EM field generator 21 so that the instrument 30 is freely moveable with respect to the identifier 20. For example, the EM field generator 21 of the identifier 20 may be free-standing or may have a fixed mount. In some implementations, the identifier 20 may be placed beneath the patient, for example, under the hip joint that is not being operated on.

Because the identifier 20 communicates with the sensors 70, 72 using EM fields, an unobstructed line of sight between the identifier 20 and the sensors 70, 72 is not required. In addition, because the sensors 70, 72 are small and can be attached directly to bone, normal vibrations of the bone does not practically affect the measurement.

The sensors 70, 72 detect the EM fields produced by the EM field generator 21, and transmit signals that indicate the position of each sensor 70, 72 relative to the EM field generator 21. The control unit 50 receives the signals, which respectively indicate the positions of the sensors 70, 72 relative to the identifier 20. The control unit 50 uses the two positions, which are measured relative to the same reference, the identifier 20, to calculate the position of the second sensor 72 relative to the first sensor 70.

When the second sensor 72 is aligned along the axis 14, the orientation of the second sensor 72 indicates the position of the impaction axis 14. Thus the control unit 50 records the position of the second sensor 72 as the position of the axis 14. When the second sensor 72 is oriented at a different known position relative to the axis 14, the control unit 50 calculates the position of the axis 14 using the known offset between the position of the second sensor 72 and the axis 14. The control unit 50 records the calculated position of the axis 14 relative to the first sensor 70.

The control unit 50 can also calculate and store the position of the center of rotation point 15 and a location on the surface of the acetabulum 13 relative to the first sensor 70. Because the second sensor 72 is located at a known position relative to the guide 60, the control unit 50 can access known offsets between the position of the second sensor 72 and the location of the center of rotation point 15 and the location of the surface of the acetabulum 13 to determine their locations relative to the sensor 70. The control unit 50 can display an indication 14' of the position of the axis 14 relative to the joint 10.

In the implementations illustrated in both FIGS. 4A and 4B, the control unit 50 can determine and store a rotational position about the impaction axis 14. For example, the portion 66 of the guide 60 that engages either the end 31 of the instrument 30 or the second sensor 72 can include a keyway or notch that permits alignment in limited number of rotational positions, for example, a single position, about the impaction axis 14. Alternatively, the guide 60 can include markings that indicate a particular rotational position.

The surgeon positions the instrument 30 or the second sensor 72 in the known rotational alignment indicated by the guide 60. As a result, the position of the identifier 20 relative to the sensor 70 (FIG. 4A) or the position of the second sensor 72 relative to the sensor 70 (FIG. 4B) corresponds to the known rotational position.

1.3 Orienting Instruments

After the surgeon uses the control unit 50 to determine the position of the impaction axis 14 relative to the first sensor 70, the surgeon removes the guide 60 from the joint 10, exposing the acetabulum 13. As the surgeon positions the instrument 30 relative to the joint 10, the system 100 assists the surgeon to orient instruments 30 relative to the impaction axis 14. For example, the system 100 can indicate changes to the current orientation of a reamer that would result in the reamer being positioned along the impaction axis 14. Thus the system 100 assists the surgeon to position the reamer along the impaction axis 14 while the surgeon prepares the acetabulum 13, for example, by removing cartilage and bone. The system 100 can also indicate the alignment of an impaction tool for driving an acetabular implant into the prepared acetabulum 13.

Figure 5A:
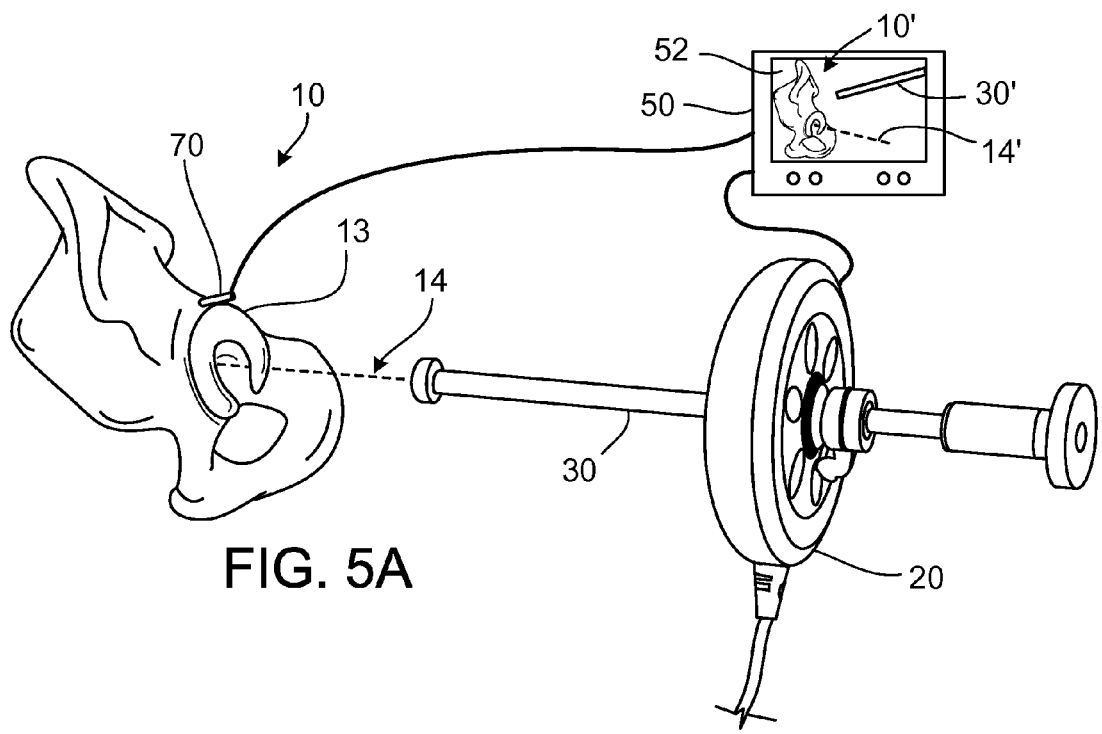
FIGS. 5A and 5B are perspective views illustrating techniques for calculating the position of an instrument relative to an axis.
Figure 5B:
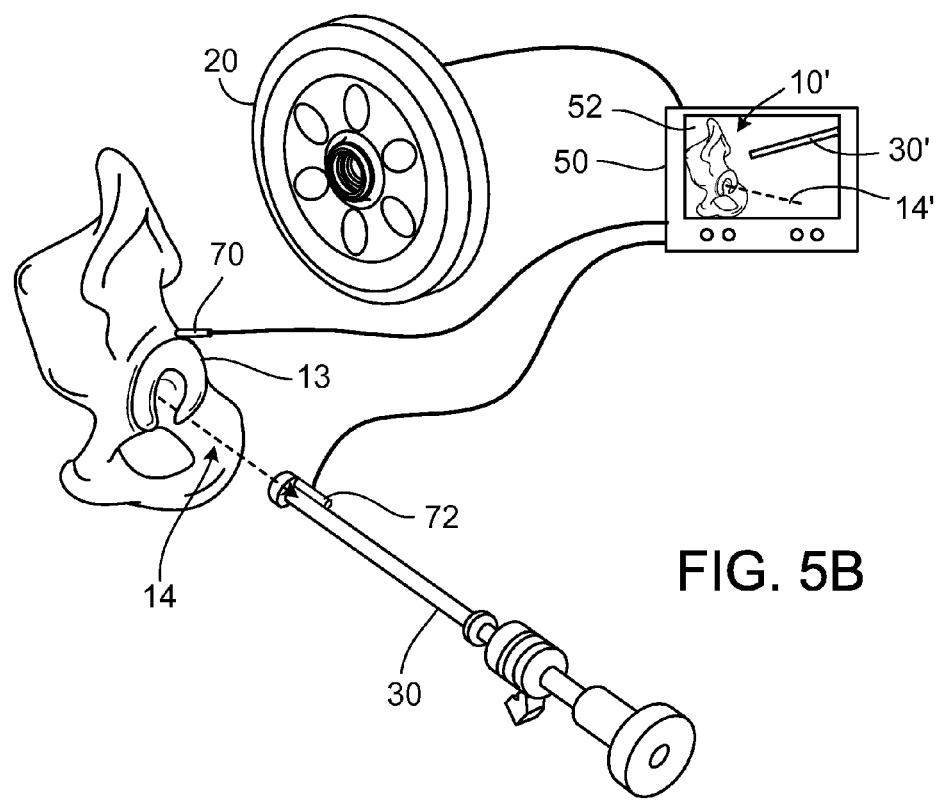

FIGS. 5A and 5B illustrate alternative techniques for determining the current alignment of the instrument 30 relative to the joint. Either of the alternative techniques shown in FIGS. 5A and 5B can be used with either of the techniques shown in FIGS. 4A and 4B for determining the position of the impaction axis 14. The position of the instrument 30 can be determined, for example, using the position of an identifier 20 when coupled to the instrument 30 (FIG. 5A), or using the position of an EM field sensor coupled to the instrument 30 (FIG. 5B).

Referring to FIG. 5A, the surgeon positions the instrument 30 while the identifier 20 is coupled to the instrument 30. The identifier 20 is attached at a fixed position relative to instrument 30 so that the identifier 20 and the instrument 30 move together. If the technique of FIG. 4A is used to determine the position of the impaction axis 14, the identifier 20 can remain attached at the same position of the instrument 30 that was used to measure the position of the impaction axis 14. In some implementations, the surgeon can couple the identifier 20 about the instrument 30 at a known position of the instrument 30.

The surgeon moves the instrument 30 near the acetabulum 13, and the sensor 70 detects EM fields from the identifier 20 attached to the instrument 30. The output of the sensor 70 indicates the relative position of the sensor 70 and the identifier 20, which the control unit 50 uses to calculate the position of the instrument 30 relative to the sensor 70. As the surgeon moves the instrument 30 into alignment relative to the acetabulum 13, signals from the sensor 70 vary to reflect its changing position relative to the identifier 20. The control unit 50 uses the sensor signals to calculate the positions of the instrument 30 as the instrument 30 moves relative to the acetabulum 13.

Referring to FIG. 5B, as an alternative technique, the surgeon couples the second sensor 72 to the instrument 30 at a known, fixed position of the instrument 30. For example, the second sensor 72 can be attached at a landmark of the instrument 30, such as a portion of the instrument 30 that receives the second sensor 72. In some implementations, the second sensor 72 has a known rotational position. For example, the surgeon can attach the second sensor 72 such that the instrument 30 receives the second sensor 72 at a rotational position that is known relative to the instrument 30.

The surgeon brings the instrument 30 near the acetabulum 13, causing the sensors 70, 72 to be brought within the working volume of the EM field generator 21 of the identifier 20. The control unit 50 receives signals from the sensors 70, 72 indicating their respective positions relative to the identifier 20. Using the known position of the instrument 30 relative to the second sensor 72, and the positions of the sensors 70, 72 known relative to the identifier 20, the control unit 50 calculates the position of the instrument 30 relative to the first sensor 70. To position a second instrument relative to the joint 10, the surgeon places the sensor 72 at a known position relative to the second instrument.

In some implementations, rather than attaching the second sensor 72 to the instrument, the surgeon can couple a different sensor to the instrument 30. In some implementations, a third sensor and the second sensor 72 can be calibrated prior to the surgery. The control unit 50 can store information indicating the calibrations of the sensors, or each sensor can include calibration data stored on a storage device.

The techniques of FIGS. 5A and 5B permit the control unit 50 to calculate the current position of the instrument 30 relative to the sensor 70. Because the position of the impaction axis 14 is determined relative to the sensor 70, the control unit 50 can compare the current position of the instrument 30 with the position of the impaction axis. As the position of the instrument 30 changes, the control unit 50 receives updated signals from the sensor(s) 70, 72 and recalculates the position of the instrument 30 relative to the axis 14.

Figure 6:
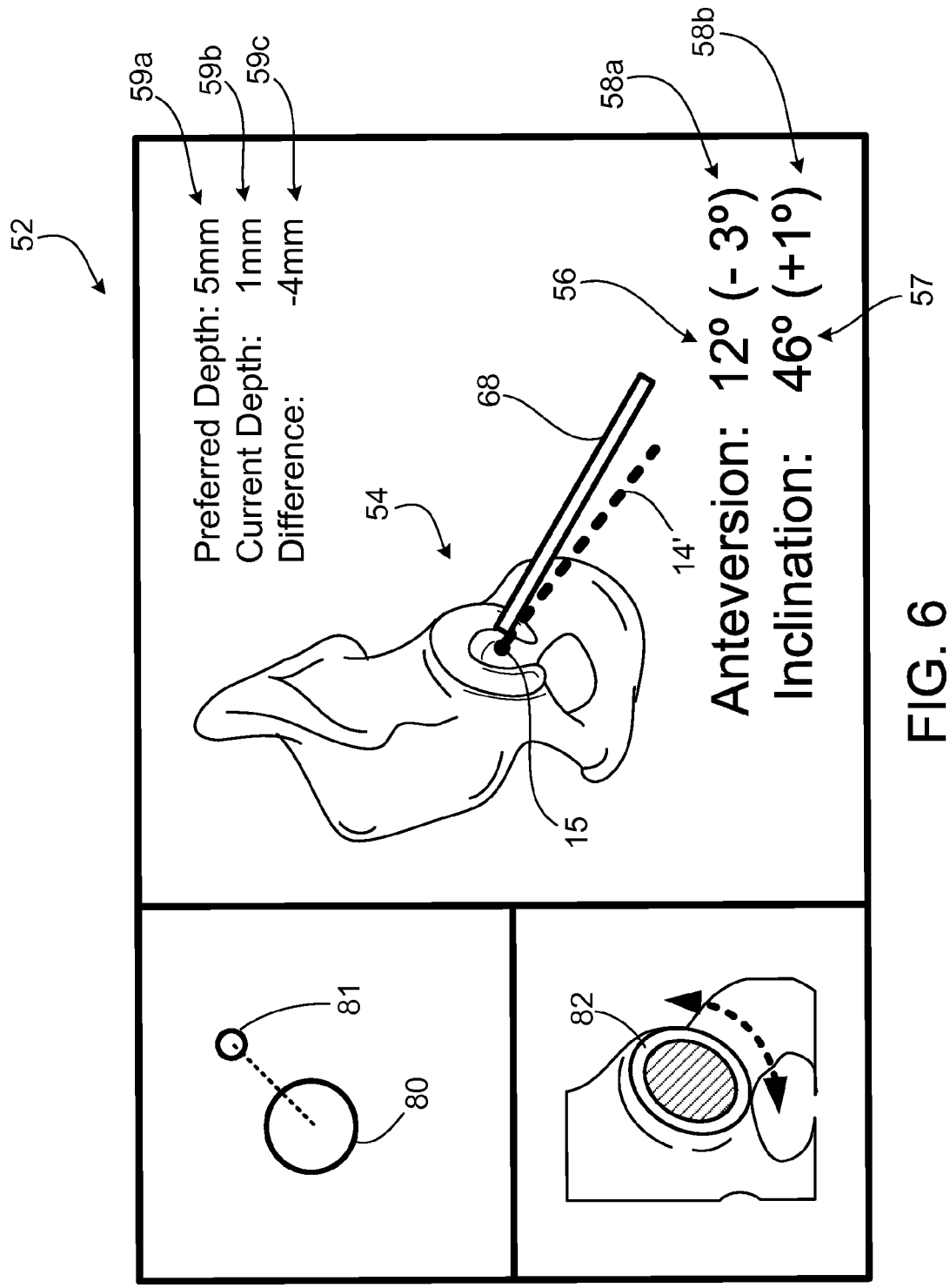
FIGS. 6, 7A, and 7B are illustrations of user interfaces of a control unit of the system of FIG. 1.

Referring to FIG. 6, the control unit 50 indicates the position of the instrument 30 on the user interface 52. The control unit 50 indicates the alignment of the instrument 30 relative to the axis 14, for example, indicating differences between the current position of the instrument 30 and the position of the impaction axis. During reaming of the acetabulum 13 and impaction of the acetabular shell, the reamer and impactor are properly aligned when they are collinear with the impaction axis 14.

As an example, when the identifier 20 remains coupled at the same position of the instrument 30 as in FIG. 4A, the position of the identifier 20 corresponding to the former physical alignment with the guide 60 is the position in which the instrument 30 is aligned along the impaction axis 14. Returning the instrument 30 and the identifier 20 to the former position aligns the instrument 30 along the impaction axis 14.

In a similar manner, when the second sensor 72 is used to determine the position of the impaction axis 14 as shown in FIG. 4B, and the second sensor 72 remains coupled at the same position of the instrument 30 in FIG. 5B, the instrument 30 is aligned along the impaction axis 14 when second sensor 72 returns to the same position relative to the first sensor 70 that was previously recorded. Thus the control unit 50 can assist the surgeon to align the instrument 30 along the impaction axis 14 by comparing (i) the current position of the second sensor 72 relative to the first sensor 70 with (ii) the previously recorded position of the second sensor 72 relative to the first sensor 70. The variance of the current position from the recorded position indicates the variance of the instrument 30 from the impaction axis 14.

The control unit 50 can display a three-dimensional illustration 54 (e.g., rendering) of the joint 10. For example, the control unit 50 can access the imaging data 55, and can display, for example, a tomography image or other illustration of the joint 10 based on the imaging data 55. The position of the impaction axis 14 determined relative to the first sensor 70 can be positioned to coincide with the position of the impaction axis 14 as indicated in annotations to the imaging data 55. When a rotational position about the impaction axis 14 is known relative to the first sensor 70, the known rotational position can be used to further orient the imaging data 55 in the coordinate reference system of the first sensor 70. Alternatively, locations of one or more anatomical landmarks can be measured relative to the first sensor 70, by contacting the anatomical landmarks with the end 31 of the instrument 30 or a probe. The control unit 50 uses the measured positions of the landmarks to represent corresponding positions of the joint 10 indicated in the imaging data 55.

If imaging data 55 is not accessible, a generic illustration of a hip joint can be displayed, aligned to the coordinate system of the first sensor 70 in the same manner described for imaging data 55.

The illustration 54 can be a visualization of the operation site from an approximate angle that the surgeon is expected to view the operation site, so that the illustration 54 corresponds to the surgeon's view of the acetabulum 13 of the patient. The viewing angle for the illustration 54 can be an orientation looking down the impaction axis 14.

Relative to the illustration 54, the control unit 50 indicates the position of the impaction axis 14 relative to the joint 10 and one or more markers 68 indicating the current alignment of the instrument 30. The control unit 50 can also display an indication of acceptable positioning when the instrument 30 is aligned within a particular tolerance of the axis 14 and display an indication of unacceptable positioning when the instrument 30 is positioned outside the tolerance.

The control unit 50 can also display, for example, indications of differences between the alignment of the instrument 30 and the trajectory of the impaction axis 14. For example, the control unit 50 displays information indicating a translational offset and angular deviation of the instrument 30 from the axis 14. The control unit 50 can display a marker 80, such as a circle, that represents alignment along the axis 14, and a second marker 81 or circle indicating the position of the instrument 30. The position at which the two markers 80, 81 coincide can correspond to alignment of the instrument 30 along the axis 14.

The control unit 50 can also display the inclination angle 56 and the anteversion angle 57 of the impaction axis 14.

The cup inclination angle and the cup anteversion angle that would result from impaction at the current position, if different, can additionally or alternatively be displayed. The control unit 50 calculates and indicates differences between the current position of the instrument 30 and the impaction axis 14, for example, with numerical indications 58a, 58b of deviations from the inclination angle and anteversion angle of the impaction axis. Alternatively, the control unit 50 can display the absolute inclination angle and anteversion angle of the instrument 30, rather than as a difference from a preferred inclination angle and anteversion angle.

The inclination angle 56 and anteversion angle 57 of the impaction axis 14 can be determined using the imaging data 55 for the joint 10, resulting in the position of the impaction axis 14 being known relative to relative to anatomical reference axes. The impaction axis 14 defined by the guide 60 is the same impaction axis 14 measured by the control unit 50, and thus has the same inclination angle and anteversion angle determined using the imaging data 55. Deviations of the instrument 30 from the axis 14 thus indicate deviations from the known inclination angle and anteversion angle of the axis 14, allowing the control unit 50 to determine the absolute inclination and anteversion angles of the instrument 30. The control unit 50 can display the inclination and anteversion angles of the instrument 30 and of the impaction axis 14, which indicates the preferred alignment. To meet the needs of the patient, the surgeon can also adjust the preferred impaction axis to be different from the axis 14 indicated by the guide 60.

The control unit 50 can display a view of the joint with an image 82 of an implant in place in the acetabulum 13. As the surgeon moves the instrument 30, the control unit 50 moves the image 82 of the implant relative to the joint 10, showing the position of the implant that would result if reaming or impaction were performed at the current position of the instrument 30. The surgeon can input information identifying the acetabular implant to be installed, such as a part number for the implant. The control unit 50 can use the received information to access a model of the implant to generate the image.

The control unit 50 also displays information to assist the surgeon in achieving the preferred depth for reaming of the acetabulum 13. A preferred reaming depth 59a, a current reaming depth 59b, and a difference 59c between the two depths 59a, 59b can also be indicated on the user interface 52. The control unit 50 can determine the preferred reaming depth 59a based on the known position of the center of rotation point 15 of the joint 10 and based on accessed information indicating the characteristics of acetabular implant to be installed. The accessed information can indicate, for example, the dimensions of a particular acetabular implant, such as the thickness of the implant, and the position of the center of rotation of the implant. The control unit 50 calculates the preferred reaming depth 59a such that, with proper acetabular shell impaction, the installed acetabular implant will have a center of rotation that coincides with the original center of rotation of the joint 10 or that has a specific offset determined by the surgeon.

As an alternative, the control unit 50 can determine the preferred reaming depth 59a based on the known position of the surface of the acetabulum 13 and the thickness of the acetabular implant. In addition, the preferred reaming depth 59a can be selected as a depth within a particular range. The minimum depth can be set to ensure that the acetabular implant can enter the acetabulum 13 sufficiently to be firmly anchored, and the maximum depth can be set to prevent causing the medial wall of the pelvis to become excessively thin.

The end 31 of the instrument 30, for example, the apex of a reamer, can have a known position relative to the reference coupled to the instrument 30, and the known position can be input to the control unit 50. Thus the control unit 50 can track the position of the end 31 of the instrument 30 during reaming and other procedures.

As reaming proceeds, the control unit 50 can refresh the user interface 52 to reflect the updated reaming depth information. In some implementations, the center of rotation point 15 can be displayed with an indicator 53 that indicates the center of rotation point that would be achieved if reaming terminated at the current position. As reaming continues, the indicator 53 advances toward and eventually reaches the displayed center of rotation point 15, indicating that the proper reaming depth has been achieved. Thus the system 100 assists the surgeon to achieve the preferred reaming depth, and indicates when reaming is incomplete or is excessive.

Figure 7A:
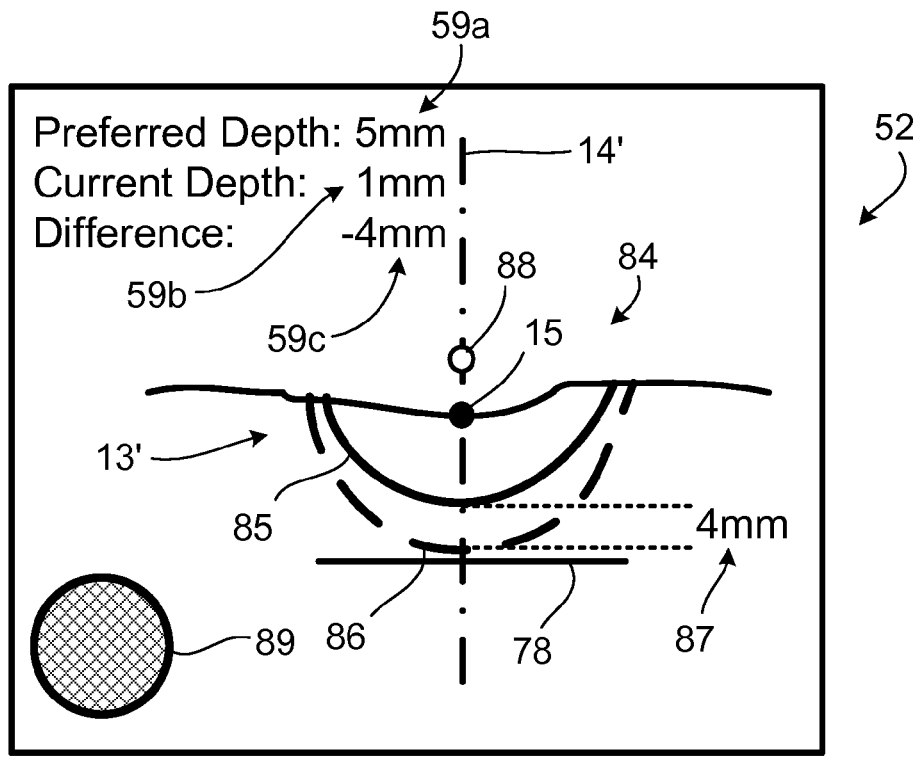

Referring to FIG. 7A, the control unit 50 can display on the user interface 52 a side view 13' of the acetabulum 13, for example, a view perpendicular to the impaction axis 14 (e.g., a cut-away view). The user interface 52 can display an image 84 showing the current surface 85 of the acetabulum 13 and the desired surface 86 after reaming, as well as the distance 87 that reaming must continue to reach the desired position. The control unit 50 can also display an indication 78 of a stop plane that indicates a maximum reaming distance, beyond which harm to the patient may occur.

The control unit 50 can also calculate and display the position of the center of rotation point 15 and a center of rotation point 88 that would result from installation of a selected acetabular implant at the current reaming depth.

The user interface 52 can also show one or more colored indications 89 on the user interface 52 to indicate the amount of reaming that is needed. For example, the user interface can display a green symbol to indicate reaming should continue, a blue symbol to indicate that reaming is close to or at the desired position, or a red symbol to indicate that reaming should be stopped, for example, because the desired depth is reached or exceeded, or because the reamer is out of alignment.

The surgeon can indicate on the user interface 52 when reaming is complete. The control unit 50 can identify, based on the final reaming depth reached, a suggested acetabular implant and a suggested neck length for a femoral implant that can be used to achieve match the original position of the joint center of rotation point 15.

Figure 7B:
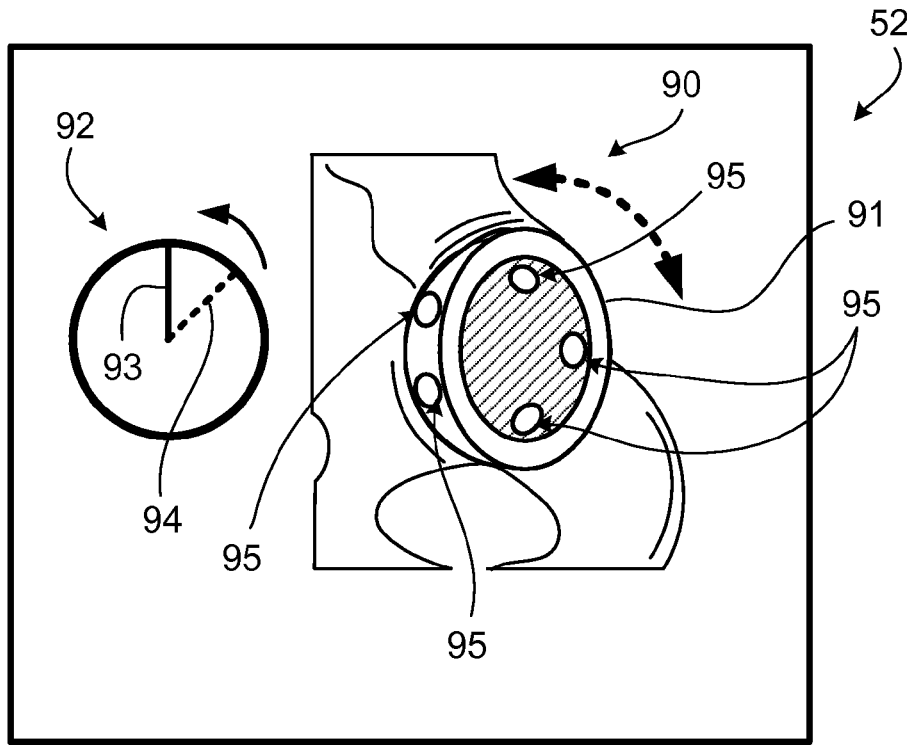

Referring to FIG. 7B, in some implementations, the control unit 50 determines the rotational position of the instrument 30 relative to desired rotational position. For example, when aligning the impactor to install the acetabular implant, the control unit 50 can display an image 90 of the joint 10 with an image 91 of the acetabular implant to be installed. The control unit 50 can display an indicator 92 that indicates a preferred rotational position 93 and the current rotational position 94 of the instrument 30.

As described above, the position of the identifier 20 or second sensor 72 can have a known rotational orientation about the impaction axis 14 when used to measure the position of the impaction axis 14 using the guide 60. This rotational position, for example, a standard position relative to anatomical references, can be determined relative to the patient's anatomy using the imaging data 55 at the time the guide 60 is formed. The control unit 50 accesses information indicating the standard rotational position relative to the anatomy of the patient. The control unit 50 also accesses information indicating characteristics of the acetabular implant to be installed, for example, the positions of holes 95 in the implant through which screws can be inserted to anchor the implant to the pelvis.

Using the information indicating the standard rotational position and known characteristics of the pelvis, the control unit 50 calculates a preferred rotational position about the impaction axis 14 that will align the holes 95 with pelvic bone thick enough to form a stable connection with screws. Alternatively, the control unit 50 can access information indicating a pre-calculated preferred rotational position. The control unit 50 compares the current rotational position of the instrument 30 with the preferred rotational position, and updates the user interface 52 to indicate changes in position needed to reach the preferred rotational position.

Using the indications displayed on the user interface 52 illustrated in FIGS. 6, 7A, and 7B, the surgeon completes the surgical procedure. Because the guide 60 has been removed from the joint 10, the surgeon has access to the entire acetabulum 13. Because the control unit 50 indicates the position of the impaction axis 14 in the absence of the guide 60, the surgeon retains the ability to align instruments 30 relative to the axis 14. For example, the surgeon aligns a reamer relative to the impaction axis 14 and prepares the acetabulum 13 to receive the acetabular implant, for example, by removing the cartilage of the acetabulum 13 and reaming to a preferred depth, as indicated on the user interface 52. The surgeon may also use the system 100 to align an impaction instrument along the impaction axis 14 and drive the acetabular implant into position along the impaction axis 14.

The techniques described can be used to determine alignments for joints other than hip joints, for example, shoulder joints. As an example, a guide substantially conforming to a glenoid cavity can be used to determine the position of a surgical alignment relative to a scapula. The system 100 can be used to indicate alignments relative to the scapula as described above.

2. Alignment Using Data for Multiple Joints

A surgeon can use the system 100 to determine a surgical alignment for a joint relative to anatomical axes of a patient, without using imaging data for the joint to be operated on. The position of a surgical axis having a known alignment relative to the patient's anatomy can be identified based on data about joints of multiple individuals. For example, a database can store joint data indicating characteristics of a set of multiple joints and positions of surgical alignments at known positions relative to the respective joints. Correlations between the stored joint data and data for a joint not in the set can be used to determine a position corresponding to a particular inclination angle and anteversion angle for the joint not in the set.

For joints of the same type, for example, hip joints of different patients, the ranges of motion of the joints can have similar characteristics. For example, a region generally corresponding to the limits of the range of motion of a hip joint can have a characteristic shape. Thus representations of the ranges of motion of different hip joints can indicate similar shapes and corresponding features.

Data can be acquired for a set of joints including data describing a range of motion of each joint in the set. One or more alignments, such as an axis having a known inclination angle and anteversion angle, can be determined for each joint in the set. The position of the axis relative to the range of motion of each joint can be determined and stored.

Relationships between ranges of motion for different joints can be determined based on commonalities among the ranges of motion. For example, joint data describing a first range of motion for a first joint can be compared with joint data describing a second range of motion of different, second joint. When the position of an axis having a particular inclination angle and a particular anteversion angle is known relative to the first range of motion, a corresponding position having the same inclination angle and the same anteversion angle can be determined relative to the second range of motion.

Using the stored data, a surgical alignment can be determined for a different joint 10 that is not described in the stored data. The range of motion for the joint 10 is measured, and control unit 50 compares the measured range of motion with the stored ranges of motion of joints described in the database. Based on commonalities between the measured range of motion for the joint 10 and the stored ranges of motion for other joints, the control unit 50 selects an impaction axis for the joint 10 that corresponds to the position of impaction axes for the other joints relative to their ranges of motion. For example, stored data can indicate the position of an axis having an inclination of 45 degrees and an anteversion of 15 degrees relative to the respective ranges of motion for multiple joints. The stored joint data can be used to identify, for the joint 10, an axis having the same inclination angle and anteversion angle, using information about the range of motion of the joint 10.

By calculating a surgical alignment for a joint using stored joint data, the surgical alignment can often be determined quickly and without requiring imaging data for the joint. A patient does not incur the cost of imaging the joint, and avoids radiation exposure that would accompany a CT scan. The surgical alignment can also be determined without a customized guide and without requiring a surgeon to manually identify anatomical references of the acetabulum.

Examples of acquiring joint data, analyzing the data, and using the data to align instruments during surgery are described below.

2.1 Acquiring Joint Data

The system 100 can be used to acquire joint data that can be used to assist surgeons in later procedures. As an example, the system 100 can be used to acquire data about the impaction axes for multiple hip joints, which can be included in a database of hip joint data. In some implementations, hip joint data is acquired through measurements of hip joints using patient-specific guides.

Figure 8:
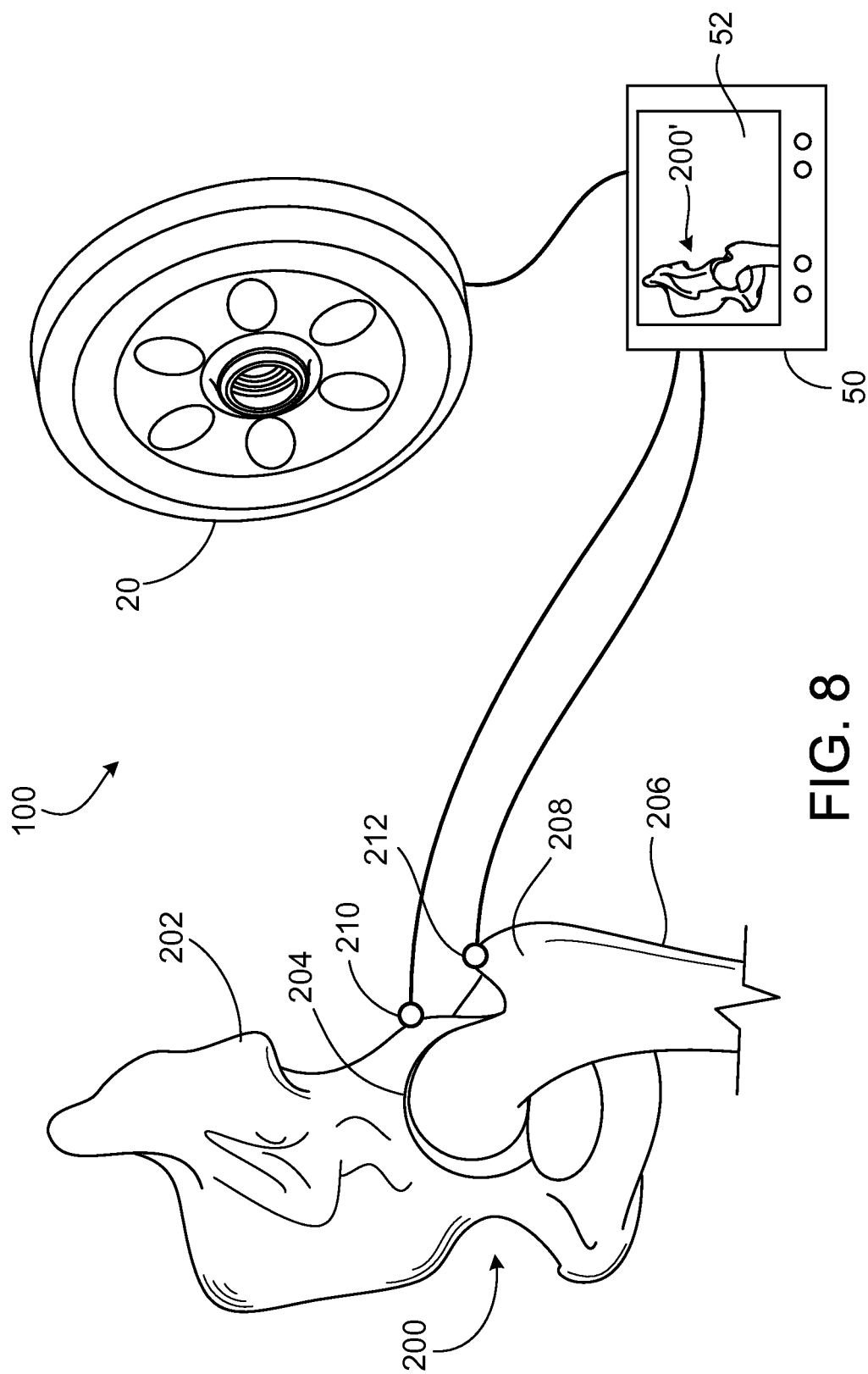

Referring to FIG. 8, a joint 200 to be described in the database is illustrated. The system 100 acquires information about the range of motion of the joint 200. A surgeon establishes two references, moveable relative to each other and located at fixed positions relative to the joint 200. For example, the surgeon implants a first EM field sensor 210 and a second EM field sensor 212 at different fixed positions relative to the joint 200. The first sensor 210 is attached to the pelvis 202, outside the acetabulum 204, and moves with the pelvis 202. The second sensor 212 is attached to the femur 206, for example, at the tip of the greater trochanter 208 of the femur 206, and moves with the femur 206. As a result, movement of the femur 206 relative to the pelvis 202 causes the sensors 210, 212 to move relative to each other.

The surgeon positions the identifier 20 such that both of the sensors 210, 212 are within the working volume of the EM field generator 21. The control unit 50 receives signals from the sensors 210, 212 that indicate the positions of the sensors 210, 212 relative to the field generator 21. The control unit 50 can display information, such as a representation 200' of the joint 200, on the user interface 52.

Figure 9:
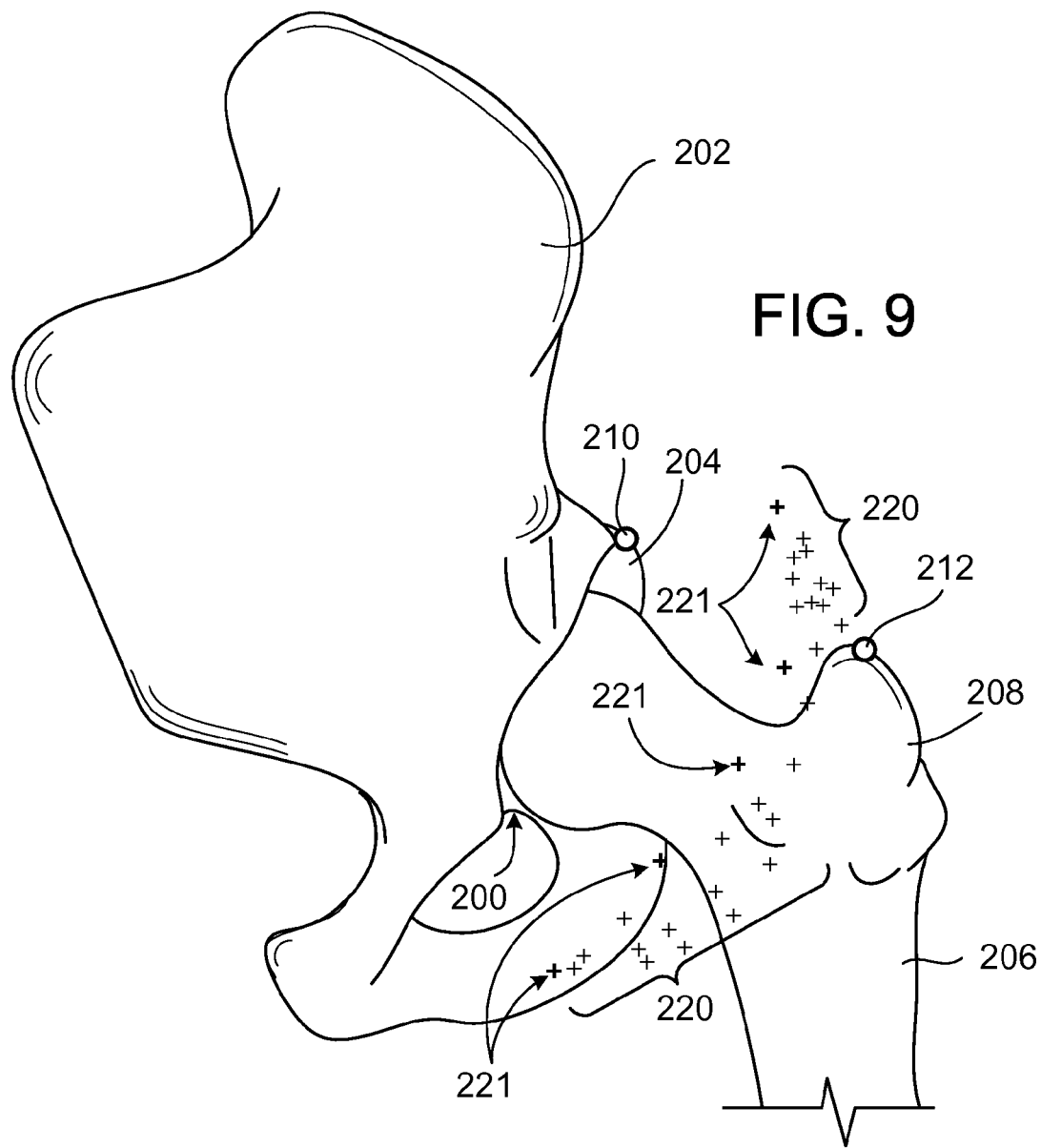

Referring to FIG. 9, the surgeon moves the joint 200 through a range of motion. At multiple different positions of the joint 200, the control unit 50 records the relative locations of the sensors 210, 212. Because the positions of the sensors 210, 212 are known relative to the same reference, the identifier 20, the control unit 50 can determine the locations of the sensors 210, 212 relative to each other. The control unit 50 can designate the first sensor 210 as a fixed point of reference, for example, and can record the different measured locations of the second sensor 212 relative to the first sensor 210. The recorded locations can be represented by points 220 that indicate the position of the second sensor 212 relative to the first sensor 210 in a three-dimensional coordinate system. The positions of the joint 200 and the points 220 can be displayed or otherwise indicated on the user interface 52.

The control unit 50 records different locations of the sensors 210, 212 relative to each other, each corresponding to different positions of the joint 200. The control unit 50 can record the positions while the sensors 210, 212 are in motion or while the sensors 210, 212 are stationary. The surgeon can manually engage a control that causes the control unit 50 to record a current position of the sensors 210, 212. Alternatively, the control unit 50 can automatically record different locations of the sensors 210, 212 at different positions of the joint 200, for example, at defined time intervals or after a change of position is detected.

The movement of the joint 200 by the surgeon through the range of motion can include movement to positions at or near extremities of the range of motion of the joint 200. The control unit 50 records one or more locations of the sensors 210, 212 corresponding to positions of the joint 200 at or near the extremities of the range of motion. Thus the recorded points 220 can include outlying points 221 that substantially correspond to positions of the joint 200 at the extremities of the range of motion of the joint 200. For example, the outlying points 221 can correspond to positions such that the limits of the range of motion can be approximated using the outlying points 221. The control unit 50 can identify the outlying points 221, and interpolate linear or curved segments between the outlying points 221 to define a path substantially corresponding to the limits of the range of motion in three-dimensions.

In some implementations, points 220 that correspond to one or more key positions of the joint 200 are recorded. The control unit 50 can record one or more positions of the sensors 210, 212 substantially corresponding to an extremity of one or more of, for example, hip flexion, hip extension, hip hyperextension, hip abduction, hip adduction, hip lateral rotation, and hip medial rotation.

Referring to FIGS. 10A to 10C, the control unit 50 generates a representation based on the points 220. For example, the representation can indicate features of a three-dimensional surface that approximates the locations of the points 220. As used herein, a representation can be a data structure. A representation may be, but need not be, capable of being rendered for visual display. To calculate the surface, the control unit 50 can use data-fitting techniques (e.g., curve-fitting or non-linear regression techniques), such as ordinary least squares or total least squares algorithms, to calculate a surface interpolated between and/or extrapolated from the points 220.

For example, the surface generated based on the points 220 can be a sphere 230 about the joint 200, calculated to extend through regions spanned by the points 220. The control unit 50 can generate the sphere 230 by applying curve-fitting techniques to the points 220 to select parameters including (i) the position of a center point 232 of the sphere 230 and (ii) a radius of the sphere 230. The sphere 230 is thus a data fitting extrapolated from the points 220, and need not be an optimal or exact fit to the points 220. The center point 232 corresponds to the center of rotation of the joint 200.

The control unit 50 calculates a range of motion surface 234 that approximates a region spanned by the points 220. The surface 234 can approximate a region spanned by all or substantially all of the points 220. In other words, for substantially all of the recorded points 220, a linear axis through the center point 232 and a particular point 220 intersects the surface 234. The surface 234 can be substantially bounded by the outlying points 221. The surface 234 can be a portion of the sphere 230, and can have boundaries 237 that approximate the outlying points 221. Thus, the boundaries 237 can substantially correspond to the limits of the recorded locations of sensor 212 during movement of the joint 200 through its range of motion, with the boundaries 237 forming a trace or path approximating the limits of the movement of the sensor 212. A surface such as the surface 234 that indicates characteristics of a range of motion of a joint is referred to herein as a range of motion surface for a joint.

Because the locations of the points 220 are measured relative to the first sensor 210, the position of the surface 234, the sphere 230, and the center point 232 are known relative to the first sensor 210. The control unit 50 can indicate positions of the calculated surface 234, the sphere 230, the measured points 220, and the center point 232 relative to each other on the user interface 52.

Figure 11A:
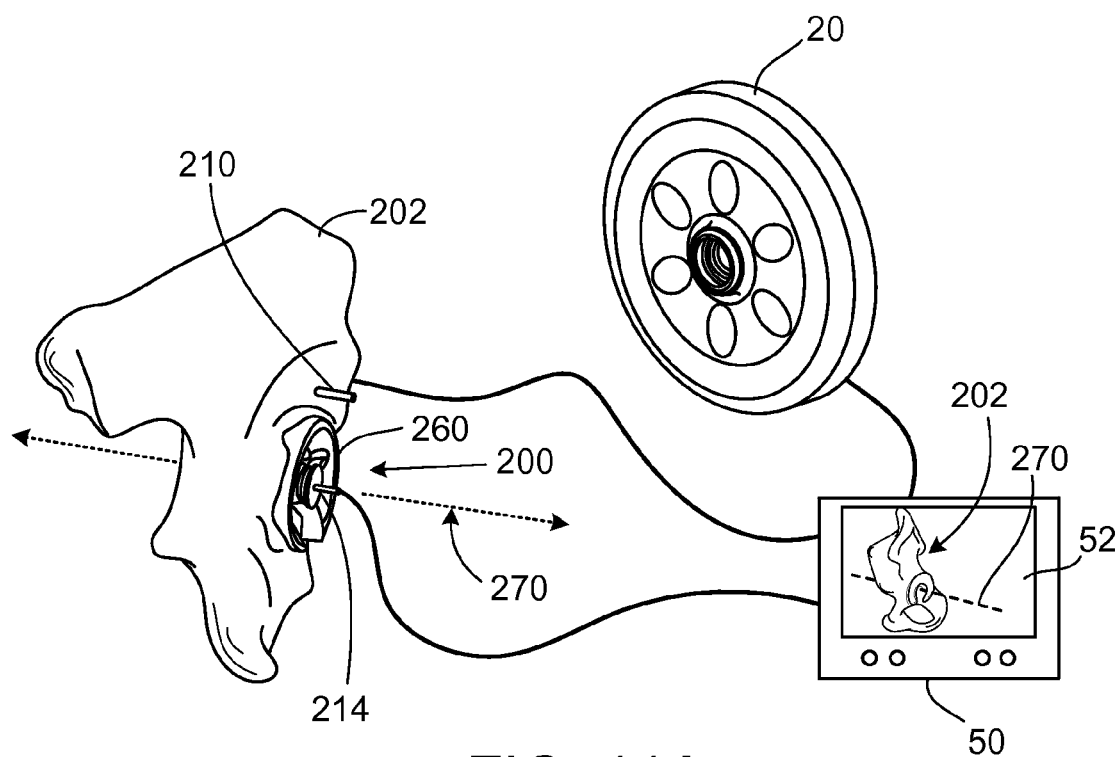

Referring to FIG. 11A, the surgeon dislocates the joint 200 and inserts a custom guide 260 into the acetabulum 204. The guide 260 is pre-operatively formed to substantially conform to the acetabulum 204 based on pre-operative imaging data for the joint 200. The guide 260 indicates a position of an impaction axis 270 for the joint 200. The impaction axis 270 has a known inclination angle and a known anteversion angle, determined relative to the patient's anatomy based on imaging data for the joint 200. For example, the guide 260 can indicate the position of the impaction axis 270 such that, when the guide 260 mates with the joint, the impaction axis 270 has an inclination angle of 15 degrees and an anteversion angle of 45 degrees, or another known inclination angle or anteversion angle.

While the guide 260 is in place in the joint 200, the identifier 20 is used to determine the position of the impaction axis 270 indicated by the guide 260. For example, the alignment of the impaction axis 270 is determined relative to the previously implanted first sensor 210 using a third sensor 214 aligned along the impaction axis 270, using the techniques described above with respect to FIG. 5B. Alternatively, the identifier 20 is aligned relative to the impaction axis 270, as described with respect to FIG. 5A.

Alternatively, the impaction axis 270 of the joint 200 can be determined using other techniques that do not require a guide 260, for example, using the techniques with reference to FIGS. 21A and 21B.

Figure 11B:
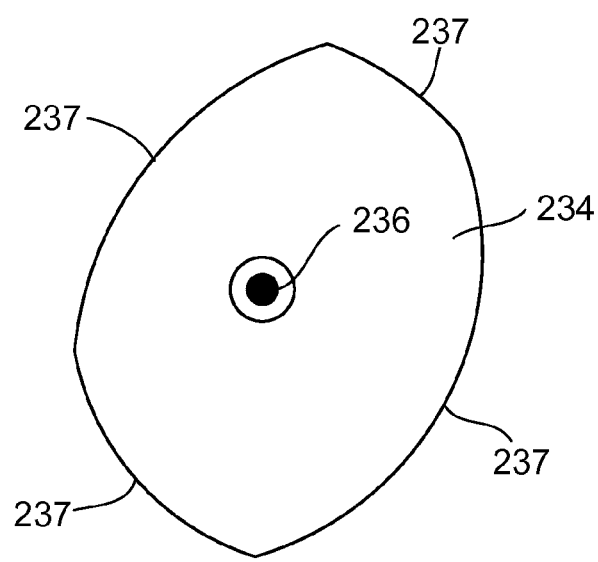

Referring to FIG. 11B, the control unit 50 determines a location of an intersection point 236 where the impaction axis 270 intersects the surface 234. As described above, the control unit 50 determined the position of the surface 234 and the position of the impaction axis 270 relative to the same reference, the first sensor 210. Thus the control unit 50 can calculate the location of the intersection point 236, which indicates the position of the impaction axis 270 relative to the surface 234, with reference to the first sensor 210.

The control unit 50 records data indicating characteristics of the surface 234, for example, data describing the shape of the boundaries 237 and the curvature of the surface 234. The control unit 50 can also record data indicating the radius of the sphere 230 and the location of the center point 232 of the sphere 230 relative to the surface 234. The control unit 50 also records data indicating the location of the intersection point 236 relative to the surface 234. The center point 232 and the intersection point 236 together define the impaction axis 270, and thus indicate the position of the impaction axis 270 relative to the surface 234. The control unit 50 also records the inclination angle and the anteversion angle of the impaction axis 270.

The measurements and calculations described for the joint 200 can be repeated for hip joints of different patients. In some implementations, as data for different joints is acquired, the reference located at the femur can be placed at a generally consistent position to facilitate comparison of data from different hip joints. For example, the reference can be consistently placed at the tip of the greater trochanter of the femur. The reference can alternatively be placed at another anatomical location, for example, at a different portion of the greater trochanter, at a particular portion of the femoral neck, or at or near the lesser trochanter.

Regardless of the position of the sensor located at the pelvis, the range of motion surface has a generally comparable shape. The position of the sensor located at a fixed location relative to the pelvis may vary from one joint to another without affecting the comparability of the recorded data.

2.2 Analyzing Acquired Data

Figure 12A:
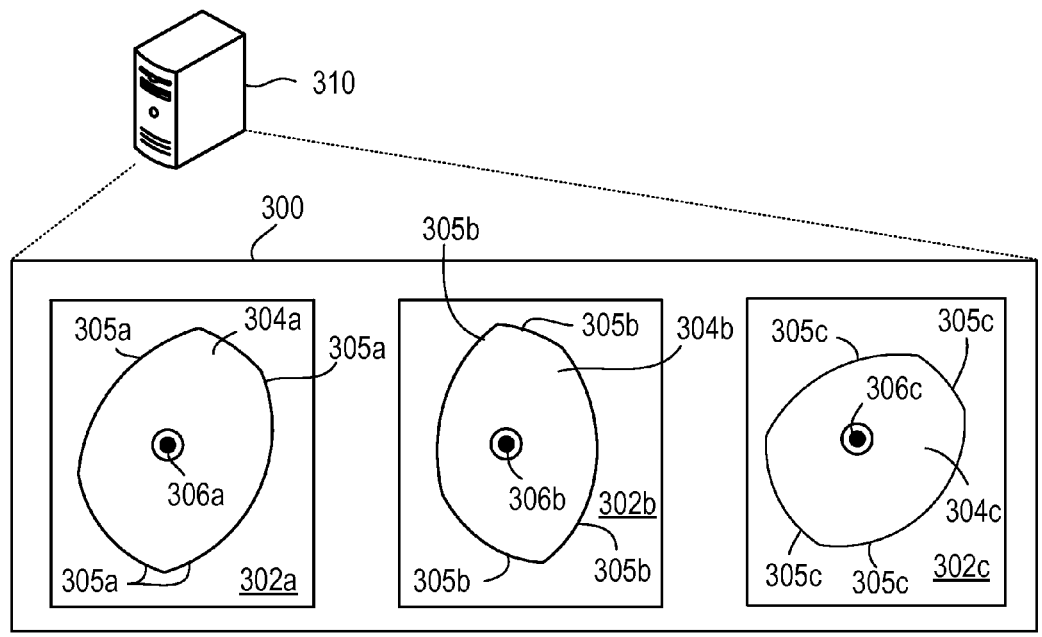
FIGS. 12A to 12C and 13 are illustrations of a process for processing data for multiple joints.

Referring to FIG. 12A, a computer system 310, which may or may not include the control unit 50, accesses data describing multiple joints from one or more storage devices. For example, the computer system 310 can access a database 300 that stores data describing different hip joints. For simplicity, the data for each joint is referred to as a record. Nevertheless, the data need not be stored in any particular format and may be stored in any appropriate data structure or storage system. Data for multiple joints may be stored in a single data structure, and data for a single joint may be distributed across many different data structures.

The database 300 stores multiple records 302a-302c that each describes characteristics of a different joint. The records 302a-302c can thus include information about different hip joints of different individuals. Each record 302a-302c describes (1) a range of motion for a hip joint and (2) the position of one or more alignments, such as one or more impaction axes, for the hip joint relative to the range of motion.

Each record 302a-302c can describe a three-dimensional range of motion surface 304a-304c for a hip joint and the location of an intersection point 306a-306c. The intersection point 306a-306c can indicate the location that an impaction axis intersects the corresponding surface 304a-304c. In some implementations, each record 302a-302c can also indicate the location of a center point corresponding to the center of rotation of the corresponding hip joint. Alternatively, the center of rotation points for the hip joints can be calculated from the range of motion surfaces 304a-304c. Each record 302a-302c can also indicate the inclination angle and anteversion angle for the impaction axis defined by the intersection point 306a-306c and the corresponding center point.

In some implementations, the impaction axes represented by the intersection points 306a-306c can have the same inclination angle and the same anteversion angle. For example, each intersection point 306a-306c can indicate a location corresponding to the intersection of an axis having, for example, an inclination angle of 45 degrees and an anteversion angle of 15 degrees for the corresponding hip joint.

Figure 12B:
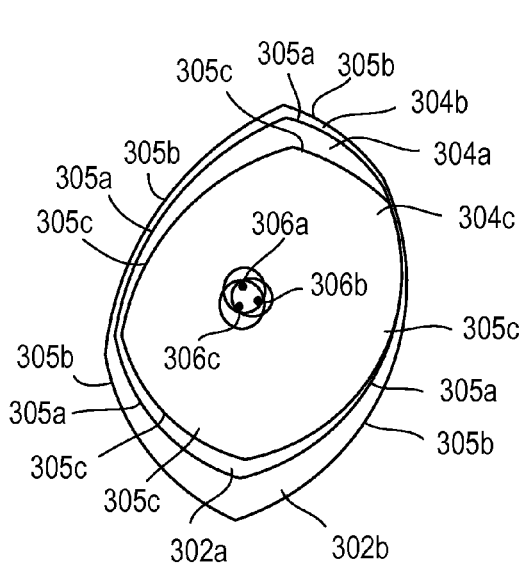

Referring to FIGS. 12A and 12B, the computer system 310 identifies relationships between the joint data in the records 302a-302c. For example, the computer system 310 identifies correlations between the ranges of motion of the joints by identifying correlations between the range of motion surfaces 304a-304c for different joints. The correlations identified by the computer system 310 can include, for example, commonalities among the range of motion surfaces 304a-304c, such as corresponding landmarks of the range of motion surfaces 304a-304c. Landmarks can include portions of boundaries 305a-305c (e.g., edges) of range of motion surfaces 304a-304c.

The computer system 310 uses the correlations to align the range of motion surfaces 304a-304c in a common coordinate reference system. The range of motion surfaces 304a-304c can be individually aligned relative to a coordinate system or can be directly aligned relative to each other. In some implementations, the computer system 310 can also scale the range of motion surfaces 304a-304c to a common radius of curvature.

Figure 13:
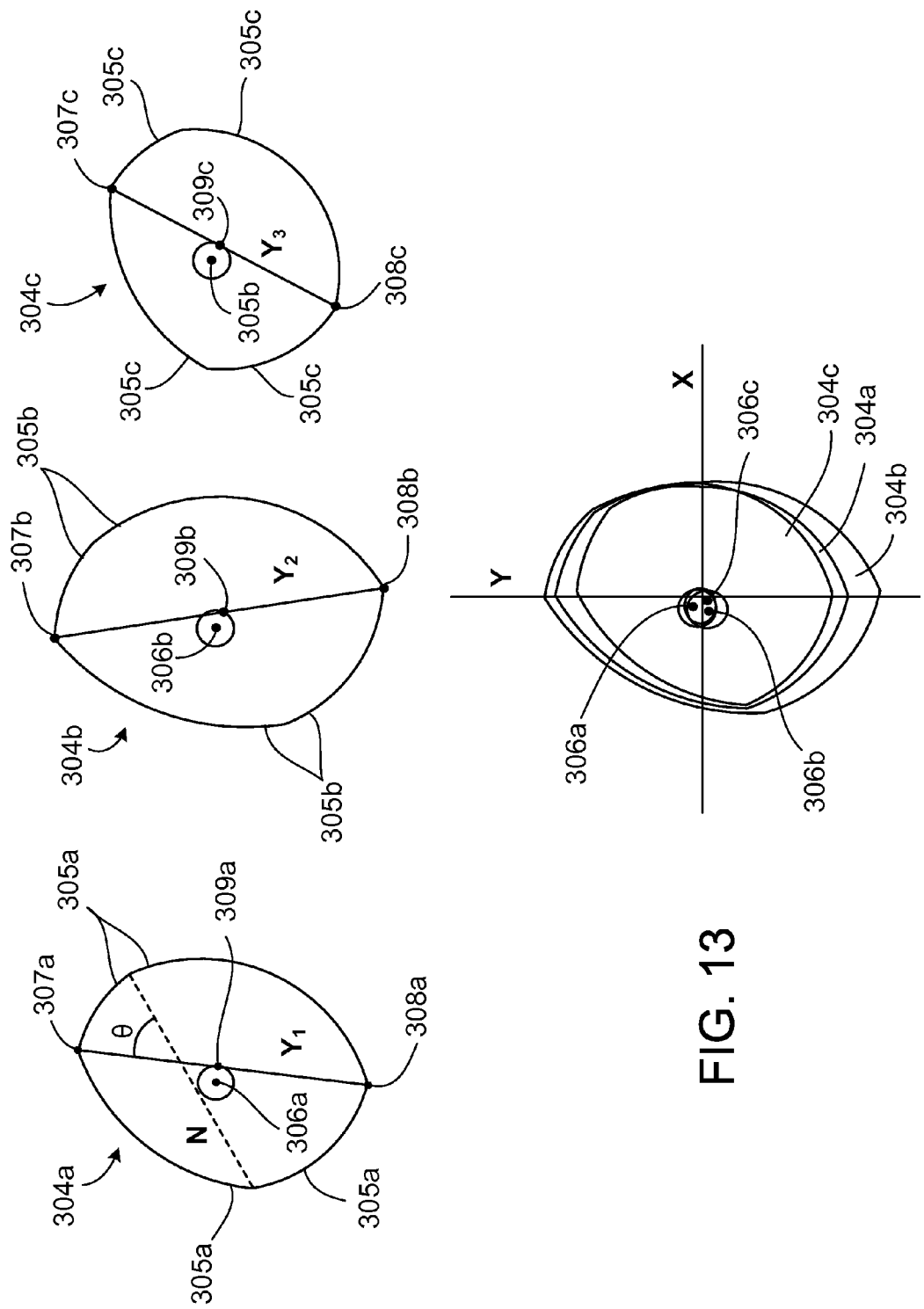

Referring to FIG. 13, an example of a technique for aligning the surfaces 304a-304c in a coordinate system includes determining a position of an axis relative to landmarks of each surface 304a-304c. Landmarks can include, for example, boundaries 305a-305c of the surfaces 304a-304c as a whole, segments of the boundaries 305a-305c, or particular points of the boundaries 305a-305c. Maximum and minimum points as well as inflection points along the boundaries can also be identified and used as landmarks. The computer system 310 identifies landmarks of the different surfaces 304a-304c, and aligns each surface 304a-304c to a coordinate system using the landmarks. Although landmarks may vary in shape and position from one range of motion surface to another, the landmarks used can be characteristic features of range of motion surfaces that are likely to be present in most range of motion surfaces, and thus can indicate correlations between different surfaces.

In the example of FIG. 13, the computer system 310 identifies a first landmark 307a and a second landmark 308a of the range of motion surface 304a. The computer system 310 defines an axis, $Y_1$, through the landmarks 307a, 308a. The computer system 310 identifies correlations with the other range of motion surfaces 304b, 304c by identifying landmarks corresponding to the first landmark 307a and the second landmark 308a. For each of the other range of motion surfaces 304b, 304c, the computer system 310 identifies a corresponding first landmark 307b, 307c and a corresponding second landmark 308b, 308c. The computer system 310 defines an axis, $Y_2$, $Y_3$, respectively, for each surface 304b, 304c based on the corresponding landmarks. For each surface 304a-304c, the computer system 310 also determines the midpoint 309a-309c of the distance between the first landmark 307a-307c and the second landmark 308a-308c.

The computer system 310 aligns each of the axes, $Y_1$, $Y_2$, $Y_3$, along a common axis, Y. The computer system 310 also aligns the surfaces 304a-304c such that the midpoints 309a-309c are each intersected by an axis, X, thus locating the midpoints at the origin of the X-Y coordinate system. By using corresponding landmarks to align the range of motion surfaces 304a-304c, correlations between the 304a-304c are reflected in the resulting positions of the surfaces 304a-304c relative to each other in the coordinate system. The surfaces 304a-304c, by virtue of being aligned to the same reference system according to the same criteria, are thus also aligned relative to each other. Although only two axes are illustrated, the range of motion surfaces 304a-304c can describe the range of motion in three-dimensions, and alignment as described above can orient the surfaces 304a-304c in three dimensions of a coordinate system.

The computer system 310 can also use additional correlations beyond those illustrated to orient the range of motion surfaces 304a-304c. For example, the computer system 310 can determine a second axis, N, for the range of motion surface 304a based on additional landmarks and can determine an angle, θ, between the axis, N, and the axis, $Y_1$. A corresponding angle can be determined for the other range of motion surfaces 304b, 304c and used to align each surface 304a-304c to a coordinate system. The computer system 310 can use commonalities among distances between landmarks, angles between landmarks, areas of the surfaces 304a-304c, and other features to orient the surfaces 304a-304c. In addition, an axis of a coordinate system need not intersect a landmark when aligning the surfaces 304a-304a, and various different relationships between axes and landmarks can be established.

Rather than aligning each surface 304a-304c individually to the coordinate system, corresponding landmarks of the surfaces 304a-304c can be directly aligned relative to each other. In some implementations, the range of motion surfaces 304a-304c are aligned relative to each other using data fitting techniques. Data fitting can be used to align the surfaces 304a-304c relative to each other based on commonalities between the boundaries 305a-305c of the various surfaces 304a-304c, particular landmark features of the boundaries 305a-305c, or the areas spanned by the surfaces 304a-304c. For example, data fitting can be used to determine positions of the surfaces 304a-304c that minimize the overall error between the positions of corresponding landmarks. In some implementations, particular landmarks need not be identified, and the entire boundaries 305a-305c or areas of the surfaces 304a-304c are aligned through data fitting.

Figure 12C:
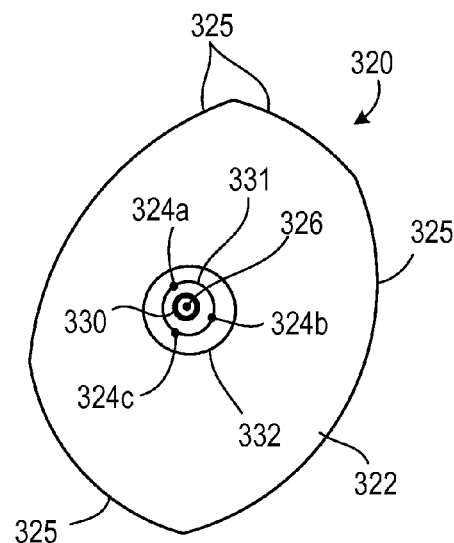

Referring now to FIG. 12C, the computer system 310 generates a composite representation 320 based on the joint data. The composite representation 320 includes information about a generalized range of motion and the position of a generalized impaction axis relative to the generalized range of motion. The computer system 310 uses the correlations between the range of motion surfaces 304a-304c to determine the generalized or composite representation 320. For example, the computer system 310 uses the positions of the surfaces 304a-304c, aligned to a common reference system based on corresponding landmarks, to determine the composite representation 320.

The surfaces 304a-304c are referred to herein as being correlated when alignments of the surfaces 304a-304c based on correlations among corresponding features are known. Thus for the correlated surfaces 304a-304c, the computer system 310 stores data indicating, for example, the position of each surface 304a-304c relative to a reference system.

The composite representation 320 can includes a composite range of motion surface 322 calculated based on the boundaries 305a-305c of the range of motion surfaces 304a-304c. To determine the boundaries 325 of the composite range of motion surface 322, the computer system 310 uses data fitting, for example, to determine boundaries 325 with least error relative to the correlated surfaces 304a-304c as a whole. The computer system 310 alternatively determines an average or weighted average of the boundaries 305a-305c of multiple surfaces 304a-304c.

The computer system 310 also analyzes the intersections of the impaction axes for the joints described in the records 302a-302c. The computer system 310 calculates intersection points 324a-324c where the impaction axes of the correlated surfaces 304a-304c would intersect the composite range of motion surface 322. From the intersection points 324a-324c corresponding to the different impaction axes, the computer system 310 determines a best-fit intersection point 326 on composite surface 322. For example, the computer system 310 calculates the intersection point 326 to be the least error point relative to the intersection points 324a-324c.

The intersection points 306a-306c of the records 302a-302c can each indicate the position of an axis having a particular inclination angle and anteversion angle (e.g., 45 degrees and 15 degrees). As a result, the intersection point 326 represents an intersection through the composite surface 322 of an axis having the same inclination angle and anteversion angle (e.g., 45 degrees and 15 degrees). If the records 302a-302c indicate the intersections of different axes with varying combinations of inclination and anteversion angles, for example, 45 degrees and 15 degrees, 50 degrees and 20 degrees, 50 degrees and 15 degrees, and so on, the composite representation 320 can include intersection points on the composite surface 322 for each of the different axes.

The computer system 310 identifies regions 330, 331, 332 extending about the composite intersection point 326 that indicate statistical confidence levels for the position of an impaction axis relative to the composite range of motion surface 322. For example, the computer system 310 identifies multiple regions 330, 331, 332, each enclosing a different portion of the composite range of motion surface 322, and that contain a particular percentage of intersections from the impaction axes of the correlated records 302a-302c. The first region 330, the second region 331, and the third region 332 may respectively include, for example, 90%, 95%, and 99% of the intersection points 324a-324c of the impaction axes of the correlated records 302a-302c through the composite range of motion surface 322.

A database 300 can include both composite representations 320 and records 302a-302c describing individual joints. The composite representation 320 can include, for example, information that indicates a composite range of motion surface 322 and an intersection point 326 for a composite impaction axis. A center of rotation point 328 (see FIG. 13) for the surface 322 and a radius of curvature of the surface 322 can both be derived from the surface 322, and can also be stored.

The intersection point 326 and the center of rotation point 328 define the position of a composite axis 329 (see FIG. 13) relative to the composite range of motion surface 322. The composite axis 329 is thus based on the similarities between the positions of impaction axes, each at the same known inclination and anteversion angles, relative to the ranges of motion for the joints described in the records 302a-302c. As a result, the composite axis 329 represents an axis having a particular set of inclination and anteversion angles (e.g., 45 degrees inclination and 15 degrees anteversion) relative to the composite surface 322. In some implementations, multiple composite axes can be defined, each corresponding to a different combination of inclination angles and anteversion angles.

2.3 Using Stored Data for Alignment

The system 100 can assist a surgeon by determining the position of an impaction axis using the hip joint data in the database 300, without requiring imaging data of the joint being operated on. Data in the database 300 is used to determine the position of an impaction axis for a joint not described in a record 302a-302c in the database 300.

The impaction axis for a joint can be defined by determining two points along the impaction axis, a calculated center of rotation of the joint and a second point determined relative to the limits of the range of motion of the joint. Data in the database 300 indicates the positions of one or more impaction axes at known inclination and anteversion angles for joints relative to ranges of motion for those joints. Relationships between the impaction axes and the associated ranges of motion of the joints described in the database 300 are used to determine the orientation of the second point along the impaction axis for the joint not described in the database 300. Imaging data for the joint is not needed to determine the trajectory of the impaction axis for the joint.

Figure 14B:
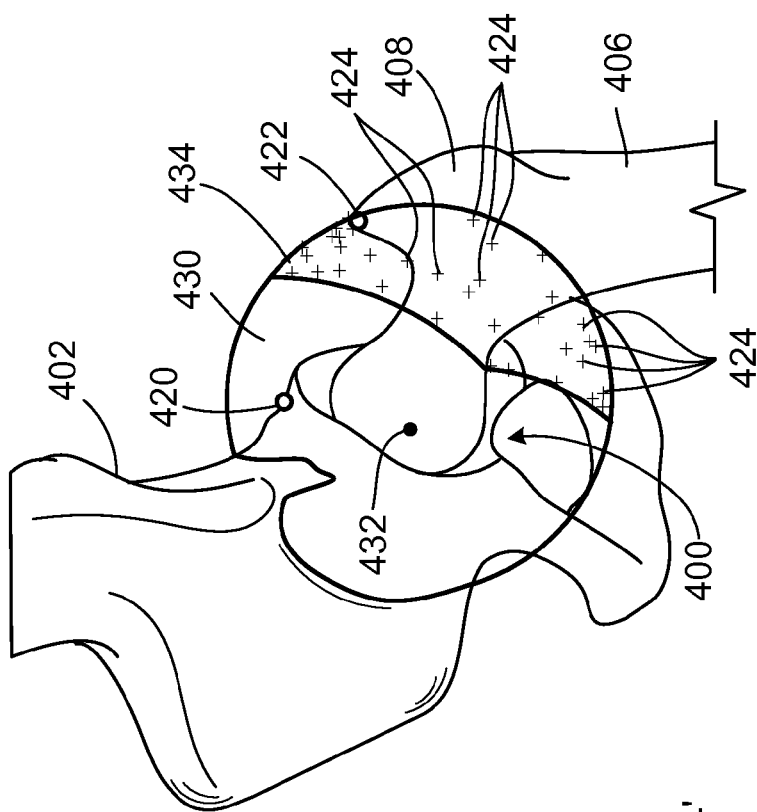
FIGS. 14A, 14B, 15, and 16 are illustrations of a process for determining an alignment for a joint using data for other joints.
Figure 14A:
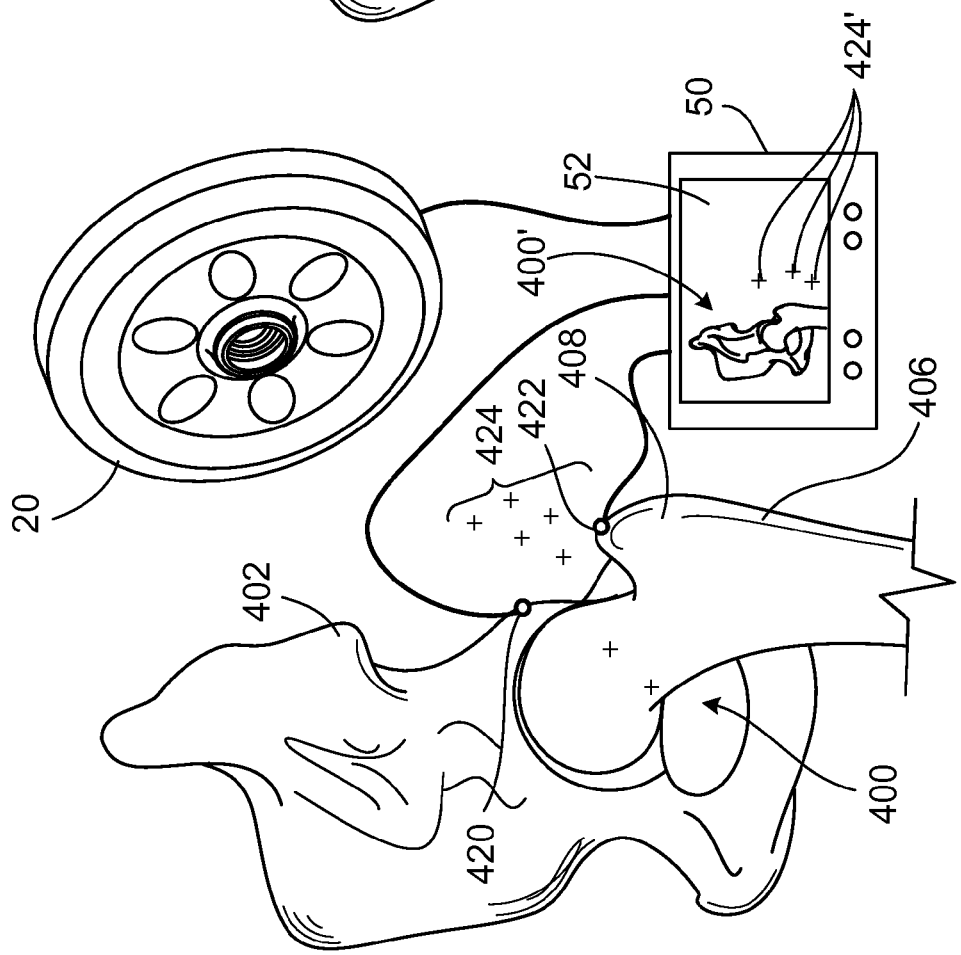

Referring to FIG. 14A, a surgeon establishes two references at positions that are fixed relative to the joint 400 and moveable relative to each other as the joint 400 moves. For example the surgeon implants a first EM field sensor 420 at the pelvis 402 and implants a second EM field sensor 422 at the tip of the greater trochanter 408 of the femur 406. The surgeon moves the joint 400 through a range of motion while the sensors 420, 422 are within the working volume of the EM field generator 21. The control unit 50 records locations 424 of the sensor 422 relative to the sensor 420 at multiple positions of the joint 400, including positions at extremities of the range of motion of the joint 400. Images or other representations 400', 424' of the joint 400 or points 426, or other data, can be presented on the user interface 52.

Referring to FIG. 14B, as described for FIG. 10A, the control unit 50 calculates a surface, such as a sphere 430, based on the measured locations 424. The control unit 50 calculates a center point 432 of the sphere 430, which corresponds to the center of motion of the joint 400. The control unit 50 also calculates a range of motion surface 434, which can be a portion of the sphere 430. The range of motion surface 434 approximates the region spanned by the measured locations 424 of the sensor 422 during movement of the joint 400 through the range of motion. The positions of the sphere 430, surface 434, measured locations 424, center of rotation 432 can be displayed or otherwise indicated on the user interface 52.

Figure 15:
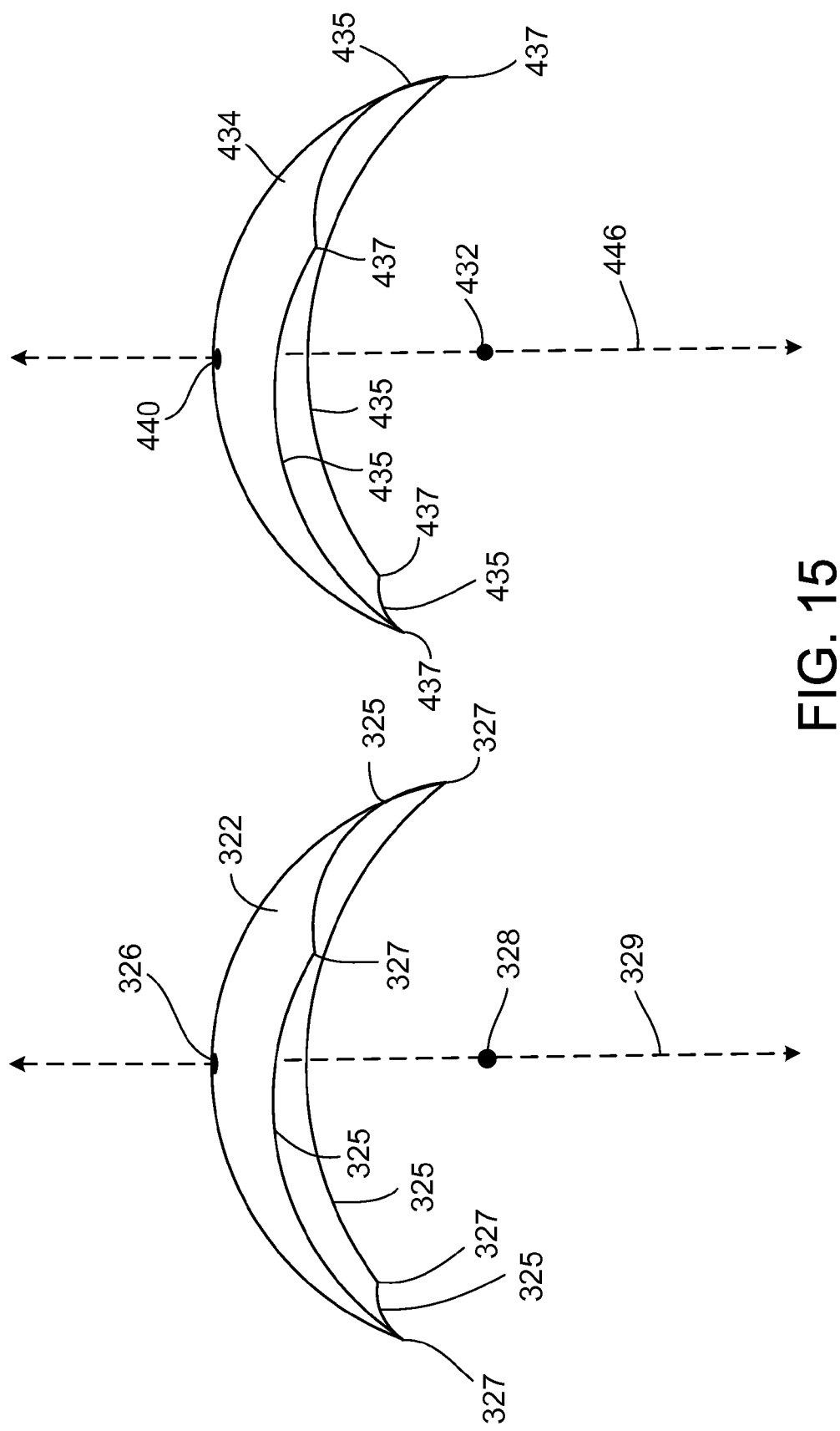

Referring to FIG. 15, the control unit 50 determines a point 440 where an impaction axis 446 intersects the range of motion surface 434. The intersection point 440 and the center point 432 define the position of the impaction axis 446 for the joint 400. To identify the intersection point 440, the control unit 50 uses data from the database 300. The control unit 50 can store the database 300 on an internal storage medium. In addition, or alternatively, the control unit 50 accesses the database 300 over a network or from a removable medium.

The location of the intersection point 440 on the surface 434 can be determined based on the location of the intersection point 326 on the composite surface 322. For example, the control unit 50 can locate a point 440 on the surface 434 corresponding to the intersection point 326 relative to the composite surface 322. The corresponding point 440 can be one that has, for example, a similar location relative to the boundaries 435 of the surface 434 as the point 326 has relative to the boundaries 325 of the composite surface 322.

The position of the impaction axis 446 can be determined based on similarities of the geometry of the surfaces 322, 434. For example, the position of the intersection point 326 relative to the boundaries 325 of the composite surface 322 is used to determine the corresponding intersection point 440 of the impaction axis 446 relative to the boundaries 435 of the surface 434 for the joint 400. The control unit 50 can identify landmarks 327 of the composite surface 322 and can determine relative distances between the intersection point 326 and the landmarks 327. The control unit 50 can then identify landmarks 437 for the surface 434 corresponding to the landmarks 327 of the composite surface 322, and can define the intersection point 440 at a location having similar relative distances with respect to the landmarks 437 for the surface 434.

For example, the control unit 50 can align the two surfaces 434, 322 relative to each other in a similar manner as described for FIG. 13. The control unit 50 orients the surfaces 322, 434 in a common coordinate reference system using correlations between the surfaces 322, 434 including, for example, corresponding landmarks 437, 327 and corresponding boundaries 325, 435. The control unit 50 can align the surfaces 322, 434 based on, for example, least error between the boundaries 325, 435 of the surfaces 322, 434, greatest degree of overlap of the area of the surfaces 322, 434, alignment of landmarks 437, 327 of surfaces 322, 434, or a combination of these and other criteria. Once the two surfaces 322, 434 are oriented relative to each other, the intersection point 326 on the composite surface 322 coincides with the corresponding location on the range of motion surface 434. Thus the intersection point 440 can be selected as the location of the intersection point 326 when the surfaces 322, 434 are aligned based on corresponding features.

In some implementations, the intersection point 440 is determined using records 302a-302c describing individual joints rather than a composite representation 320 of multiple joints. For example, the control unit 50 can access one or more records 302a-302c for different joints and can determine the location of the intersection point 440 based on one or more intersection points 324a-324c described in the records 302a-302c. The control unit 50 can also determine the intersection point using a subset of the records 302a-302c, for example, a subset of records that the control unit 50 selects based on a high degree of similarity to the range of motion surface 434.

In some implementations, different composite representations are used for different patients. For example, a different composite representation can be accessed for patients having a small, medium, or large femoral neck length. Each composite representation can be generated using data describing joints for which the range of motion surface has a radius of curvature within a particular range. For patients having a radius of curvature in a particular range, the appropriate implant likely has a femoral neck length in a corresponding range. Similarly, a radius of curvature in a particular range can correspond to a particular range of femoral stem sizes.

To determine the intersection point 440 for the joint 400, the control unit 50 selects the composite representation most appropriate for the radius of curvature of the range of motion surface 434 of joint 400. Thus the intersection point can be determined based on the properties of joints having similar characteristics to the joint being operated on. In addition, each different composite representation can correspond to a different femoral implant size or range of femoral implant sizes. The control unit 50 can suggest to the surgeon a particular femoral implant or implant characteristic that is suited to the joint 400 based on the particular composite representation used to calculate the intersection point 440, based on the radius of curvature of the range of motion surface 434, or based on other aspects of the range of motion of the joint 400.

Figure 16:
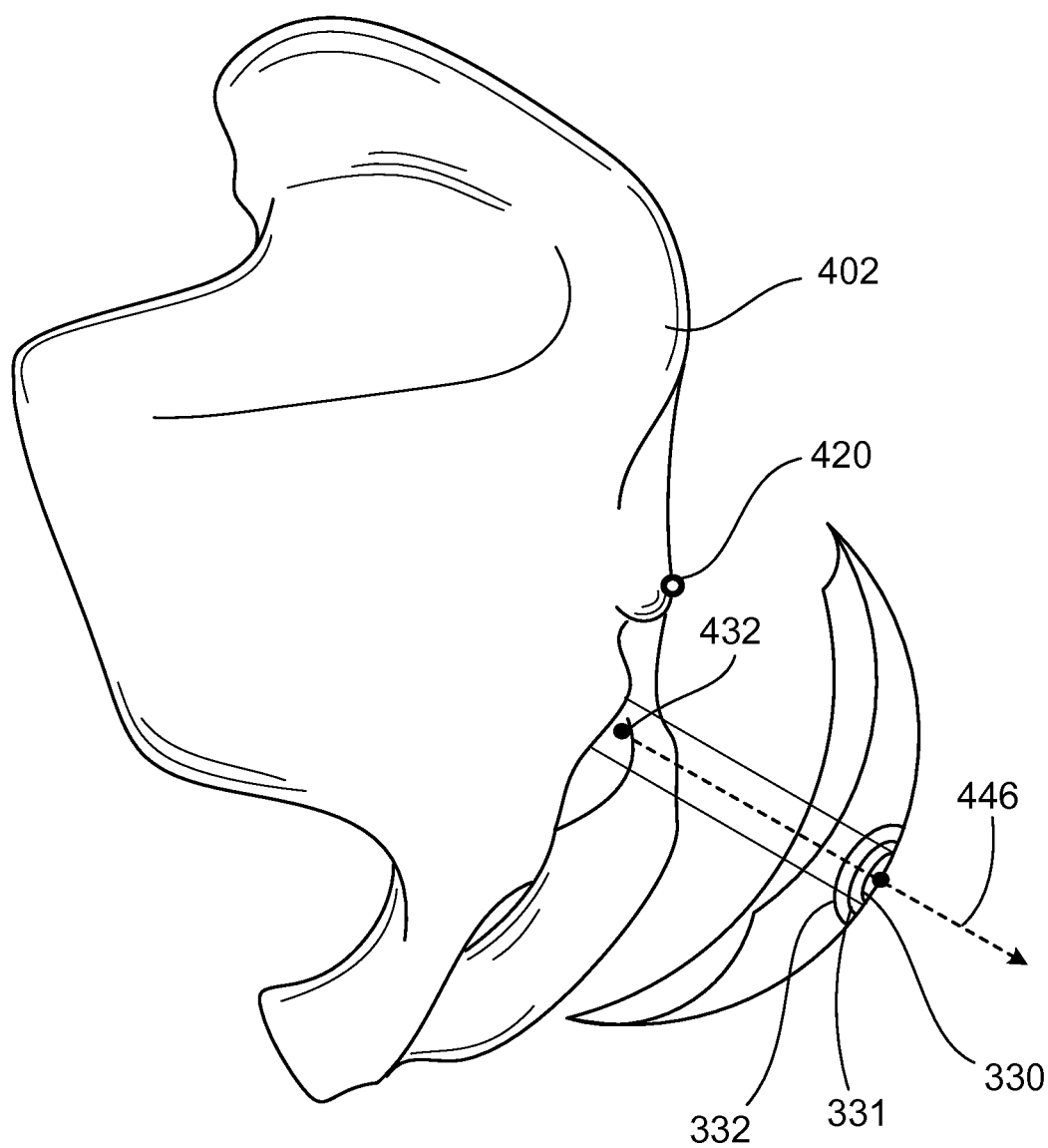

Referring to FIG. 16, the control unit 50 defines the impaction axis 446 for the joint 400 through the point 432 corresponding to the center of rotation of the joint 400 and through the intersection point 440 located on the range of motion surface 434. The positions of the range of motion surface 434, the center of rotation point 432, and the second point are all known relative to the first sensor 420. Thus the system 100 can be used to align instruments 30 with respect to the impaction axis 446 in the reference frame of the first sensor 420.

The inclination angle and anteversion angle of the impaction axis 446 are also known, because the impaction axis 446 is selected to correspond to the composite axis 329. The composite axis 329 represents a known inclination angle and anteversion angle. Because the impaction axis 446 has a corresponding position relative to the range of motion surface 434 as the composite axis 329 has relative to the composite surface 322, the impaction axis 446 has the same inclination angle and anteversion angle as the composite axis 329. Therefore, the position of the impaction axis 446, known relative to anatomical references, can be used as a reference axis from which positions of instruments 30 can be determined relative to anatomical references.

The control unit 50 calculates the alignments of instruments as described above for FIGS. 5A and 5B, and outputs indications of the alignment of instruments 30 on the user interface 52, as described above with respect to FIGS. 6, 7A, and 7B. The control unit 50 also displays tolerances about the impaction axis 446 that indicate how closely an alignment of an instrument corresponds to alignments for joints described in the database 300. For example, the control unit 50 can indicate the regions 330, 331, 332 which would include intersections of a particular percentage of impaction axes described in the database 300. For example, the regions 330, 331, 332 can be indicated that respectively contain at least 90%, 95%, and 99% of the impaction axes described in a sample set of joint records 302a-302c. The boundaries of the regions 330, 331, 332 can be accessed by the control unit 50 or can be determined by the control unit 50.

In addition to indicating the alignment of the instruments 30 relative to the impaction axis 446, the control unit 50 can indicate the preferred and current reaming depths for reaming of the acetabulum of the joint 400. As described above, the control unit 50 calculates the preferred reaming depth such that after impaction of an acetabular shell, the center of rotation of the joint 400 will be located at the original the center of rotation point 432 of the joint 400, or at a desired offset from the center of rotation point 432. Also, the control unit 50 can display the anteversion angle and inclination angle of instruments 30, based on their position relative to the impaction axis 446.

In some implementations, the control unit 50 compares the shape and size of the range of motion surface 434 for the joint 400 with the composite surface 322. When the range of motion surface 434 is outside of a threshold level of similarity from the composite range of motion surface 322, the control unit 50 indicates the difference on the user interface 52. For example, the control unit 50 can determine, based on differences between the surfaces 322, 434 that the joint 400 is abnormally flexible in one or more aspects, which may warrant special considerations to ensure stability of the reconstructed joint 400. The control unit 50 can thus alert the surgeon that caution or adjustment to the procedure may be needed to ensure that the reconstructed joint 400 is not prone to dislocation. The control unit 50 can suggest compensation for abnormal range of motion characteristics, such as suggesting the use of a particular inclination angle or anteversion angle calculated to compensate for the abnormality.

(3) Alignment for Femoral Resurfacing

A surgeon can use the system 100 to prepare a femur to receive a femoral implant. Using input about the position and dimensions of the femoral neck, the system 100 calculates an axis for a femoral guide pin. The femoral neck can be measured intraoperatively, so that no imaging data for the joint is needed. The system 100 also indicates the alignment of instruments relative to the calculated axis to guide installation of the guide pin along the axis. The installed guide pin can then be used for reaming the femoral head.

Figure 17:
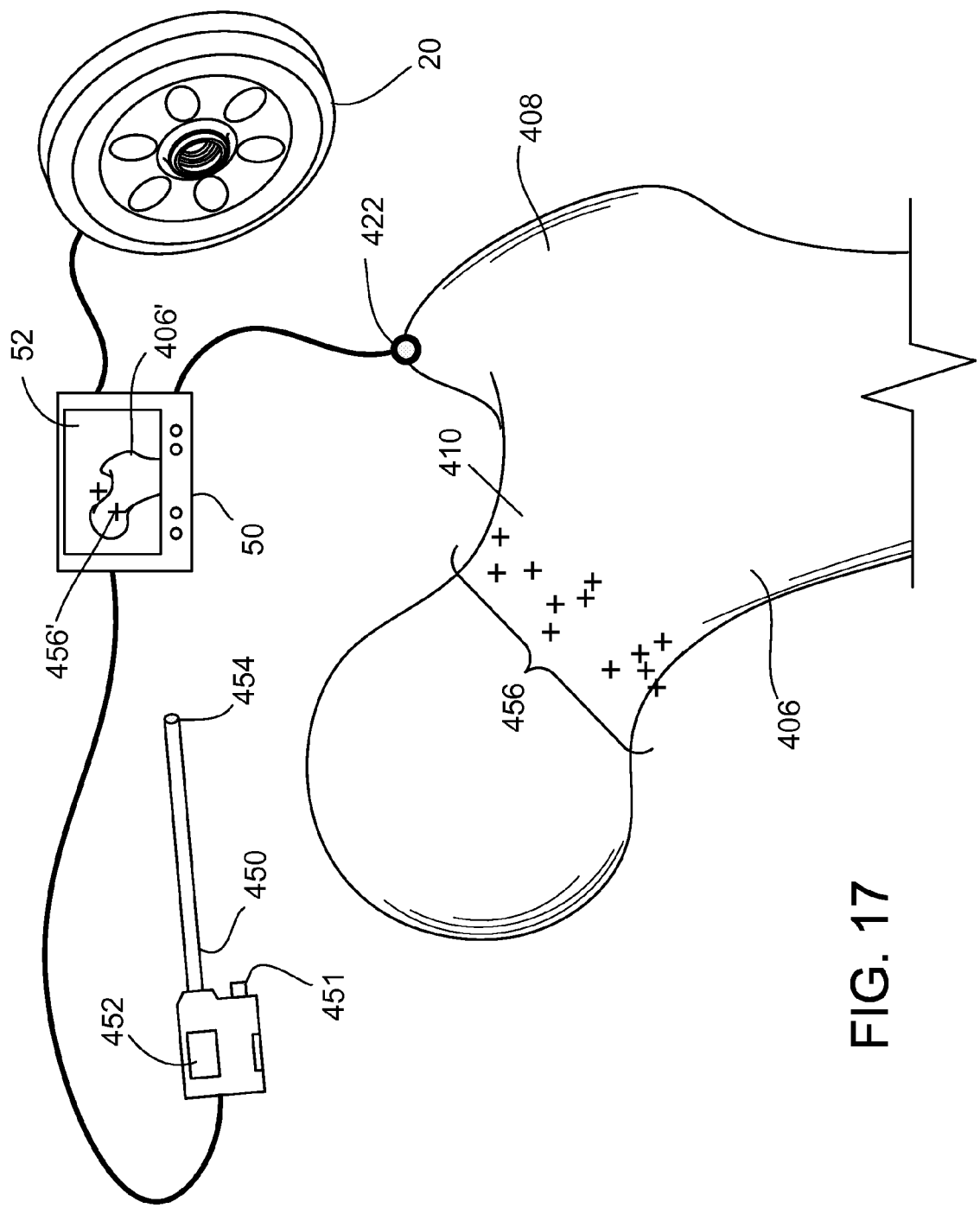
FIGS. 17 to 20 are illustrations of a process for selecting and targeting an alignment relative to a bone of a joint.

Referring to FIG. 17, the surgeon establishes a reference at a fixed location relative to the femur 406 of the joint 400. For example, the sensor 422, previously used to determine the range of motion of the joint 400, can be maintained at the greater trochanter 408 of the femur 406. The sensor 422 can be located to avoid interference with resurfacing of the femoral head 409 and femoral neck 410 or with implantation of a femoral implant. The femur 406 and the sensor 422 are brought into the working volume of the EM field generator 21.

The surgeon exposes and measures the femoral neck 410. For example, the surgeon measures different locations 456 on the surface of the femoral neck 410 by contacting the femoral neck 410 with a probe 450 coupled to an EM field sensor 452. The probe 450 includes an end 454, such as a narrow tip, that contacts the femoral neck 410. The location of the end 454 of the probe 450 is known and fixed relative to the sensor 452 of the probe 450. For example, the distance between the sensor 452 and the end 454 is known, allowing the control unit 50 to determine the position of the end 454 based on the signal produced by the sensor 452.

With the end 454 of the probe 450 in contact with the femoral neck 410, the surgeon presses a button 451 or activates another trigger, causing the control unit 50 to record the current position of the sensor 452 relative to the sensor 422. The control unit 50 determines the position of the sensor 452 of the probe 450 relative to the end 454 and stores the location 456 of the end 454 contacting the femoral neck 410. The surgeon moves the probe 450 and records additional locations 456 about the femoral neck 410.

In some implementations, the control unit 50 automatically records a location 456 in response to the probe 450 engaging the femoral neck 410. The end 454 of the probe 450 can include an element that is responsive to contact, such as a pressure sensitive element or a depressible element. When contact with the end 454 occurs, the probe 450 sends a signal to the control unit 50, triggering the control unit 50 to record the current position of the probe 450. Thus as the surgeon contacts the end 454 against the femoral neck 410, the control unit 50 automatically records the contacted location 456.

As the locations 456 are measured, the control unit 50 can indicate the position of the probe 450 and indicate the locations 456 relative to the femur 406, for example, by displaying indications 456' on a three-dimensional view 406' of the femur 406 on the user interface 52.

Figure 18:
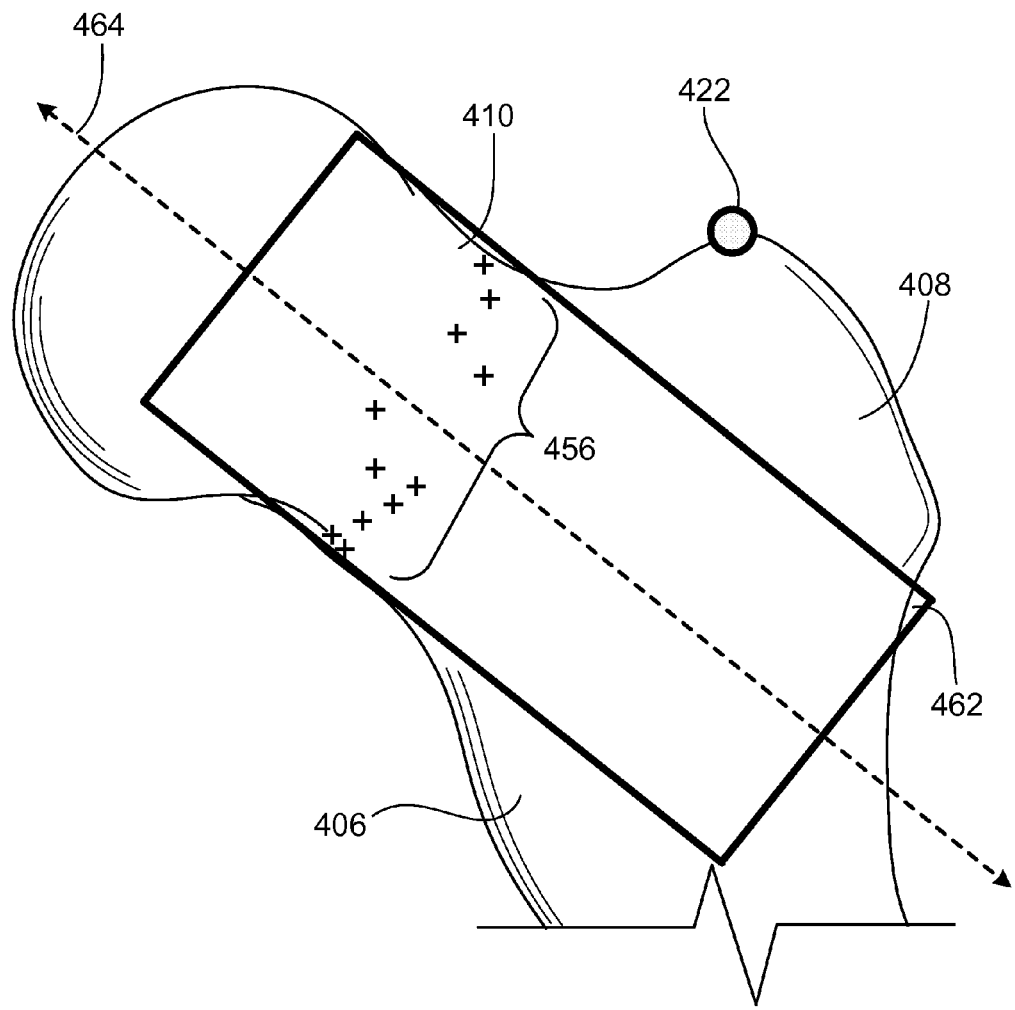

Referring to FIG. 18, the control unit 50 uses the measured locations 456 to calculate an axis 464 for insertion of a guide pin. For example, the control unit 50 extrapolates from the measured locations 456 to calculate a cylinder 462 about the femoral neck 410. The cylinder 462 can be calculated to have a least error size and alignment relative to the locations 456. Alternatively, the cylinder 462 can be calculated to have a radius that encompasses substantially all of the locations 456. The control unit 50 calculates the central axis 464 of the cylinder 462, which is the preferred trajectory of the guide pin. The control unit 50 may display a three-dimensional view similar to the view illustrated in FIG. 16 on the user interface 52.

Figure 19:
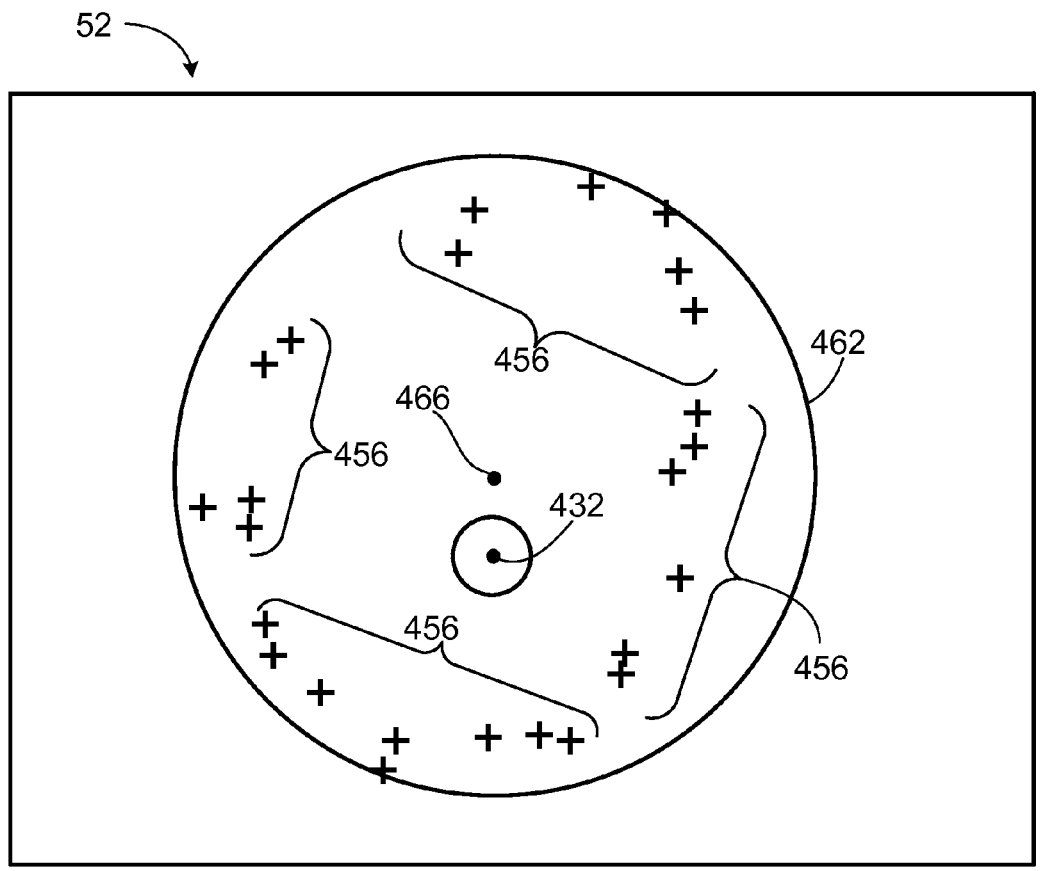

Referring to FIG. 19, the control unit 50 displays a view of the cylinder 462 on the user interface 52. For example, the control unit 50 displays a view of the cylinder 462 aligned through the central axis of the cylinder 462. The radius of the cylinder 462 can also be determined and indicated on the user interface 52. The measured locations 456 and a point 466 indicating the central axis 464 are also indicated on the user interface 52. Using the user interface 52, the surgeon can adjust the location of the cylinder 462 relative to the measured locations 456, and thus alter the position of the axis 464 relative to the measured locations 456. For example, the surgeon can shift the position of the cylinder 462 and its central axis 464 in a direction normal to the cylinder 462, adjusting an offset of the cylinder 462 relative to the femoral neck 410. In some implementations, when the center of rotation of the joint 400 is determined, as described above, the center of rotation point 432 can be indicated on the user interface 52.

Figure 20:
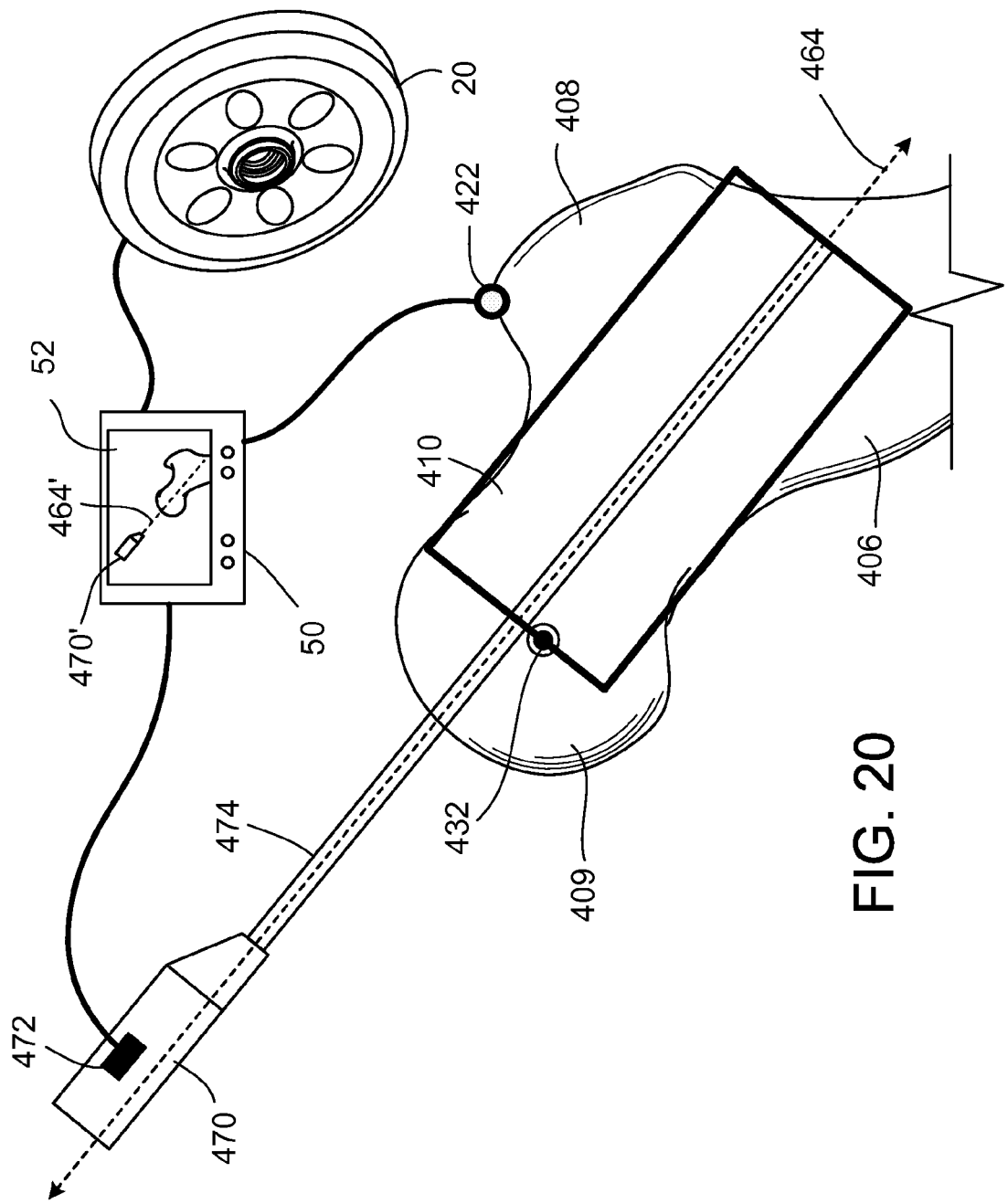

Referring to FIG. 20, the control unit 50 indicates the alignment of instruments relative to the femur 406. The surgeon uses a drill 470 that includes an EM field sensor 472 coupled at a known, fixed position relative to the drill 470. The drill 470, with its attached sensor 472, and the femur 406 with the implanted sensor 422 are brought into the working volume of the EM field generator 21. Based on the signals received from the sensors 422, 472, the control unit 50 calculates the position of the drill 470 relative to the axis 464.

Alternatively, rather than using a sensor 472 coupled to the drill 470, the drill 470 can be coupled to the EM field generator 21 at a known position. The position of the implanted sensor 422 relative to the EM field generator 21 thus indicates the position of the drill 470 relative to the sensor 422, and can be used to determine the orientation of the drill 470 relative to the axis 464.

On the user interface 52, the control unit 50 displays an indication 470' of the position of the drill 470 and an indication 464' of the position of the axis 464 relative to the drill 470. For example, the control unit 50 indicates angular deviations and translational offsets from the axis 464. The control unit 50 can display an illustration showing three-dimensional aspects of the femur 406, based on the measured locations 456, and the alignment of the axis 464 and the alignment of the drill 470 relative to the femur 406.

The surgeon fits a guide pin 474 on the drill 470 and implants the guide pin 474 along the axis 464, as indicated by the control unit 50. As the guide pin 474 is inserted, the control unit 50 updates the information displayed on user interface 52 to reflect the current position of the drill 470 relative to the axis 464, based on signals received from the sensors 422, 472. After the guide pin 474 is implanted, the surgeon visually confirms correct placement of the implanted pin 474 relative to anatomical features of the femur 406. With the guide pin 474 in place, the surgeon uses the guide pin 474 to align cutting tools to prepare the femur 406 to receive a femoral implant.

In addition, the radius of the cylinder 462 can be used to select the size and configuration of tools used to cut the femoral head 409. For example, a surgeon can configure cutting tools to ensure that cutting of the femoral neck 410 does not occur within a particular radius of the guide pin 474, to avoid creating a notch in the femoral neck 410 while preparing the femur 406. The radius about the guide pin 474, in which cutting does not occur, can be the radius of the cylinder 462.

Based on the measurement of the range of motion for the joint 400, the system 100 calculates the center of rotation point 432 for the joint 400 relative to the implanted sensor 422. The center of rotation point 432 is a point located inside the femoral head 409. The center of rotation point 432, determined prior to dislocation of the joint 400, can be used by the control unit 50 to determine, for example, the appropriate depth to ream the femur 406 or the preferred location at which to perform an osteotomy of the femoral neck 410.

(4) Locating a Surgical Axis

A surgeon can use the system 100 to determine a surgical alignment for one bone of a joint based on the position of another bone of the joint. For example, for the hip joint 400, the position of the femoral guide pin axis 464 (FIG. 18) can be used to determine the position of an impaction axis relative to the pelvis 402. This technique, described in further detail below, is an alternative to the methods of determining the position of an impaction axis using a guide or using joint data for other joints.

The surgeon attaches a first reference, the first sensor 420, at a fixed position relative to the pelvis 402 and attaches a second reference, the second sensor 422, at a fixed position relative to the femur 406, as described with respect to FIG. 14A. The second reference 422 need not be placed at the tip of the greater trochanter 408, but may be located there. Optionally, the range of motion of the joint 400 and the center of rotation of the joint 400 can be determined relative to the first sensor 420 using the techniques described with respect to FIG. 14A.

Referring to FIG. 21A, the surgeon dislocates the joint 400. The surgeon determines an alignment relative to the femur 406, for example, a substantially central axis through the neck 410 of the femur 406. This axis can be the guide pin axis 464 determined as described with respect to FIGS. 17 and 18, determined based on measured locations 456 about the neck 410 of the femur 406. The control unit 50 determines the position of the guide pin axis 464 relative to the second sensor 422. Alternatively, rather than determining the position of a substantially central axis through the neck 410 of the femur 406, the position of a different axis having a known anatomical alignment relative to the femur 406 can be determined.

Referring to FIG. 21B, rather than inserting a guide pin along the guide pin axis 464, the surgeon reduces the joint 400. With the joint 400 reduced, the surgeon places the femur 406 at a known position relative to the pelvis 402. For example, the surgeon places the leg of the patient in a neutral position. The neutral position can be a "zero-degree" position corresponding to full extension of the hip, for example, a position in which the femur 406 extends straight in a similar manner as if the patient were standing. In the neutral position, the guide pin axis 464, which represents a substantially central axis through the femoral neck 410, coincides with the preferred impaction axis for installing an acetabular implant.

The surgeon brings the identifier 20 near the joint 400 so that the first sensor 420 and the second sensor 422 are in electromagnetic communication with the identifier 20. The surgeon selects a control of the control unit 50, indicating that the femur 406 is positioned in the neutral position. In response, the control unit 50 uses sensor signals from the first sensor 420 and the second sensor 422 to calculate the position of each sensor 420, 422 relative to the identifier 20. With the positions of the sensor 420, 422 known relative to the same reference, the control unit 50 calculates the position of the second sensor 422 relative to the first sensor 420.

As described above, the control unit 50 previously determined the position of the guide pin axis 464 relative to the second sensor 422. The control unit 50 uses (i) the offset between the first sensor 420 and the second sensor 422 and (ii) the offset between the second sensor 422 and the guide pin axis 464 to determine the position of the guide pin axis 464 relative to the first sensor 420. Because the joint 400 is in the neutral position, the position of the guide pin axis 464 is the position of the impaction axis 465 for the joint 400. The control unit 50 records the position of the guide pin axis 464, determined relative to the first sensor 420, as the position of the impaction axis 465.

The surgeon dislocates the joint 400 and aligns instruments relative to the impaction axis 465, for example, as described with respect to FIGS. 5A and 5B, by coupling the identifier 20 or a third sensor to the instrument 30. The control unit 50 displays information indicating the current position of the instrument 30 relative to the joint 400 and relative to preferred alignments, as described with respect to FIGS. 6, 7A, and 7B. Although the inclination angle and the anteversion angle of the impaction axis 465 may not be precisely known, the control unit 50 can display, with a margin of error, a likely inclination angle and anteversion angle corresponding to the impaction axis 465. The surgeon uses the output on the user interface 52 to ream the acetabulum of the joint 400 and to install an acetabular implant along the impaction axis 465.

In some implementations, the position of the impaction axis can be determined by positioning the femur 406 in a known position relative to the pelvis 402 different from the neutral position of the joint 400. For example, the position of the sensors 420, 422 can be measured at 90 degrees of flexion. The control unit 50 can use a known offset or relationship (known for the particular hip joint 400 or for hip joints generally) between this position and the neutral position of hip joints to determine the position of the impaction axis 465 from the position of the guide pin axis 464. In a similar manner, a calculated position relative to the femur 406 other than a substantially central axis through the femoral neck 410 may be used, together with a known relationship between the calculated position and the femoral neck 410.

As an alternative, after determining the position of the guide pin axis 464, a hole can be drilled along the guide pin axis 464 before reducing the joint 400 and determining the position of the impaction axis 465. The surgeon inserts a third sensor into the guide pin hole along the guide pin axis 464, in alignment along the guide pin axis 464. The surgeon reduces the joint 400 while the third sensor resides within the femoral head 409 or the femoral neck 410. The surgeon then positions the joint 400 in the neutral position and uses the control unit 50 to record the position of the third sensor relative to the first sensor 420 while the joint 400 is in the neutral position. In the neutral position of the joint 400, the third sensor is aligned along the preferred impaction axis 465 of the joint.

The surgeon again dislocates the joint 400 and removes the third sensor from the guide pin hole. The surgeon can couple the third sensor at a known position of the instrument 30. As the surgeon moves the instrument 30, the control unit 50 can indicate the position of the third sensor relative to the previously measured position of the third sensor. The output of the control unit 50 can assist the surgeon to return the third sensor to its previous position along the impaction axis 465 or to a particular offset from the impaction axis, thus aligning the instrument relative to the impaction axis 465.

The same technique may be used to determine an alignment for joints other than hip joints, including ball and socket joints such as a shoulder joint. For example, the surgeon can place a first sensor at a fixed position relative to the scapula and a second sensor at a fixed position relative to the humerus. The surgeon dislocates the shoulder joint, and measures locations on the humerus similar to the locations measured on the femoral neck for a hip joint. Using the measured locations, the control unit 50 determines the position of a first axis relative to the second sensor, which is on the humerus. The first axis has a known position relative to the humeral head, for example, the control unit 50 determines a position of substantially central axis through the anatomical neck of the humerus, or another known position relative to the humerus.

The surgeon then reduces the shoulder joint, and aligns the humerus to a known position relative to the scapula. The known position can be a neutral position, for example, a position corresponding to the patient's arm at her side, with the longitudinal axis of the humerus generally parallel to the longitudinal axis of the patient's body. While the shoulder joint is in the known position, the surgeon uses the control unit to determine the position of the first axis relative to the first sensor. The surgeon uses the control unit 50 to determine the position of an impaction axis for preparation and installation of a glenoid implant for the shoulder joint. The impaction axis may not coincide with the first axis when the shoulder joint is in the neutral position, but nevertheless can have, for shoulder joints generally, a known angular offset and positional offset from the anatomical position represented by the first axis when the joint is in the neutral position. In a similar manner as described above, the control unit 50 determines the position of the impaction axis based on the position of the second sensor relative to the first sensor, the position of the first axis relative to the second sensor, and a standard offset between the first axis and the position of an impaction axis.

(5) Trialing Techniques

A reference, such as an EM field sensor, can be attached to a trial component (e.g., a trial implant) or a permanent implant to determine the suitability of the trial component or the implant for a particular joint. For example, a surgeon can use the system 100 can to select an appropriate femoral component for the hip joint 400. Similar techniques can be used to select an acetabular implant, or to select implants for another type of joint, such as a shoulder joint.

Figures 22A, 22B:
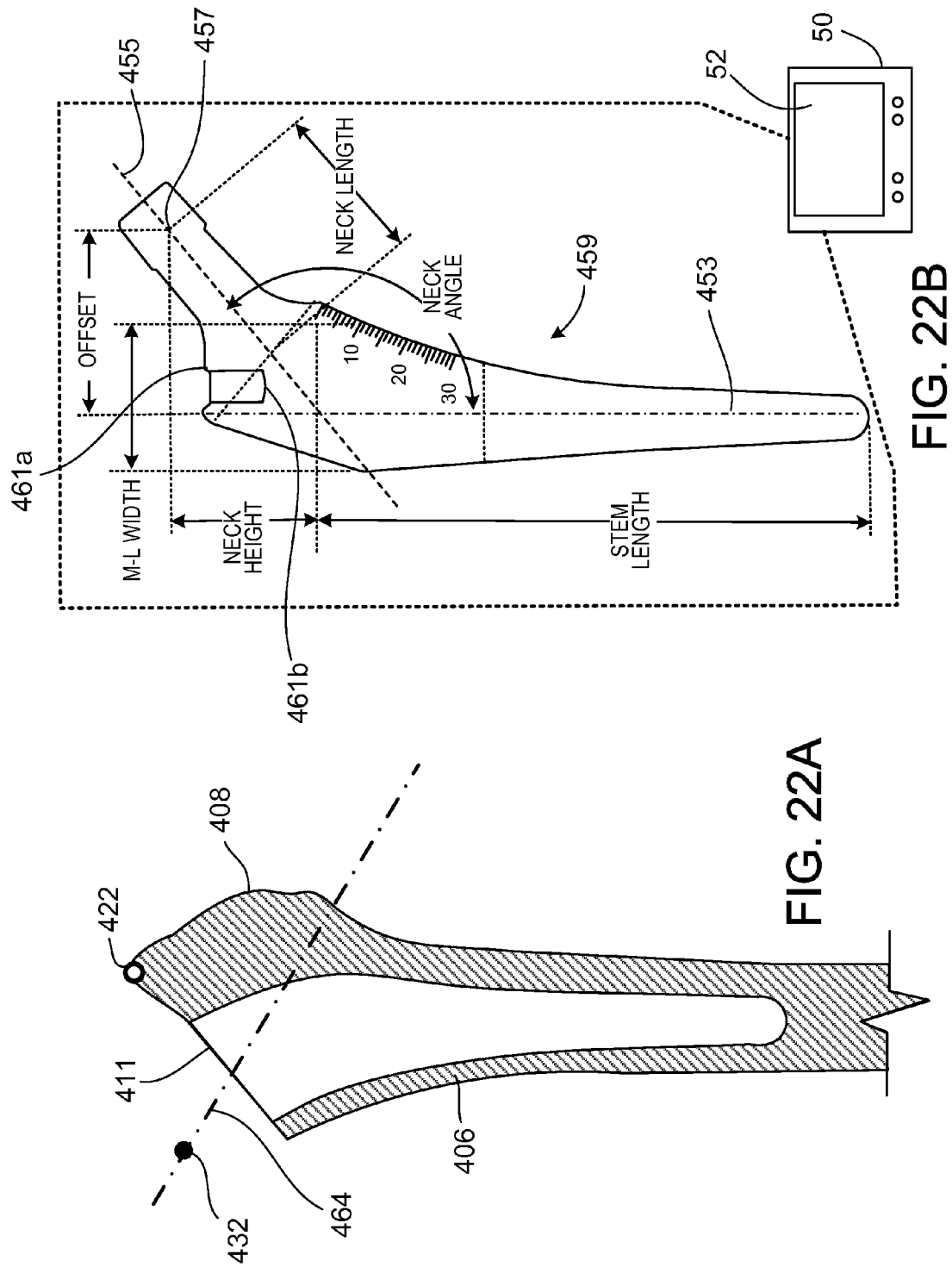
FIGS. 22A, 22B, and 23 are illustrations of a process for selecting an implant.

Referring to FIG. 22A, the location of the center of rotation point 432 of the joint 400 has been determined, for example, as described with respect to FIGS. 14A and 14B. The position of a preferred femoral neck axis for the femur 406, such as the guide pin axis 464, has also been determined, for example, as described with respect to FIGS. 17 and 18. These positions are stored by the control unit 50 as relative positions from second sensor 422, which is attached at a fixed location relative to the femur 406. The positions of the center of rotation point 432 and axis 464 are properties of the joint 400 indicating, for example, preferred alignments that should be matched by an implant.

The surgeon prepares the femur 406 to receive an implant, for example, by performing an osteotomy of the femoral neck 410 and femoral head 409. The surgeon also reams into the femur 406 along the longitudinal axis of the femur to define an opening 411 in the femoral canal. The femur 406 is thus prepared to receive a femoral implant.

Referring to FIG. 22B, the control unit 50 accesses data indicating the characteristics of one or more trial components. For example, the control unit 50 can access a trial component library including data for each of multiple femoral trial components. For each trial component, the data can indicate one or more of neck length, neck height, neck angle, neck length, offset from a stem axis 453, a component width or other dimension, and other characteristics. The data can also indicate positions of a trunnion or other fastener to receive a ball head.

The characteristics indicated by the data can include functional characteristics that define how a joint receiving the trial component will operate. Functional characteristics can include the position of a neck axis 455, for example the position of a substantially central axis through the neck of the trial component. Functional characteristics can also include a joint center of rotation point 457, which can represent a center of rotation that would result for a joint due to installation of the implant. The data can also describe adjustments to the trial component and offsets that can be achieved from standard positioning, for example, through the use of ball heads with different dimensions. In some implementations, different ball heads can be used to achieve different center of rotation points for the same trial component or implant.

The data can include data about trial components and corresponding implants for multiple implant types. The data can also describe modular implant systems, permitting the control unit 50 to determine the dimensions and characteristics of different combinations of modular components. In some implementations, the data for a trial component represents a model 459 indicating external surface dimensions of the trial component. The control unit 50 can use the model 459 not only to determine positions along the exterior of a matching trial component, but also to display a two-dimensional or three-dimensional visualization of the trial component.

The data also describes the position of one or more landmarks 461a, 461b relative to the trial component. As a result, the characteristics of each trial component can have a known relationship relative to the landmarks. For example, the positions of the neck axis 455, the joint center of rotation point 457, and surfaces of the trial component represented by the model 459 can be known relative to each landmark 461a, 461b.

Using the user interface 52, the surgeon enters her preferences, such as the preferred type of implant or implant system to be used during the procedure. Using the data in the trial component library, the control unit 50 compares the characteristics of trial components with the known characteristics of the femur 406 and the joint 400. For example, the second reference 422 can be located at an anatomic reference location of the femur 406, such as the tip of the greater trochanter 408, and the location can be input to the control unit 50. The control unit 50 uses the distance between the center of rotation point 432 and the second reference 422 to determine a neck length for a trial component likely to match the characteristics of the joint 400. Similarly, the control unit 50 uses the location of the center of rotation point 432 relative to the location of the second reference 422 to determine a neck angle for a trial component. The control unit 50 uses the location of the center of rotation point relative to the axis 464 to determine an offset needed, if any, to achieve the joint center of rotation point 432. The control unit 50 selects one or more trial components that are likely to result in the correct joint characteristics, and provides information indicating the selected trial components on the user interface 52.

Figure 23:
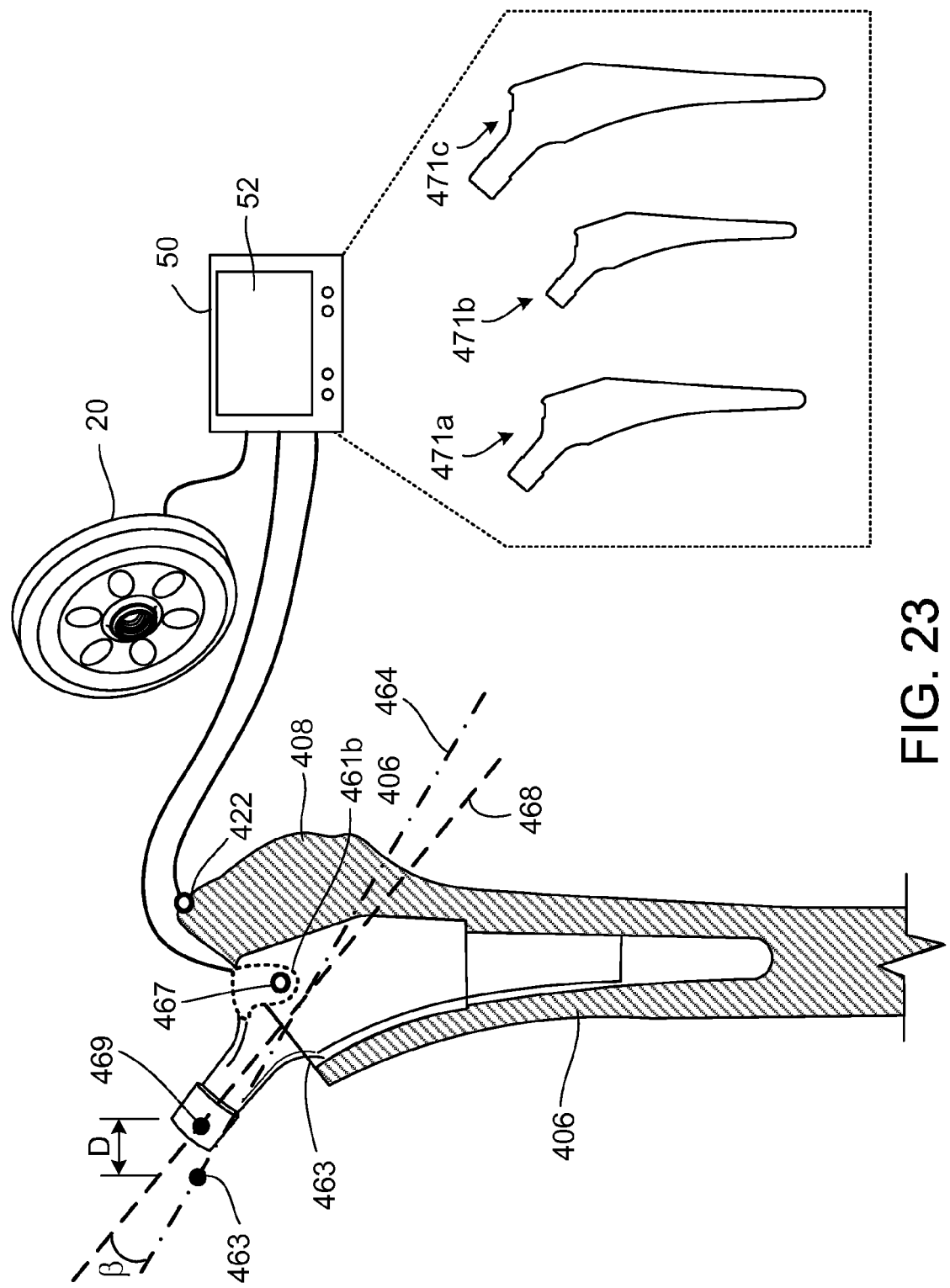

Referring to FIG. 23, the surgeon selects a trial component 463, which may or may not have been suggested by the control unit 50, and indicates on the user interface 52 which trial component 463 is selected. For example, the surgeon enters a product code for the trial component 463 or a corresponding implant, or selects from among options displayed on the user interface 52. If modular components or adjustable components are used, the surgeon indicates the particular combination or configuration of components used.

The surgeon inserts the trial component 463 in the femur 406. The surgeon also attaches a third EM sensor 467 at the landmark 461b. The sensor 467 can be attached to the trial component 463 before or after the trial component 463 is inserted in the femur 406. The landmark 461b can be, for example, a location in a bore configured to receive a screw or other fastener. To achieve a known position at the landmark 461, a housing of the sensor 467 can engage a bottom of the bore. Alternatively, a portion of the housing of the sensor 467 can engage the trial component 463 to be level with an exterior surface of the trial component. The control unit 50 accesses information indicating the location of the landmark 461b on the trial component 463. For example, the surgeon can input information identifying the landmark 461b. Alternatively, the surgeon can select a landmark 461b suggested by control unit 50.

The control unit 50 accesses data indicating the characteristics of the trial component 463 from the trial component library. The data indicates, for example, an offset between the landmark 461b and a neck axis 468 of the trial component 463 and an offset between the landmark 461b and a point 469 of the trial component 463 corresponding to a center of rotation. Because the third sensor 467 is located at the landmark 461b, the offsets can be used to determine the position of the neck axis 468 and the point 469 relative to the position indicated by signals produced by the third sensor 467.

When the trial component 463 is coupled to the joint 400, the trial component 463 defines new properties for the joint 400. For example, one property is a new femoral axis coinciding with the neck axis 468 of the trial component 463. When the trial component 463 is coupled to the femur 406, the neck axis 468 replaces the natural neck axis (e.g., the guide pin axis 464) of the femur 406. Another property of the joint 400 defined by the trial component 463 is a new center of rotation point for the joint 400. With the trial component 463 installed, the joint 400 has a new center of rotation point, defined by the characteristics of the trial component 463 to be located at the point 469.

To determine whether the new properties of the joint 400 are acceptable, the surgeon brings the femur 406 near the identifier 20 such that the second sensor 422 and the third sensor 467 are within the working volume of the EM field generator 21. The control unit 50 determines the position of the third sensor 467 relative to the second sensor 422 based on the signals produced by the sensors 422, 467. Using the offsets accessed from the data in the trial component library, the control unit 50 determines the position of the neck axis 468 and the center of rotation point 469 relative to the first sensor 420. While the trial component 463 is coupled to the femur 406 in the current position, these positions represent current properties of the joint 400.

The control unit 50 compares the current position of the neck axis 468 with the position of the preferred neck axis 464, determining, for example, one or more angular and translational offsets. For example, the control unit 50 can determine an angle, $\beta$, that represents a difference in the angle of inclination between the neck axis 468 and the preferred neck axis 464. The control unit 50 also compares the location of the center of rotation point 469 of the trial component 463 with the location of the preferred center of rotation point 432 for the joint 400, determining an offset, D, between the locations. Thus the control unit 50 determines differences between the initial properties of the joint 400 and the properties of the joint 400 achieved with the trial component 463 coupled at its current position.

In some implementations, the control unit 50 displays on the user interface 52 an illustration of the femur 406 and the trial component 463, and displays the positions of the axes 464, 468 and the points 432, 469. The control unit 50 also indicates the differences between the preferred positions and the positions achieved by the trial component 463.

The control unit 50 determines whether the characteristics of the current trial component 463 are within an acceptable tolerance from the preferred characteristics. For example, the control unit 50 can compare the difference between the first property and the second property to a threshold. If the calculated difference satisfies the threshold, the control unit 50 indicates on the user interface 52 that the current trial component 463 provides acceptable joint characteristics.

If the characteristics of the trial component 463 are not acceptable, the control unit 50 compares the current characteristics of the trial component 463 to a range of other joint characteristics achievable with the same trial component 463 through adjustment or addition of a particular modular component, such as a ball head with particular characteristics. The control unit 50 determines whether a particular ball head or adjustment to the trial component 463 can achieve the preferred joint characteristics. If so, the control unit 50 identifies the component or adjustment that produces the preferred characteristics and indicates the component or adjustment on the user interface 52. When a modular implant system is used, the control unit 50 can indicate one or more combinations of components that achieve the desired joint characteristics.

If no component or adjustment described in the trial component library can produce the preferred joint characteristics with the trial component 463, the control unit 50 indicates that the trial component 463 is unacceptable. The control unit 50 can also indicate a reason that the trial component is unacceptable, for example, because the neck is 4 mm too short.

Using the data in the trial component library, the control unit 50 identifies a second trial component that can achieve the preferred joint characteristics. For example, the control unit 50 accesses trial component models 471a-471c in the trial component library to select a trial component that most closely produces the preferred joint characteristics and satisfies the surgeon's preferences. The control unit 50 can select the second trial component, for example, one corresponding to the model 471c, to correct for the offsets, $\beta$, D, from the preferred joint center of rotation 432 and the preferred neck axis 464 that resulted from using the trial component 463.

If the trial component 463 is unacceptable, the surgeon removes it from the femur 406 and removes the sensor 467 from the trial component 463. The surgeon inserts a new trial component in the femur 406, for example, a trial component corresponding to the model 471c that the control unit 50 determined to be most likely to achieve the desired joint characteristics. The surgeon inserts the third sensor 467 at a landmark of the second trial component, and uses the control unit 50 to compare the characteristics of the second trial component relative to the preferred joint characteristics in the same manner as described above for the first trial component 463.

The surgeon can repeat the trialing process until a trial component with acceptable characteristics is identified. The surgeon can then reduce the joint 400 with the appropriate trial component and a ball head in place to measure the range of motion of the joint, including using the techniques described below with respect to FIGS. 26A and 26B. When the surgeon is satisfied that the joint 400 exhibits the appropriate characteristics with a particular trial component, the surgeon selects a permanent implant having the same features as the selected trial component, and installs the permanent implant in place of the trial component.

In some implementations, rather than attaching a sensor at a landmark of a trial component, a sensor can be attached to a broach or other instrument used to install the trial component. When the trial component is correctly placed in the femur 406, the surgeon uses the control unit 50 to determine the position of the sensor on the broach relative to the sensor 422 on the femur 406. The control unit 50 can use a known position of the sensor relative to the broach and a known position of the broach and the trial component to determine positions of the trial component from the position of the sensor attached to the broach.

The trialing techniques described above can also be used for a shoulder joint, for example, to trial humeral implants. In a similar manner as described above, the control unit 50 can use data about humeral trial components to intraoperatively provide information about, among other characteristics, distances between the natural center of rotation of the shoulder joint and the new center of rotation of the shoulder joint with a particular humeral trial component or implant.

(6) Measuring Joint Characteristics

A surgeon can use the system 100 to measure characteristics of a joint. The measured characteristics can be compared with previously measured characteristics for the joint to determine the suitability of a component or to assess the quality of a completed procedure.

Figure 24B:
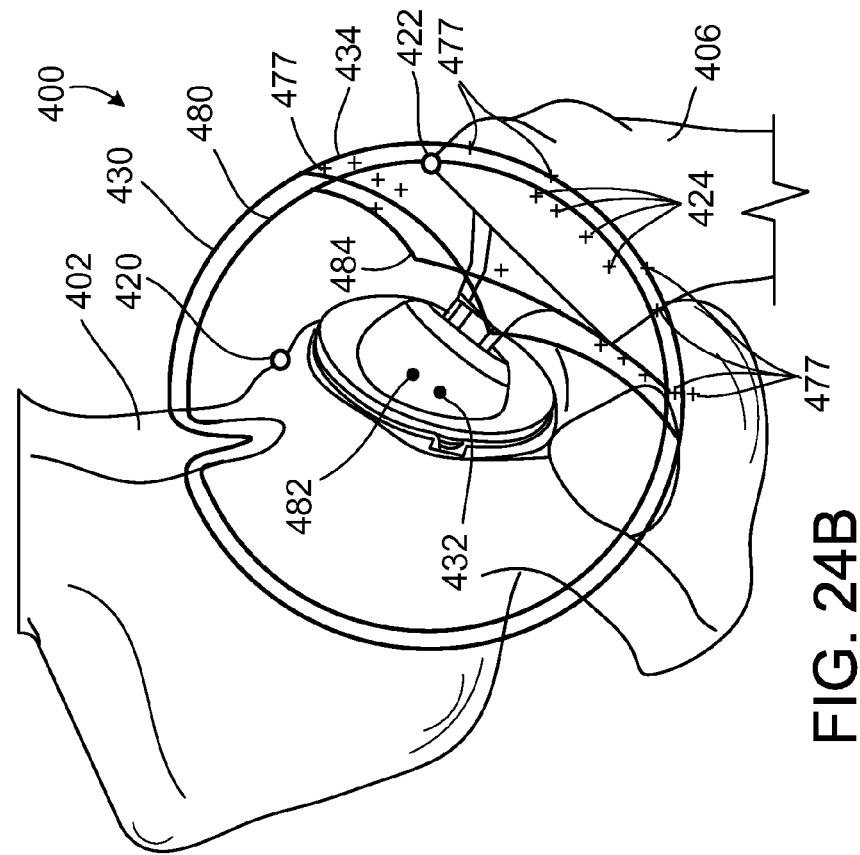
FIGS. 24A and 24B are perspective views illustrating a process for measuring characteristics of a joint.
Figure 24A:
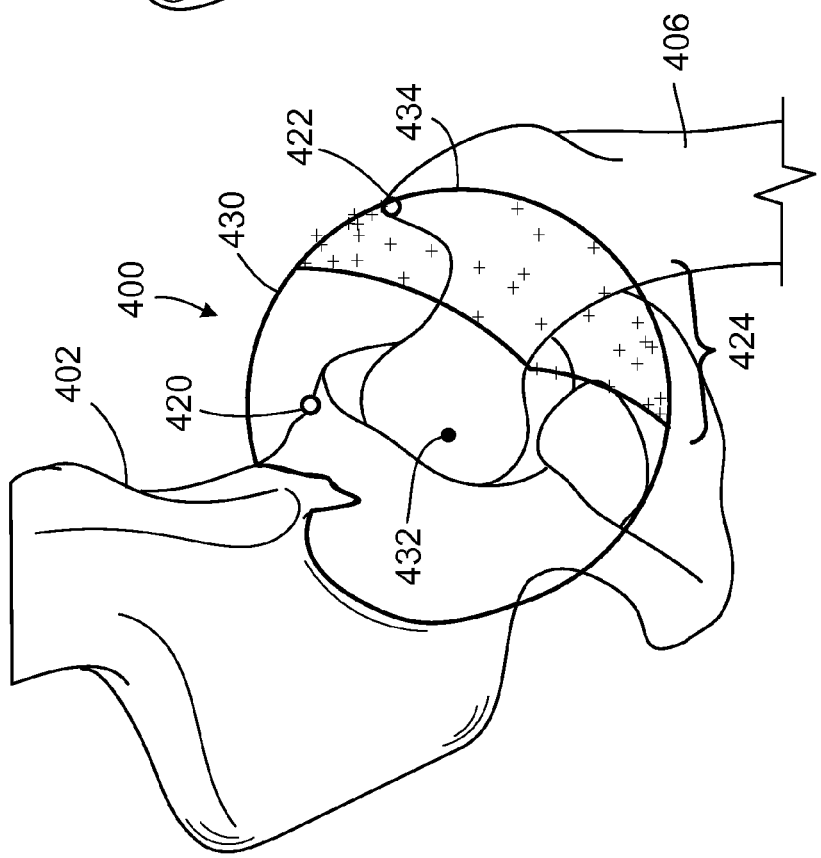

Referring to FIG. 24A, the surgeon uses the control unit 50 to record information indicating the range of motion of the joint 400. The range of motion is recorded, for example, at the beginning of a surgical procedure to indicate the kinematics of the joint 400 prior to adjustments during the procedure. As described above, sensors 420, 422 can be located at positions that are fixed relative to the joint 400, yet moveable relative to each other as the joint 400 moves. As illustrated, the first sensor 420 can be implanted at the pelvis 402, and the second sensor 422 can be implanted at the femur 406. While the sensors 420, 422 are located in the working volume of the EM field generator 21, the surgeon moves the joint 400 through its range of motion. The control unit 50 records a first set of locations 424 of the second sensor 422 relative to the first sensor 420 at different positions of the joint 400, which include positions corresponding to the limits of the range of motion of the joint 400.

The control unit 50 calculates an approximation for the first set of recorded locations of the second sensor 422 relative to the first sensor 420. For example, as described above, the control unit 50 extrapolates the best-fit sphere 430 about the joint 400. The center point 432 of the sphere 430 corresponds to the center of rotation of the joint 400. The control unit 50 also calculates the range of motion surface 434, a portion of the sphere 430 that approximates the region spanned by the first set of locations 424.

In some implementations, the surgeon can also enter parameters on the control unit 50 to indicate a preferred range of motion for the joint 400, which may be different from the range of motion indicated by the surface 434. For example, the surgeon may expand, restrict, shift, or reshape the surface 434 to set a preferred range of motion, according to the need of the patient.

Referring to FIG. 24B, the surgeon moves the joint 400 through a second range of motion, for example, after an adjustment to the joint 400. For example, the second range of motion can be performed after the insertion of a prosthesis or after reconstruction of the joint 400. The second range of motion can be performed after insertion of a trial component to test the suitability of the trial component.

The control unit 50 records a second set of locations 477 of the second sensor 422 relative to the first sensor 420, each corresponding to different positions of the joint 400 through the second range of motion. The second range of motion can be performed with the second sensor 422 at the same position relative to the femur 406 as during movement through the first range of motion. Thus the trajectory traced by the second sensor 422 during the second range of motion can be directly comparable with the trajectory of the second sensor 422 during the first range of motion. Alternatively, if the second sensor 422 has been moved, or if a different sensor is attached to the femur 406, the control unit 50 correlates the locations to shift the recorded locations such that the data is known as if the second sensor 422 had remained in its original position relative to the femur 406.

The control unit 50 calculates an approximation for the second set of locations 477. For example, the control unit 50 extrapolates a second sphere 480 using the second set of locations 477, where the center point 482 of the second sphere 480 corresponds to a current center of rotation of the joint 400. Using the second set of locations 477, the control unit 50 identifies a surface 484 on the second sphere 480 that approximates the new range of motion for the joint 400.

The control unit 50 identifies differences between the original or preferred measured joint characteristics and the later-measured joint characteristics. For example, the control unit 50 determines whether the center point 482 of the second sphere 480 is offset from the center point 432 of the first sphere 430. The control unit 50 also compares the radius of the second sphere 480 with the radius of the first sphere 430 to determine whether the length of the patient's leg has been altered by the procedure. The second sphere 480 is indicated as smaller than the first sphere 430 if the patient's leg has been shortened during the procedure. The control unit 50 determines a difference in leg length, and if the difference in length is zero, the leg has not been altered by the between the measurement of the first set of locations 424 and the second set of locations 477. In addition, the control unit 50 compares the limits of the original range of motion with the limits of the second range of motion, for example, by comparing the second range of motion surface 484 with the original range of motion surface 434.

The control unit 50 indicates the differences between the original range of motion and the current range of motion. For example, the control unit 50 displays a depiction of the calculated spheres 430, 480 or range of motion surfaces 434, 484 about a three-dimensional view of the joint 400. The control unit 50 can also display the center of rotation points 432, 482 and measured locations 424, 477.

When the control unit 50 determines that the current characteristics for the joint 400 differ from the original characteristics for the joint 400, the control unit 50 calculates suggested changes to correct the differences. For example, the control unit 50 determines a suggested offset to correct a shift in the center of rotation of the joint 400, and a suggested adjustment to correct an alteration in leg length. The control unit 50 also indicates adjustments to realign the range of motion indicated by the surface 484 with the surface 434. The control unit 50 indicates the suggested changes to the joint 400 on the user interface 52, allowing the surgeon to adjust the joint 400 to achieve the originally measured characteristics.

After adjustments are made to the joint 400, for example, after adjusting the joint 400 based on the suggested changes indicated on the user interface 52, additional range of motion measurements can be made. The control unit 50 can measure a third set of locations of the sensor 422 relative to the sensor 420, calculate a best-fit sphere and range of motion surface based on the third set of locations, and determine whether the adjustments succeeded in restoring the preferred joint characteristics. Range of motion measurements and comparisons with original joint characteristics can be repeated until the surgeon is confident that the kinematics of the joint 400 match the preferred kinematics of the joint, which may be the kinematics measured prior to the surgical procedure.

(7) Determining Alignments for Revision Procedures

The surgeon can use the system 100 to determine alignments and to select implants for revision arthroplasty procedures. For example, the surgeon can use the system to quickly determine joint characteristics such as the position of a center of rotation of a joint.

Referring to FIG. 25A, the joint 400 is shown after a primary arthroplasty has been completed. A femoral implant 490 is installed at the femur 406, and an acetabular implant 491 is installed in the acetabulum of the joint 400.

For a revision surgery, the surgeon identifies the types of implants 490, 491 installed in the joint 400. For example, the surgeon can identify the product codes or other identifying information for the implants 490, 491. The surgeon inputs information identifying the implants 490, 491 into the control unit 50. The control unit 50 can access an implant library that, like the trial component library, describes the characteristics of multiple implants. The control unit 50 accesses data indicating the characteristics of the implants 490, 491. The surgeon can also input to the control unit 50 additional information about the reconstructed joint 400, such as information identifying a ball component of the joint 400.

The surgeon attaches three EM sensors 481, 483, 485 at the joint 400. The first sensor 481 is attached at a fixed location relative to the pelvis 402, for example on the pelvis 402. The second sensor 483 is located at a fixed location relative to the femur, for example, on the femur 406. The third sensor 485 is attached at a landmark of the femoral implant 490. The surgeon orients the identifier 20 so that the sensors 481, 483, 485 are located within the working volume of the EM field generator 21.

The control unit 50 receives signals from the sensors 481, 483, 485, and determines the positions of the sensors 481, 483, 485 relative to each other. The control unit 50 uses standard characteristics of the femoral implant 490, determined based on data from the implant library, to determine the position of a center of rotation point 493 and a femoral neck axis 494 with respect to the sensors 481, 483, 485.

The control unit 50 determines the center of rotation point relative to both the first sensor 481 and the second sensor 483. Thus when the joint 400 is reduced, the position of the center of rotation point 493 can be known with respect to the pelvis 402 and the femur 406 using different sensors 481, 483.

The surgeon can move the femur 406 into a known alignment relative to the pelvis such that the position of the femoral neck axis 494 has a known position relative to a preferred impaction axis. For example, as described with respect to FIG. 21B, the surgeon moves the femur 406 into a neutral alignment relative to the pelvis 402, in which the femoral neck axis 494 coincides with the preferred impaction axis. In the neutral position of the joint 400, the surgeon uses the control unit 50 to record the position of the sensors 481, 483, 485 relative to each other, and the control unit 50 designates the position of the femoral neck axis 494 while the joint 400 is in the neutral position to be the position of the impaction axis.

In some implementations, rather than aligning the joint 400 in a neutral position to determine the position of the impaction axis, a fourth EM sensor can be attached to a landmark having a known position relative to the acetabular implant 491. The control unit 50 accesses data in the implant library indicating characteristics of the acetabular implant 491, and uses the data to determine the position of the impaction axis relative to the landmark. Because the fourth sensor is located at a known, fixed position relative to the acetabular implant 491, the surgeon can determine the position of the impaction axis along which the acetabular implant 491 was installed using the first sensor 481 and the fourth sensor, without using the position of the femoral neck axis 494.

In addition, when using the fourth sensor to determine the position of the impaction axis, the control unit 50 can be used to determine whether the impaction axis (determined based on the installed position of the acetabular component 491) coincides with the femoral neck axis 494 (determined based on the installed position of the femoral implant 490). The surgeon can position the joint 400 in the neutral position and can use the control unit 50 to compare the position of the femoral neck axis 494 with the position of the impaction axis. The control unit 50 can calculate offsets between the axes and can use the offsets to adjust the preferred axes for the revised joint 400.

Optionally, while the joint 400 is reduced, the surgeon can measure the range of motion of the joint 400 as described with respect to FIG. 24A. The range of motion resulting from the primary arthroplasty can be compared with ranges of motion measured during and after the revision arthroplasty to determine whether an appropriate range of motion has been achieved.

Referring to FIG. 25B, the surgeon dislocates the joint 400, and if the procedure so requires, removes the femoral implant 490. The second sensor 483 remains on the femur 406, such that the position of the original center of rotation point 493 and the original femoral neck axis 494 can are known relative to the femur 406, by virtue of their known position relative to the second sensor 483.

In a similar manner, the surgeon can remove the acetabular implant 491. Because the position of the impaction axis is known relative to the first sensor 481, which remains attached to the pelvis 402, the surgeon can use the system 100 to position instruments and implants relative to the impaction axis.

Figure 26B:
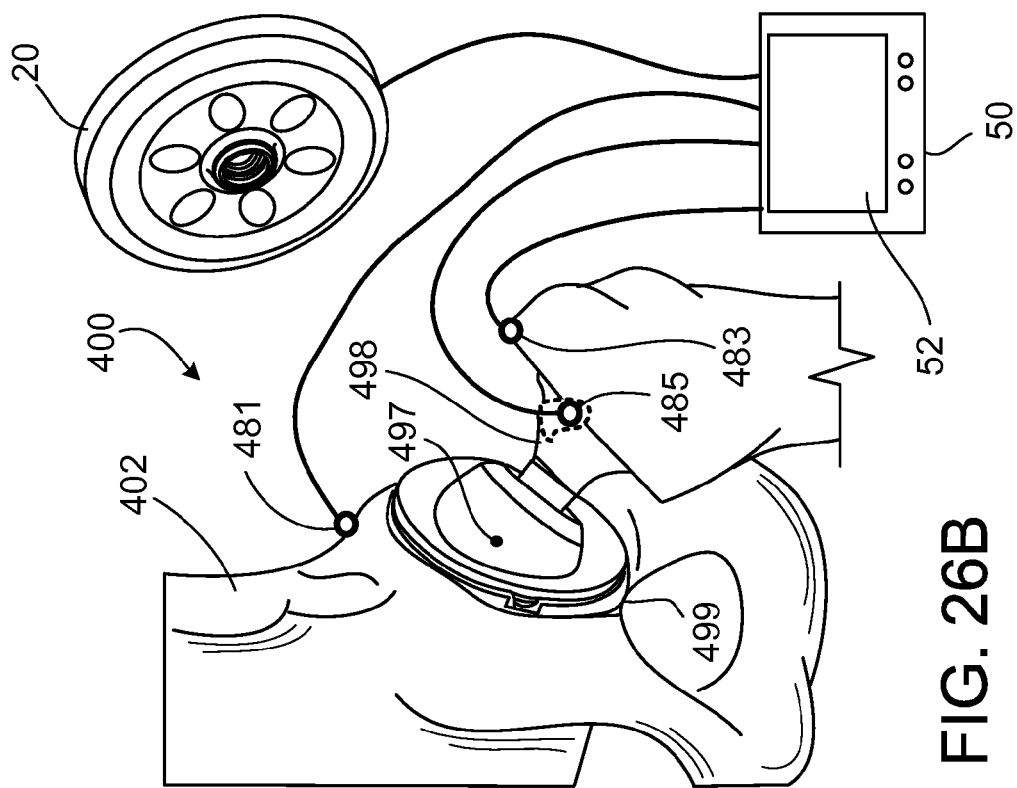
Figure 26A:
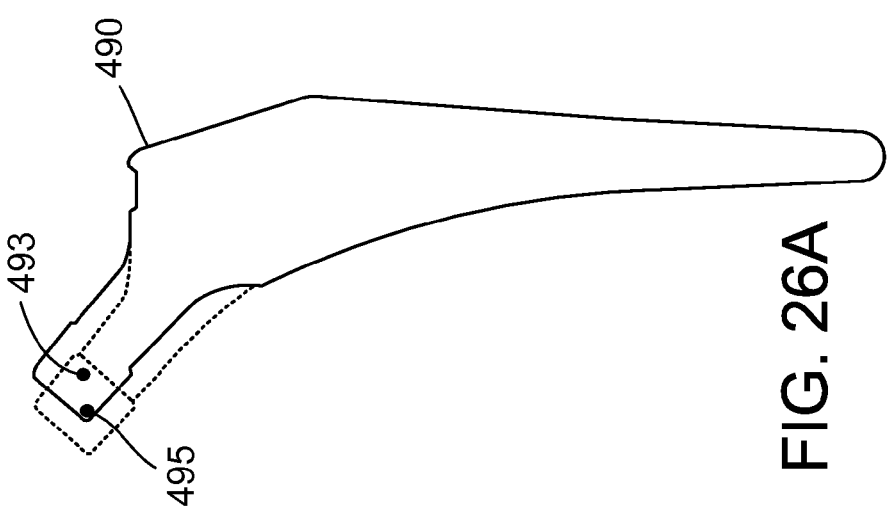

Referring to FIG. 26A, the surgeon can enter offsets on the control unit 50 to alter the desired characteristics of the joint 400. For example, if the center of rotation resulting from of the primary arthroplasty is undesirable, the surgeon can set a new center of rotation point 495 by indicating an offset from the previous center of rotation point 493. The control unit 50 uses the techniques described above to select trial components and implants that achieve the desired joint characteristics. For example, the control unit 50 can identify and suggest new implants that achieve the new center of rotation point for the joint 495.

Referring to FIG. 26B, after the surgeon completes the trialing phase of the procedure, the surgeon installs a femoral implant 498 and an acetabular implant 499. The surgeon reduces the joint 400 and attaches the sensor 485 at a landmark of the femoral component 485. The surgeon uses the control unit 50 to determine one or more characteristics of the joint 400 based on the position of the sensor 485 and the known characteristics of the femoral implant 498. For example, the control unit 50 calculates the location of the current center of rotation point 497 and compares it with the location of the center of rotation point 493 of the joint 400 before the revision arthroplasty. Thus the surgeon can compare characteristics of the joint 400 after the revision to the characteristics of the joint from the primary arthroplasty to determine whether the goals of the revision have been achieved and whether additional adjustments should be made.

Combinations of the above techniques can be used. When beginning an arthroplasty procedure, the control unit 50 can display a list of options to permit the surgeon to customize the procedure. For example, the control unit 50 can permit the surgeon to select which method the surgeon prefers to use to determine the position of the impaction axis for the joint. As another example, the surgeon may select to use the system 100 for installing an acetabular implant, but select to not use the system 100 for assistance when preparing a femur to receive a femoral implant. The control unit 50 thus permits the surgeon can create a customized surgical plan by selecting "a la carte" options at the beginning of the procedure. During the procedure, the control unit 50 streamlines the procedure by omitting steps and functionality that are not desired by the surgeon.

Referring to FIG. 27, the control unit 50 includes an input module 110, a processing module 120, and an output module 130. The control unit 50 also includes a control module 140, a communication module 150, and a power supply (not shown). Although the functions of the control unit 50 are described as modules, the functions need not be performed by separate components. For example, a single processor may perform operations to enable the functionality of multiple modules. As another example, a single component or interface may provide both input and output functionality.

The input module 110 includes a sensor interface 112 to receive signals from EM field sensors. The sensor interface 112 can include a wired communication link, a wireless communication link, or both. The sensor interface 112 can also be configured to receive input from other types of sensors, such as infrared sensors, ultrasound sensors, and proximity sensors (such as eddy current sensors). The sensor interface 112 can be used to request and receive calibration data that is stored at a sensor.

The input module 110 also includes user input controls 116, for example, buttons, a keypad, and a touch sensitive surface. The input module 110 can include a wired or wireless interface that permits input to be received from one or more peripheral devices.

The input module 110 optionally includes an identifier input interface 114 to receive input from the identifier 20. In some implementations, the control unit 50 does not require input from the identifier 20. Control signals transmitted by the control unit 50 can be used to determine operating properties of the identifier 20. In other implementations, however, the identifier 20 can provide information through the identifier input interface 114. As described with respect to FIG. 28 below, some identifiers can input data indicating the relative positions of references, and such information can be received over the identifier input interface 114.

The processing module 120 includes one or more processing devices 122 and one or more storage devices 124. The one or more processing devices 122 communicate with the one or more storage devices 124 to record and access data, for example, data received through the input module and data produced as the result of calculations by the one or more processing devices 122. The one or more storage devices 124 store instructions that can be executed by the one or more processing devices 122, causing the one or more processing devices 122 to perform operations as described above. The operations include, for example, determining relative positions between references and calculating the alignments based on the relative positions. The one or more storage devices 124 can include remote storage devices accessed through a network. The one or more storage devices 124 can store, for example, a trial component library, an implant library, data describing characteristics of multiple joints, and other data.

The one or more processing devices 122 generate control signals to control the operation of the identifier 20. The control unit 50 transmits the control signals to the identifier 20 using the control module 140, which includes an interface to communicate with the identifier 20.

The output module 130 includes a display 132 on which the user interface 52 is displayed. In some implementations, the display 132 is a removable or physically separate module from a housing of the control unit 50. The output module 130 can also include a speaker or other device to provide audio output to the user.

The communication module 150 permits the control unit 50 to communicate with other systems over a network. The control unit 50 can thus access data over a network and can transmit data over a network.

Figure 28:
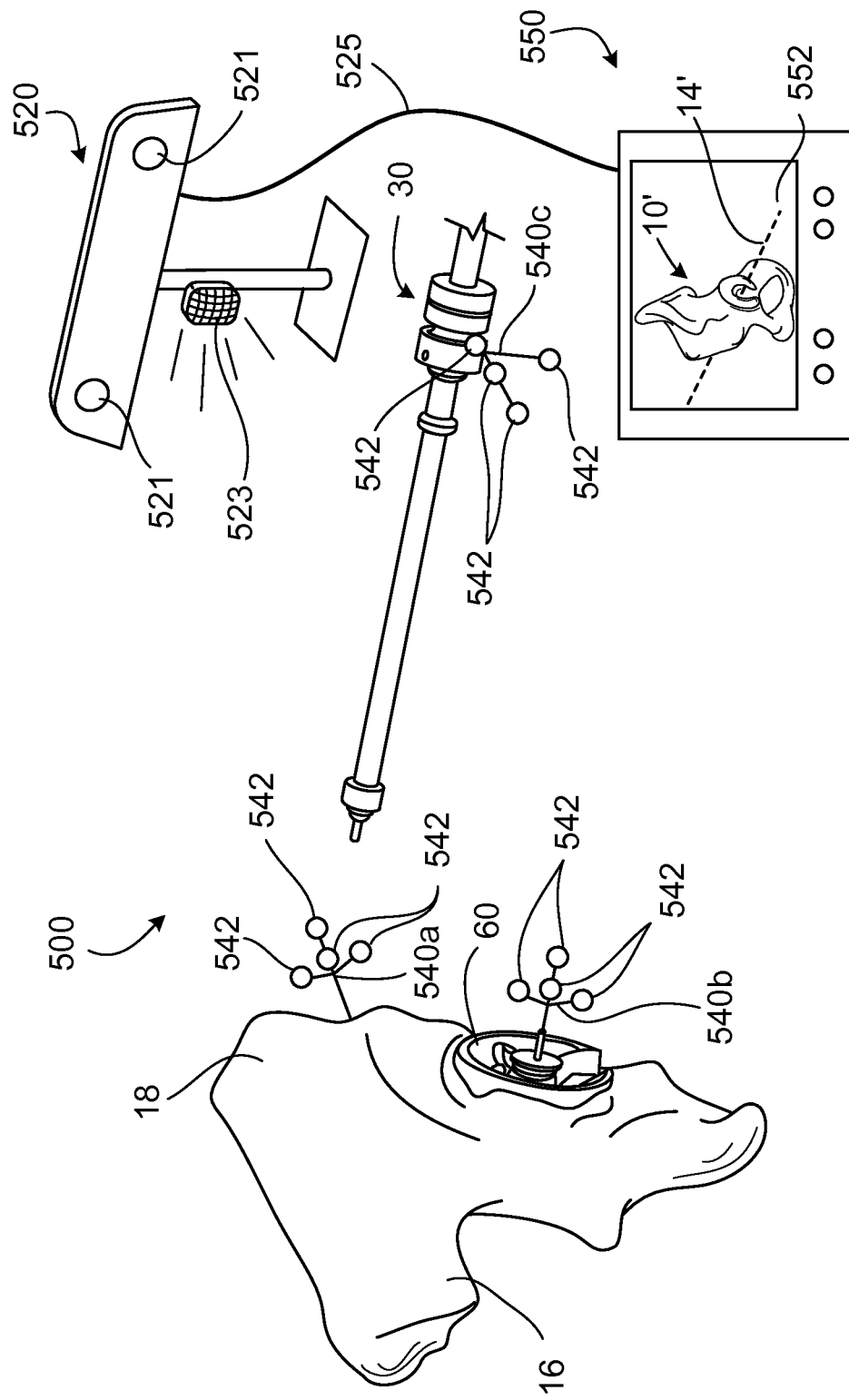
FIG. 28 is an illustration of an alternative alignment system.

Referring to FIG. 28, an alternative alignment system 500 can be used to perform each of the techniques described above. The system 500 includes a control unit 550, an identifier 520, and one or more fiducials, such as infrared reflectors 540a-540c. The identifier 520 and infrared reflectors 540a-540c are references which can be used to determine the relative positions of tissues and instruments during procedures. References in the system 500 can communicate using infrared rather than electromagnetic fields, allowing the control unit 550 to determine relative positions. In some implementations, infrared emitters can be used in addition to, or as alternatives to, the infrared reflectors 540a-540c.

The identifier 520 includes one or more infrared detectors, such as or infrared cameras or imaging devices. For example, the identifier 520 includes two infrared cameras 521. The identifier 520 can also include an infrared emitter 523 to direct infrared toward the infrared reflectors 540a-540c. The identifier 520 can communicate with the control unit 550 over a communication link 525, which may be wired or wireless.

The infrared reflectors 540a-540c can each include infrared reflectors or infrared emitters. For example, as illustrated, each infrared reflector 540a-540c can include an array of infrared-reflecting elements 542, such as spheres, positioned in a plane. Infrared reflected from the infrared-reflecting elements 542 indicates the orientation of the plane in which the spheres 542 are arranged. The identifier 520 directs infrared toward the reflectors of one of the reflectors 540a-540c, and detects infrared reflected from each of the infrared reflectors of the reflector. Based on the detected infrared, the control unit 550 calculates the position of the plane in which the infrared-reflecting elements 542 are positioned. For example, the control unit 550 can use triangulation to calculate the position of the identifier 520 relative to the infrared reflector 540a-540c and the positions of the infrared reflectors 540a-540c relative to each other.

The control unit 550 powers the infrared cameras 521 of the identifier 520 and receives output signals from the infrared cameras 521. Using the output signals from the infrared cameras 521, the control unit 550 determines the positions of the infrared reflectors 540a-540c relative to the identifier 520. The control unit 550 further determines the positions of the reflectors 540a-540c relative to each other and relative to instruments 30 and tissues.

As an example, the preferred trajectory of an impaction axis 14 for the joint 10 can be determined using the system 500, in a similar manner to the techniques described above with respect to FIGS. 3A to 6. The first infrared reflector 540a can be fixed to the iliac crest 18 of the pelvis 16 as a semi-permanent planar reference, meaning, for example, that the infrared reflector 540a remains in position throughout a procedure. The second reflector 540b can be coupled to the acetabular guide 60. The identifier 520 directs infrared toward the reflectors 540a, 540b, and detects the reflected infrared with the infrared cameras 521. The control unit 550 receives information indicating the received infrared, determines the positions of the planes using the information. Based on the position of the second reflector 540b and the plane indicated by the second reflector 540b, the control unit 550 calculates the position of the impaction axis 14 relative to the plane indicated by the first reflector 540a. The third reflector 540c is coupled to the instrument 30, for example, an impactor handle or reamer handle, and the position of the third reflector 540c relative to the instrument 30 is determined relative to the first reflector 540a. The position of the instrument 30 relative to the impaction axis 14 is then indicated on a user interface 552 of the control unit 550. In a similar manner, the other techniques described above can be performed using the identifier 520 and the infrared reflectors 540a-540c of the system 500 rather than using the identifier 20 and the various EM sensors of the system 100.

In addition to the references described above, other types of references may be used. For example, infrared sensors, ultrasound sensors, and proximity sensors (such as eddy current sensors) can be used as references. References generally removed after a procedure is completed. In some implementations, sensors can be sterilized. In other implementations, disposable sensors are used and are discarded after each procedure.

Figure 29:
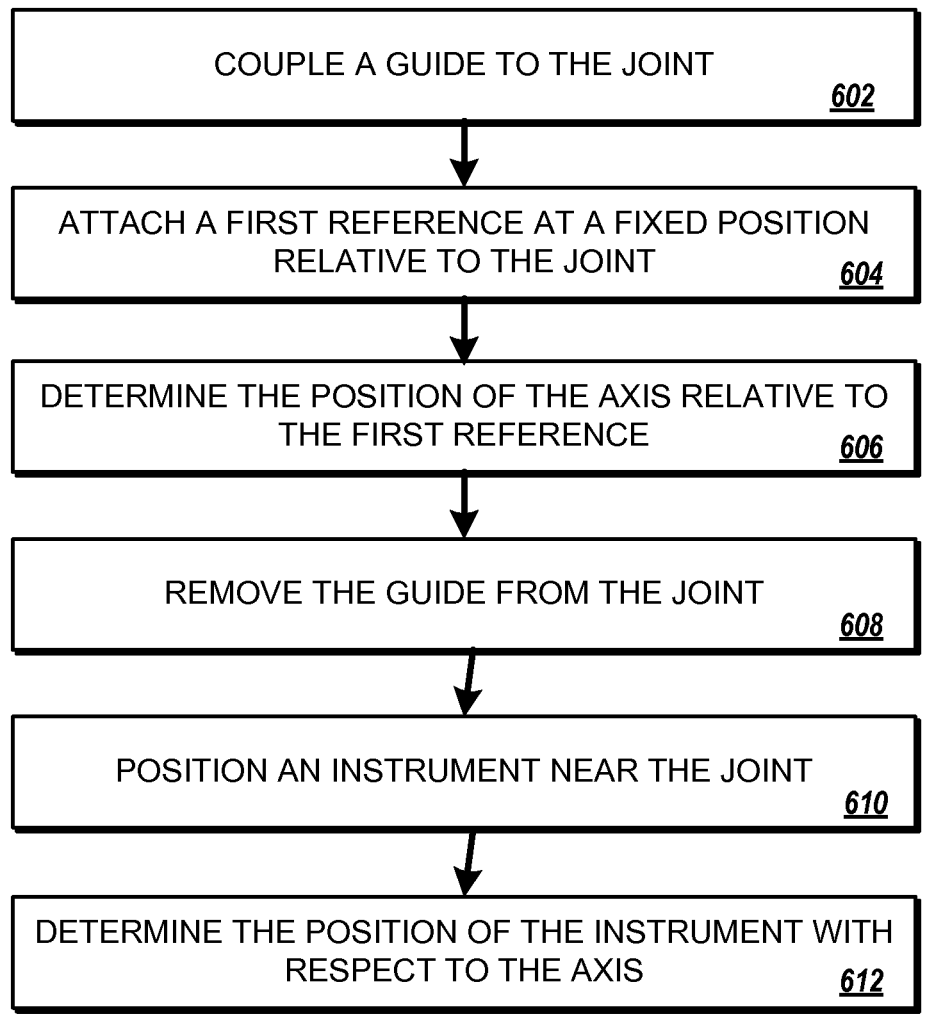

Referring to FIG. 29, a process 600 for determining an alignment relative to a joint can be performed by a surgeon.

The process 600 described below can also include additional features described above, for example, features described with reference to FIGS. 3A to 7B.

A guide is coupled to the joint (602). The guide defines an axis or other alignment, and the guide has outer contours formed to substantially conform to a portion of the joint. The axis defined by the guide can correspond to a known inclination angle and anteversion angle with respect to the joint. The position of the axis can be based on imaging data for the joint. The guide can mate with a receiving portion of the joint in a known orientation. In some implementations, the guide mates with the receiving portion of the joint in a single orientation.

A first reference is attached a fixed position relative to the joint (604). The position of the axis is determined relative to the first reference (606). For example, a surgeon can couple a second reference to an instrument and align the instrument relative to the axis. The surgeon can determine the position of the axis by using a control unit to receive signals indicating the relative position of the second reference and the first reference. The surgeon can initiate operation of the control unit such that the control unit determines and stores the position of the second reference relative to the first reference.

The guide is removed from the joint (608). After the guide is removed from the joint, an instrument is positioned near the joint (610). The position of the instrument relative to the axis is determined based on the position of a second reference relative to the first reference (612). The surgeon can use a control unit to determine the relative position of the second reference and first reference, and to determine the position of the instrument relative to the first reference.

Figure 30:
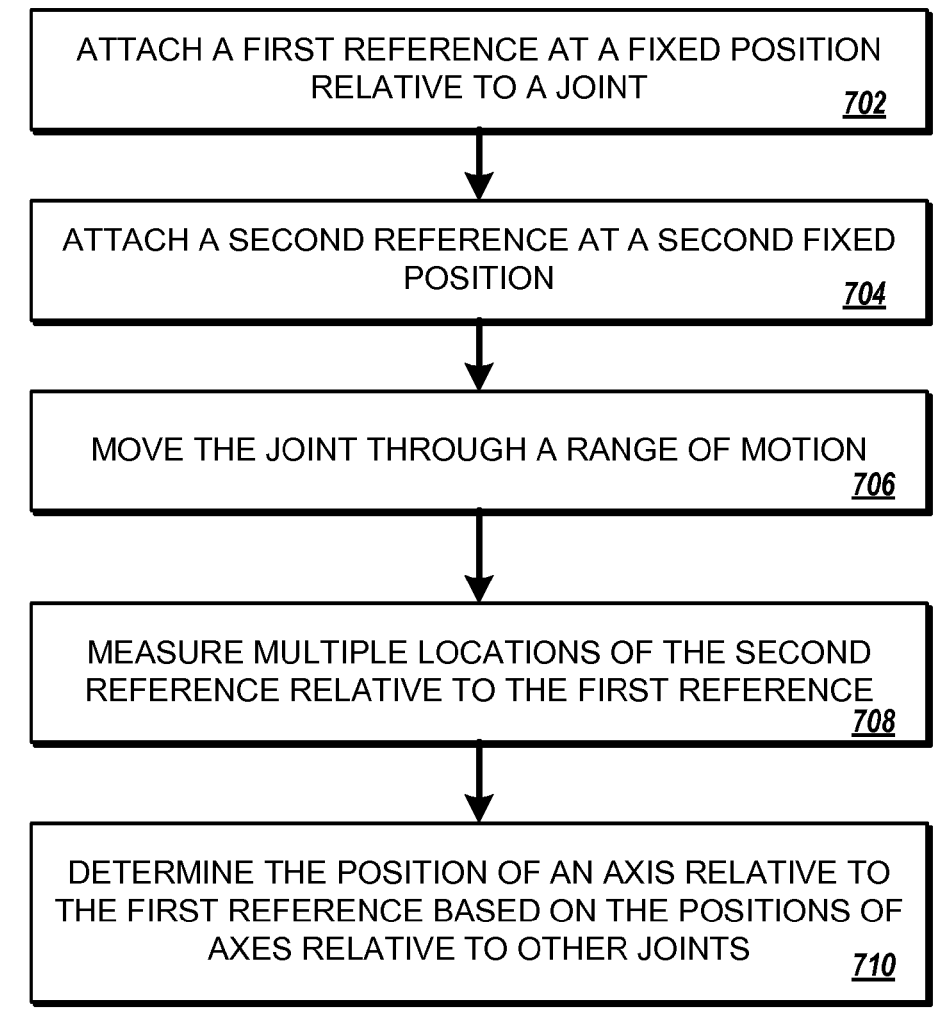

Referring to FIG. 30, a process 700 for determining an alignment relative to a joint can be performed by a surgeon. The process 700 described below can also include additional features described above, for example, features described with reference to FIGS. 14A to 16.

A first reference is attached at a fixed position relative to a joint (702). A second reference is attached at a second fixed position relative to the joint (704). The references can be attached to different bones of the joint. The joint is moved through a range of motion (706). Multiple locations of the second reference relative to the first reference are measured (708). The position of an axis relative to the first reference is determined based on the measured locations and positions of axes relative to other joints.

The surgeon can determine the position of the axis by using a control unit to determine the location of a point substantially corresponding to a center of rotation of the joint based on the measured locations. The surgeon can also use the control unit to access data based on the positions of axes relative to other joints, and determine a second point along the axis using the accessed data. For example, the surgeon can measure the locations using a control unit configured to (i) generate a representation of the range of motion of the joint based on the measured locations, (ii) access a composite representation based on positions of axes relative to other joints, and (iii) determine the position of the axis using correlations between the first representation and the composite representation.

Figure 31:
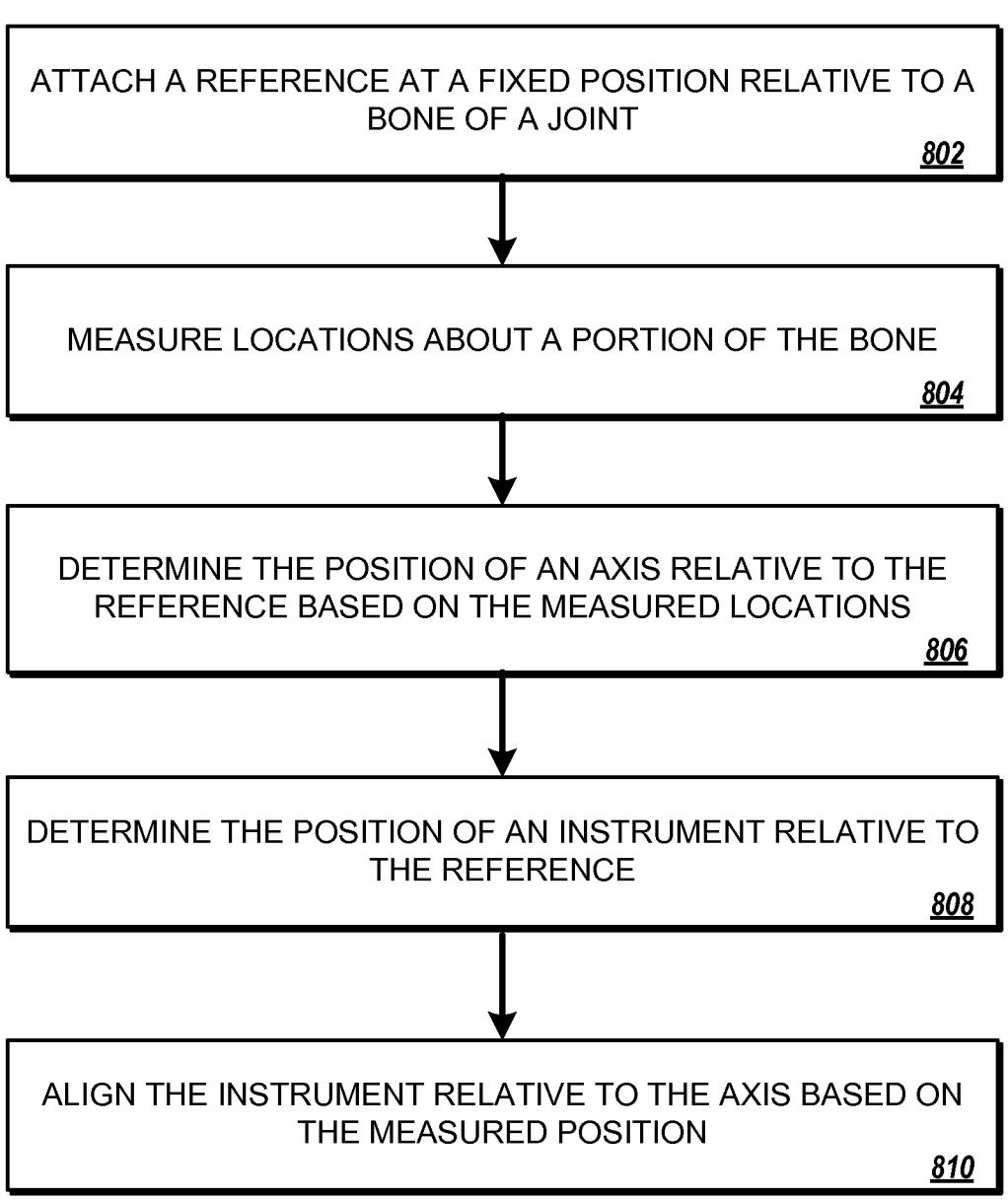

Referring to FIG. 31, a process 800 for determining an alignment relative to a joint can be performed by a surgeon. The process 800 described below can also include additional features described above, for example, features described with reference to FIGS. 17 to 20.

A reference is attached at a fixed position relative to a bone of a joint (802). Locations about a portion of the bone are measured (804). The locations are measured such that locations are known relative to the reference. The locations can be measured about the neck of a femur or neck of a humerus. The position of an axis is determined relative to the reference based on the measured locations. The axis can be a substantially central axis through the neck of the femur or neck of the humerus. The surgeon can determine the position of the axis using a control unit configured to generate a cylindrical representation based on the measured locations and to determine a substantially central axis of the cylindrical representation.

The position of an instrument is determined relative to the reference (808). The surgeon can determine the position of the instrument using a control unit configured to determine the position of a second reference relative to the reference, where the second reference is attached to the instrument. The instrument is aligned relative to the axis using the position of the instrument relative to the reference (810).

Figure 32:
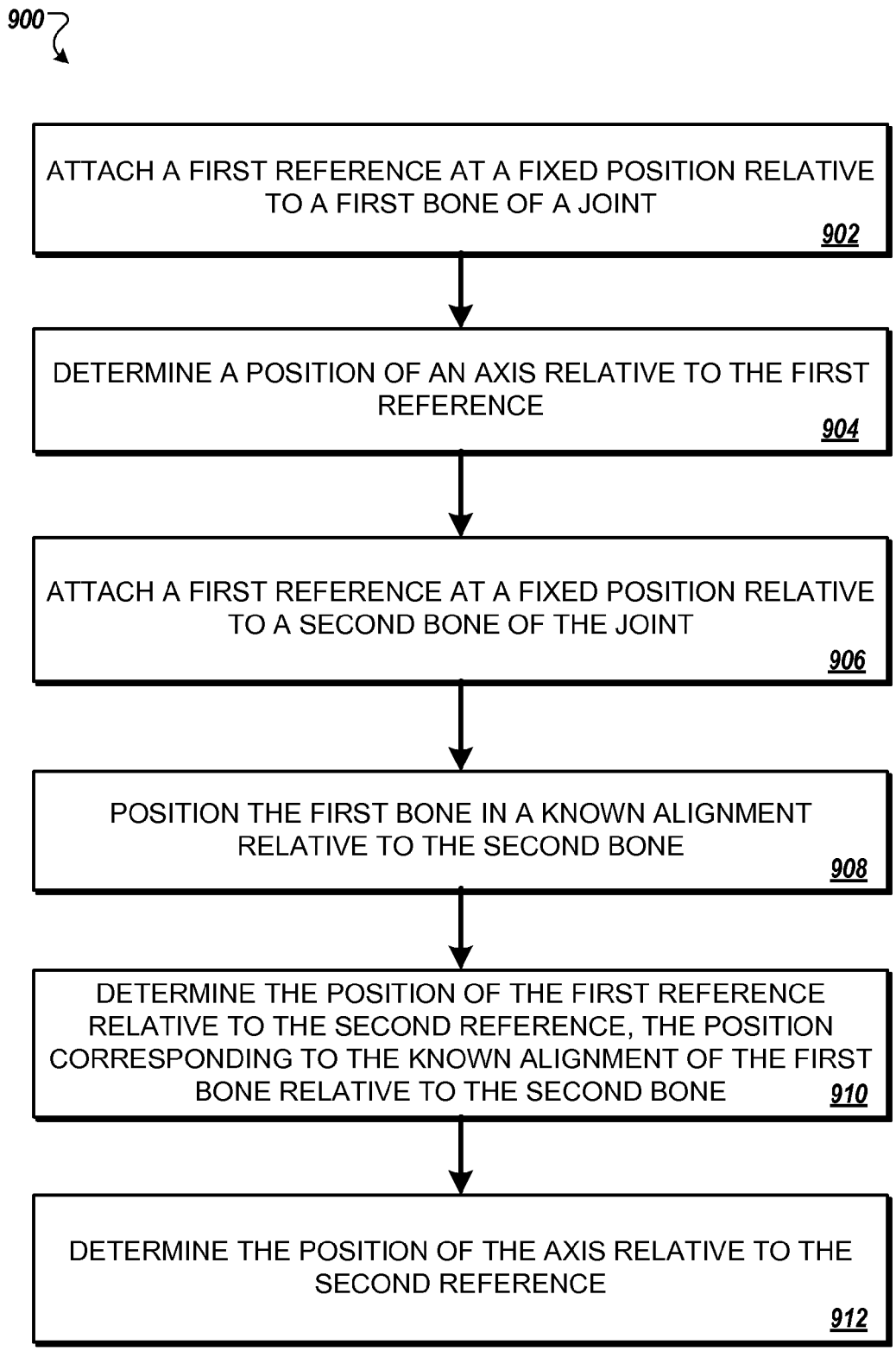
FIGS. 32 and 41 are flow diagrams illustrating example processes for determining an alignment relative to a joint.

Referring to FIG. 32, a process 900 for determining an alignment relative to a joint can be performed by a surgeon. The process 900 described below can also include additional features described above, for example, features described with reference to FIGS. 21A to 21B.

A first reference is attached at a fixed position relative to a first bone of a joint (902). The position of an axis is determined relative to the first reference (904). A second reference is attached at a fixed position relative to a second bone of the joint (906). The first bone is positioned in a known alignment relative to the second bone (908). The position of the first reference relative to the second reference corresponding to the known alignment of the first bone relative to the second bone is determined (910). For example, the relative position of the first reference and second reference can be measured while the first bone is aligned relative to the second bone in the known alignment. The position of the axis is determined relative to the second reference (912). The position of the axis can be determined based on (i) the position of the first reference relative to the second reference, and (ii) the position of the axis relative to the first reference.

Figure 33:
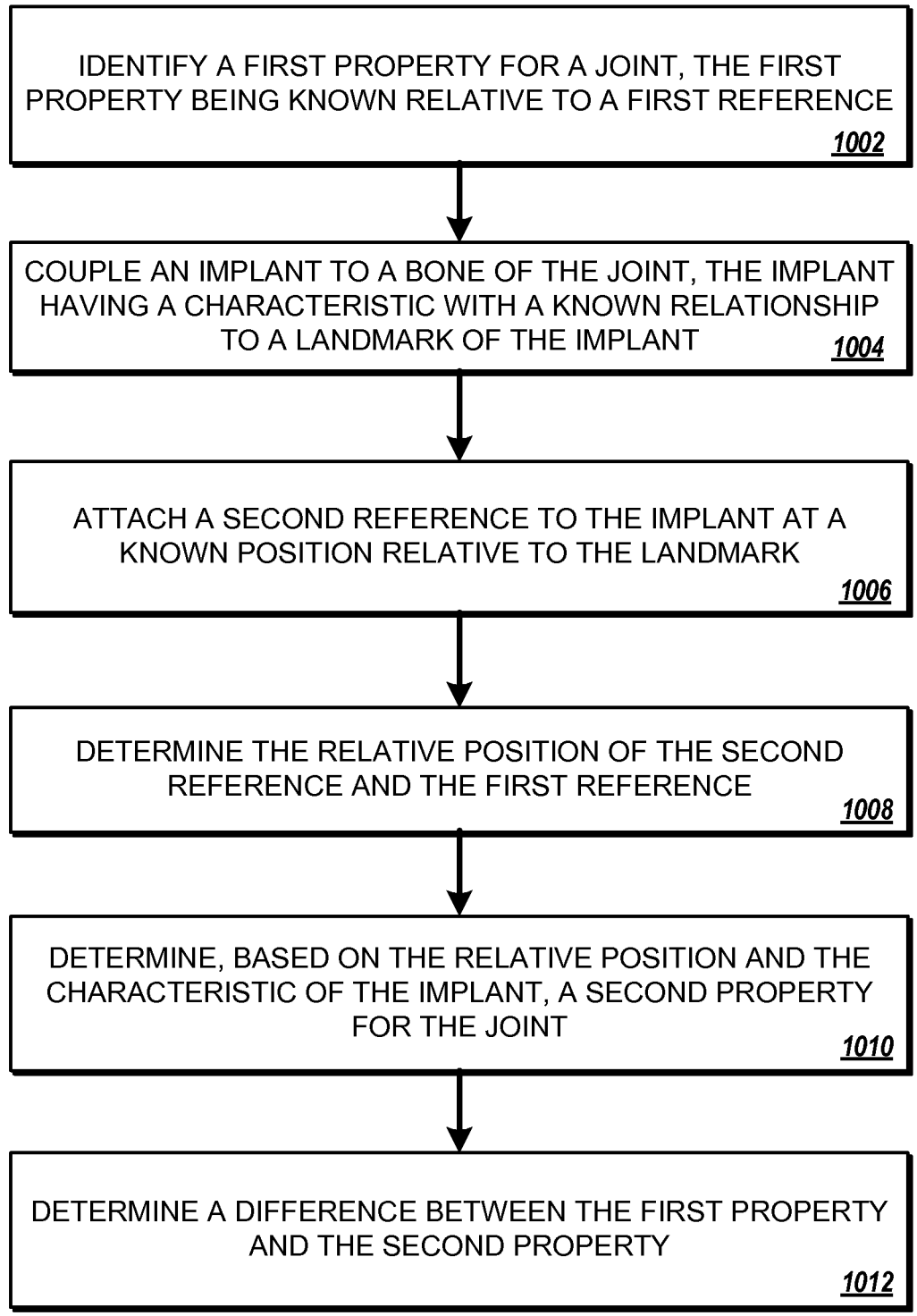
FIGS. 33 and 42 are flow diagrams illustrating example processes for determining the suitability of trial implants.

Referring to FIG. 33, a process 1000 for selecting an implant can be performed by a surgeon. The process 1000 described below can also include additional features described above, for example, features described with reference to FIGS. 22A, 22B, and 23.

A first property for a joint is identified (1002). The first property can be, for example, a center of rotation point or an axis of the joint. The first property is known relative to a first reference, and the first reference is located at a fixed position relative to the bone. An implant is coupled to the bone (1004). A characteristic of the implant has a known relationship relative to a landmark of the implant, for example, a known position relative to the landmark. The characteristic of the implant can be, for example, a neck angle, a location of the implant corresponding to a joint center of rotation, a neck length, a dimension of the implant, or a position of an axis defined by the implant, and the known relationship relative to the landmark is a known position relative to the landmark. The process 1000 can include determining the characteristic of the implant. The surgeon can use the control unit to access data indicating the characteristic and its relationship to the landmark.

A second reference is attached to the implant at a known position relative to the landmark (1006), for example, at the landmark. The relative position of the second reference and the first reference is determined (1008). Based on the relative position and the characteristic of the implant, a second property for the joint is determined (1010). The second property can be defined by the implant. For example, the second property can be a center of rotation of the joint resulting from the position of the implant at the bone. Differences between the first property and the second property are determined (1012).

The first property and the second property can each a neck angle, a neck length, a location of a joint center of rotation, or a position of an axis of a neck. For example, the first property can be a location of a natural center of rotation of the joint, and the second property can be a location of center of rotation of the joint defined by the implant when coupled to the bone. As another example, the bone can be a femur, the first property can be a position of an axis defined by a neck of the femur, the characteristic of the implant can be the position of an axis defined by a neck of the implant, and the second property can be the position of an axis defined by the neck of the implant when the implant is coupled to the femur.

Figure 34:
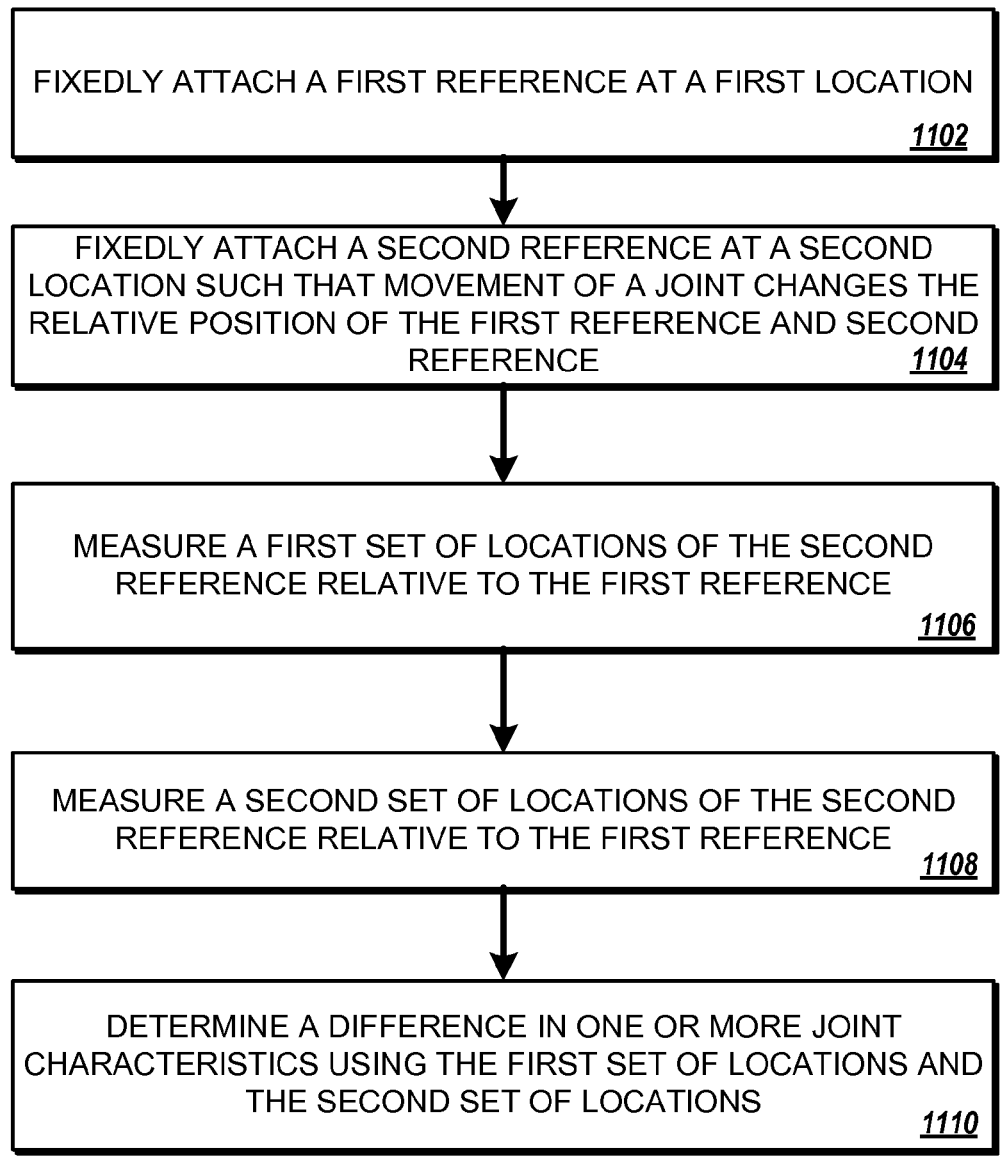
FIGS. 34 and 43 are flow diagrams illustrating example processes for determining differences in joint characteristics.

Referring to FIG. 34, a process 1100 for determining joint characteristics can be performed by a surgeon. The process 1100 described below can also include additional features described above, for example, features described with reference to FIGS. 24A to 24B.

A first reference is fixedly attached at a first location (1102), for example, at a bone of a joint. A second reference is fixedly attached at a second location such that movement of the joint changes the relative position of the second reference and the first reference (1104). A first set of locations of the second reference relative to the first reference (1106). The first set of locations can include relative locations of the references corresponding to different positions of the joint, including positions of the joint at extremities of the range of motion of the joint. A second set of locations of the second reference relative to the first reference is measured (1108). The second set of locations can include relative locations of the references corresponding to different positions of the joint, including positions of the joint at extremities of the range of motion of the joint. A difference in one or more joint characteristics is determined using the first plurality of locations and the second plurality of locations (1110). The first set of locations can be measured before a surgical procedure, and the second set of locations can be measured after the surgical procedure. Thus the difference in one or more joint characteristics can be a difference caused by the surgical procedure.

Figure 35:
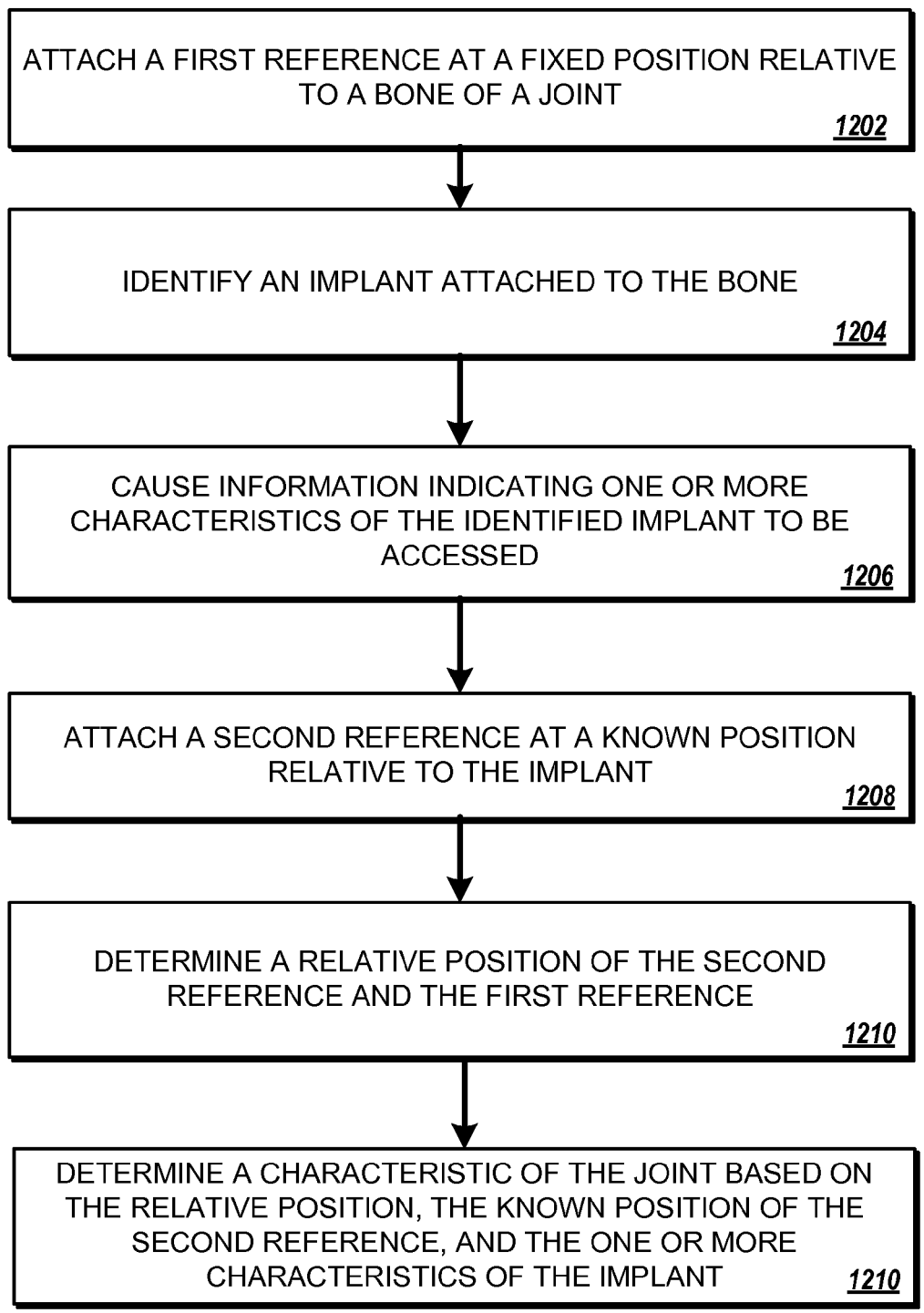
FIGS. 35 and 44 are flow diagrams illustrating example processes for determining characteristics of a joint including an implant.

Referring to FIG. 35, a process 1200 for determining an alignment for a revision surgery can be performed by a surgeon. The process 1200 described below can also include additional features described above, for example, features described with reference to FIGS. 25A to 26B.

A first reference is attached at a fixed position relative to a bone of a joint (1202). An implant attached to the bone is identified (1204). Information indicating one or more characteristics of the identified implant is accessed (1206). For example, the surgeon can cause the information to be accessed by inputting to a control unit information identifying the identified implant, or by selecting a control requesting that characteristics be accessed. A second reference is attached at a known position relative to the implant (1208). For example, the second reference can be attached at a landmark of the implant. A relative position of the second reference and the first reference is determined (1210). For example, the surgeon can use a control unit to determine the relative position of the references. A characteristic of the joint is determined based on the relative position, the known position of the second reference, and the one or more characteristics of the implant (1212). The characteristic can be, for example, the position of a center of rotation of the joint or an axis defined by of the implant.

Referring to FIG. 36, a process 1300 can be performed, for example, by one of the control units 50, 550, to determine an alignment of an instrument relative to a joint. The process 1300 can also include additional features described above, for example, features described with reference to FIGS. 3A to 7B.

Information indicating a position of a first reference relative to a second reference aligned relative to an axis is received (1302). The first reference is attached at a fixed location relative to a joint. The second reference is aligned at a known position relative to the axis, which is defined by a guide coupled to the joint. The guide is formed prior to used such that the outer contours of the guide substantially conform to a portion of the joint. For example, the guide can be an acetabular guide 60 formed to substantially conform to the contours of the acetabulum of a particular hip joint. The axis can be an impaction axis 14 determined for the joint based on imaging data, such as tomography data, for the particular hip joint to which the guide conforms.

The position of the axis is determined relative to the first reference (1304). The position of the axis is determined using the known position of the second reference relative to the axis and the information indicating the position of the first reference relative to the second reference. For example, an offset between the position of the second reference can be determined and used to calculate the position of the axis relative to the first reference.

Information indicating the position of an instrument relative to the first reference is received (1306). For example, a third reference can be coupled to the instrument, and information indicating the position of the third reference relative to the first reference can be determined. The information can be generated after the guide is uncoupled from the joint, and can indicate a position of the instrument when the instrument is uncoupled from the joint.

The position of the instrument is determined relative to the axis (1308). For example, the position of the instrument is compared with the position of the axis determined in (1304), with both positions being known relative to the same first reference. The position of the instrument can be determined after the guide is uncoupled from the joint.

The process 1300 can include determining the location of a center of rotation point for the joint relative to the first reference. The center of rotation point can be known relative to the guide when the guide is coupled to the joint. Based on the known location of the center of rotation point relative to the guide, and the known position of the second reference relative to the guide, and the information indicating the position of the first reference relative to the second reference, the location of center point relative to the first reference is determined. The position of the center of rotation point can be used to determine a preferred reaming depth for the joint, for example, based on known characteristics of an implant for the joint.

Figure 37:
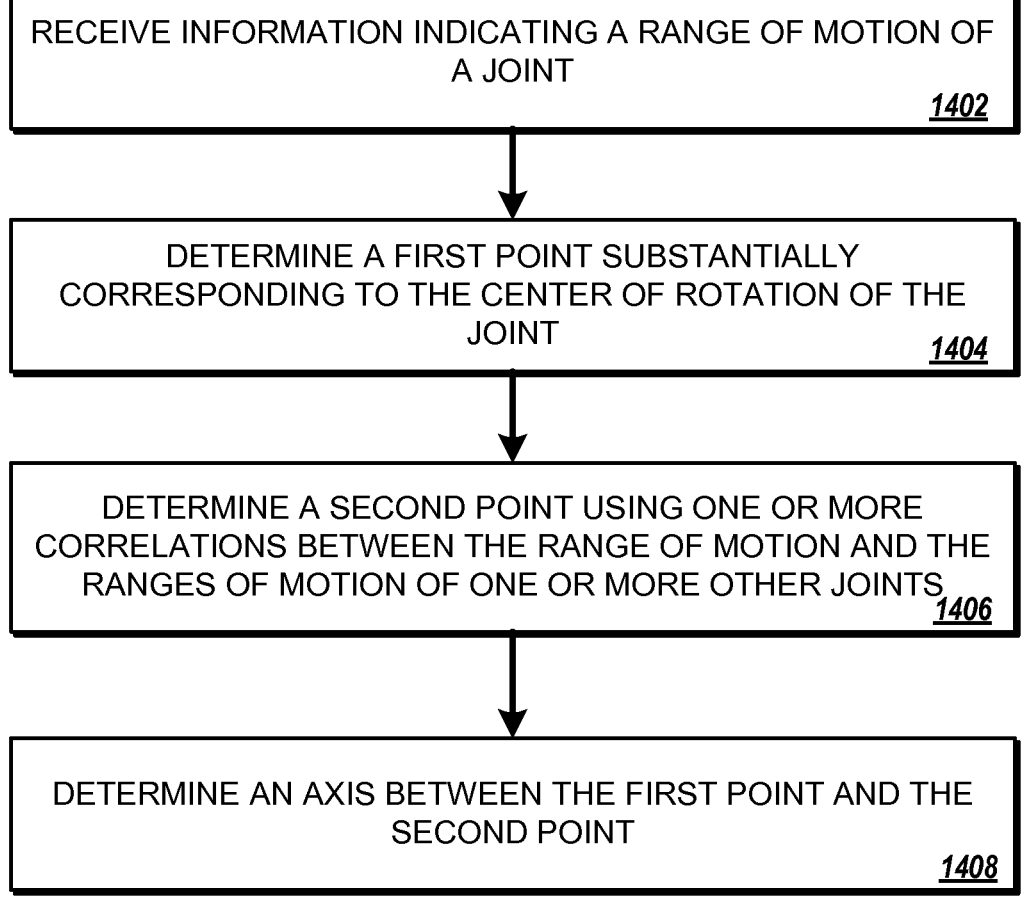

Referring to FIG. 37, a process 1400 can be performed, for example, by one of the control units 50, 550, to calculate the position of an axis relative to a joint. The process 1300 can also include additional features described above, for example, features described with reference to FIGS. 8 to 16.

Information indicating a range of motion of a joint is received (1402). The information can include a plurality of locations 424, where each of the plurality of locations 424 corresponds to a different position of the joint. The information can additionally or alternatively include representation of the range of motion, such as a surface 434 defined in a three-dimensional coordinate system. The information can indicate one or more extremities of the range of motion of the joint.

A first point substantially corresponding to the center of rotation of the joint is determined (1404). The location of first point can be calculated using the information indicating the range of motion. For example, the first point can be a focal point or center point of a surface 434 representing the range of motion of the joint. The information indicating the range of motion of the joint can be known relative to a reference, and the location of the first point can be determined relative to the same reference.

A second point is determined using one or more correlations between the range of motion and second ranges of motion of one or more other joints (1406). The second point can be determined using composite information representing commonalities among ranges of motion and axes for multiple joints.

The correlations can include relationships identified between the range of motion and the second ranges of motion, such as commonalities and identified corresponding landmarks. Correlations can also include calculated positional offsets between the boundaries of the range of motion and the boundaries of the second ranges of motion, such as offsets to align the boundaries at a least-error orientation. For example, the correlations can be used to align the range of motion of the joint with the second ranges of motion in a three-dimensional coordinate system. The alignment can be based on ordinary least squares or geometric least squares in three dimensions for points along the boundaries of the ranges of motion and/or other points and regions indicating the range of motion.

Determining the second point using the correlations can include using positions of axes known relative to the second ranges of motion to determine one or more corresponding positions relative to the range of motion. When the range of motion and the second ranges of motion are aligned based on the correlations in a common coordinate reference frame, the positions of the axes for the second ranges of motion are aligned at the corresponding positions relative to the range of motion.

An axis between the first point and the second point is determined (1408). For example, an axis intersecting the first point and the second point is defined relative to a first reference which is located at a fixed position relative to the joint. The axis can be, for example, an impaction axis 446 determined as described above.

Figure 38:
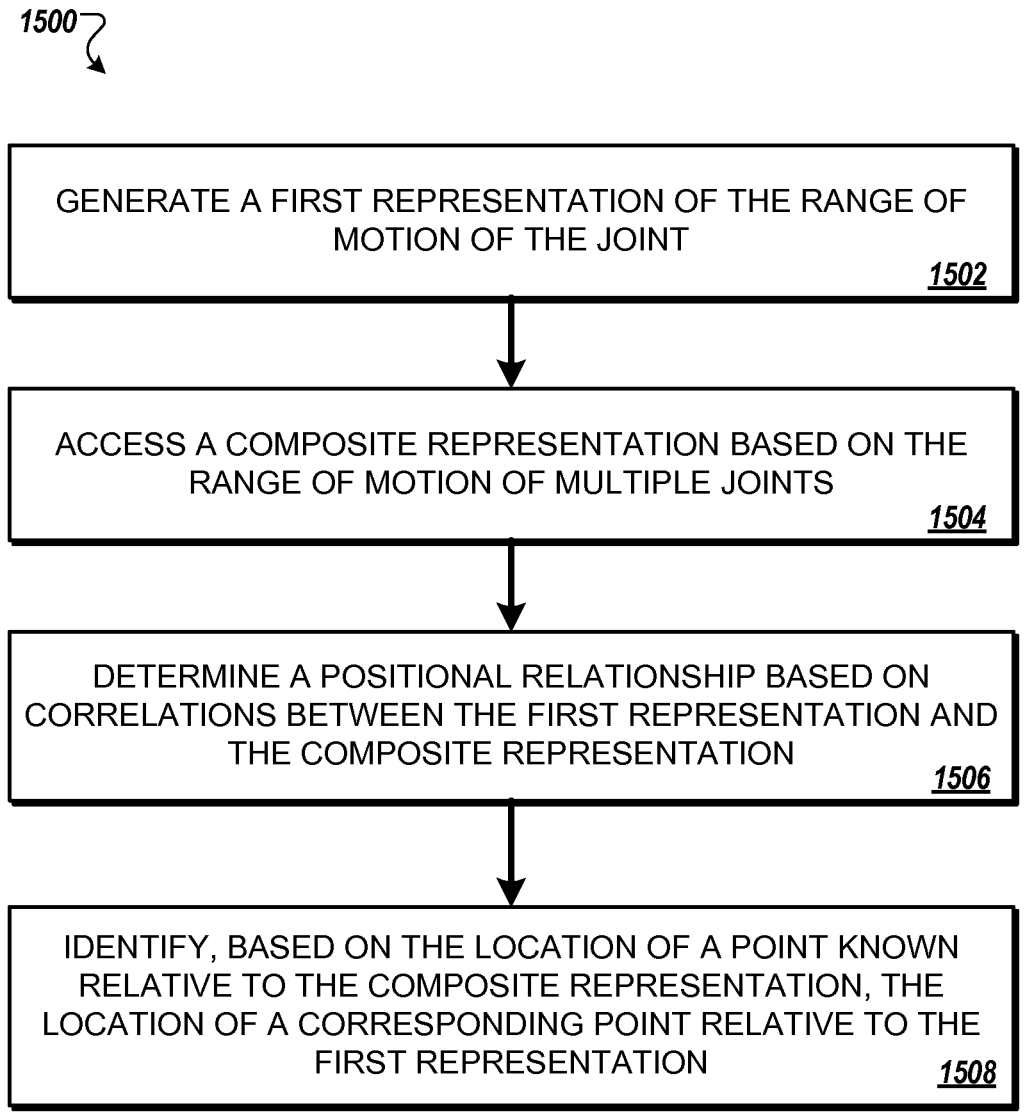

Referring to FIG. 38, in the process 1400, determining a second point (1406) can include the features of the process 1500.

A first representation of the range of motion of the joint is generated (1500). For example, the information indicating the range of motion of the joint can include a multiple locations or points, and generating a representation can include data fitting a surface to the locations or points. A composite representation based on the range of motion of multiple joints is accessed (1504). A positional relationship based on correlations between the first representation and the composite representation is determined (1506). For example, a positional relationship between the first representation and the composite representation can be determined based on commonalities among corresponding features. The commonalities can be used to align the first representation relative to the composite representation. Based on the location of a point known relative to the composite representation, the location of a corresponding point is identified relative to the first representation (1508). For example, a point on the first representation can be identified that corresponds to an intersection point of an axis with the composite representation. The second point used to define the impaction axis can be the point identified relative to the first representation.

Figure 39:
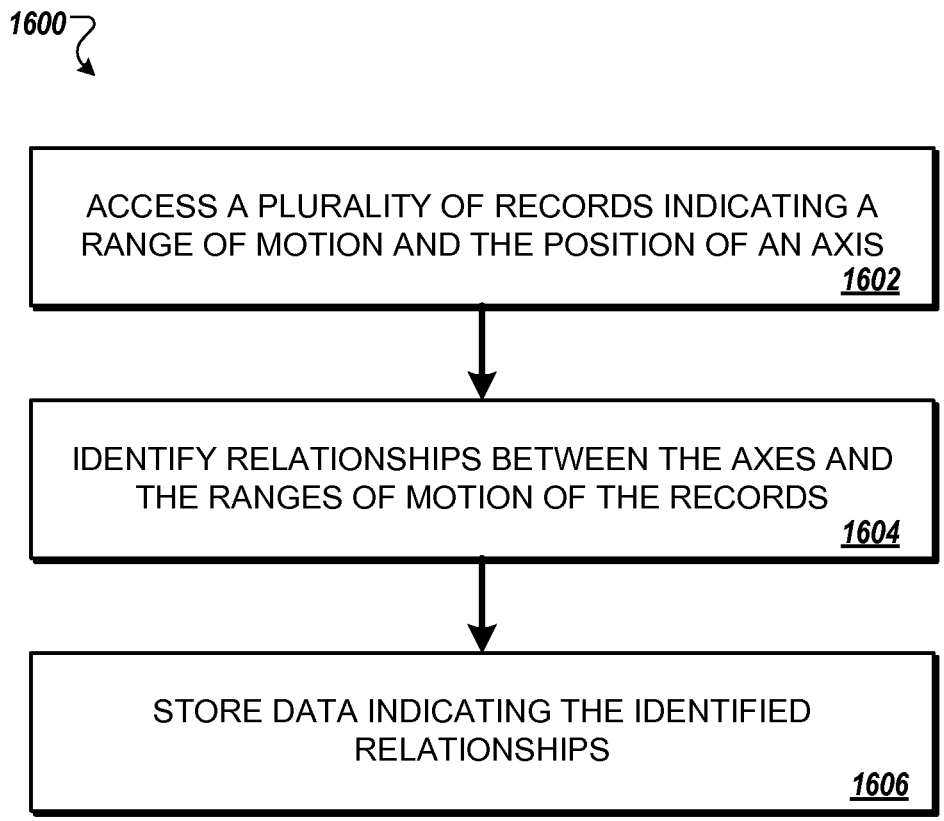
FIG. 39 is a flow diagram illustrating an example process for processing data describing multiple joints.

Referring to FIG. 39, a process 1600 can be performed, for example, by one of the control units 50, 550 or another computer system, to analyze joint data. The process 1600 can also include additional features described above, for example, features described with reference to FIGS. 12A, 12B, and 13.

A plurality of records indicating a range of motion and the position of an axis are accessed (1602). The records can be accessed from a data storage device, or can be created based on received information. The position of the axis indicated in each record can be a position determined using tomography data for the corresponding joint.

Relationships between the axes and the ranges of motion of the records are identified (1604). The relationships can include positional relationships determined based on correlations among corresponding features. Data indicating the identified relationships are stored (1606). Examples of relationships include, correlations between the ranges of motion indicated in different records, relationships between the position of an axis indicated in one record and the position of an axis indicated in another record, and relationships between the position of an axis in one of the records and the range of motion of a different one of the records (see FIGS. 12A to 12C and 13 and corresponding description). Relationships can also include, for each of the records, relationships between the position of the axis and features of the range of motion of the joint, such as boundaries of the range of motion.

The process 1600 can include providing access to the stored relationships. The process 1600 can include generating and storing a composite representation 320 of a range of motion and a composite axis 329 using the identified relationships. The process 800 can include determining, based on the identified relationships, a tolerance about the composite axis 329, for example, the radius of one or more of the regions 330, 331, 332 in FIG. 12C. The tolerance can indicate that a particular number of records, percentage of records, or range of percentages (e.g., the range "90% or more"), when correlated with the composite range of motion based on corresponding features, have a corresponding axis within the tolerance.

Figure 40:
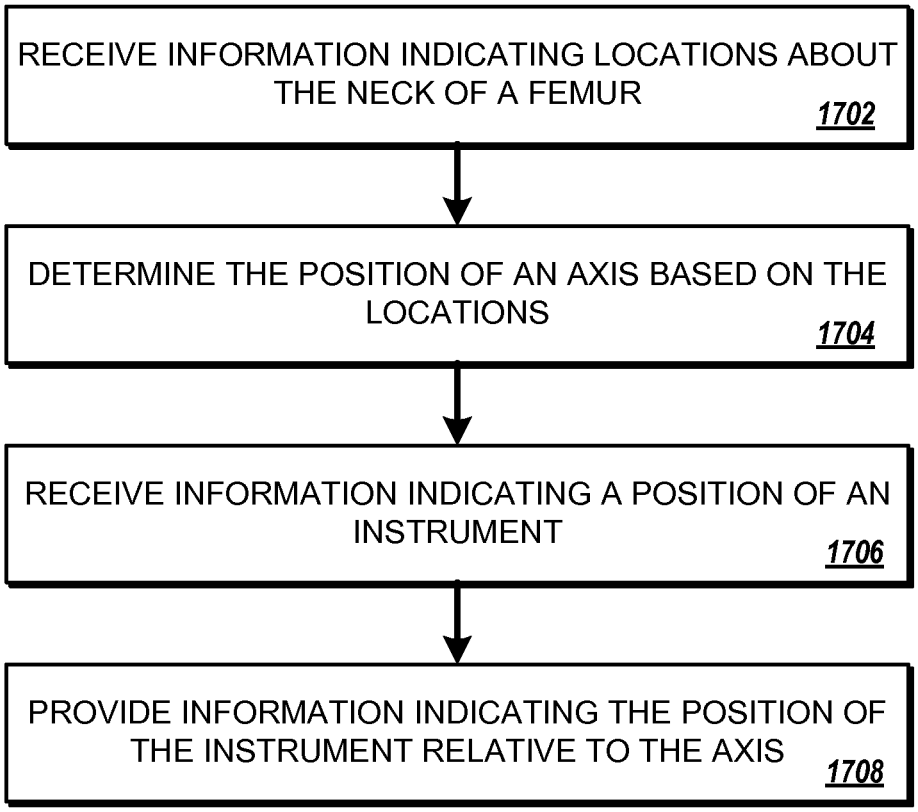

Referring to FIG. 40, a process 1700 can be performed, for example, by one of the control units 50, 550, to indicate a position of an instrument relative to a bone of a joint. The process 1700 can also include additional features described above, for example, features described with reference to FIGS. 17 to 20.

Information indicating a plurality of locations about the neck of a femur is received (1702). The received information can indicate locations relative to a reference located at a known position relative to the femur. The reference can be coupled to the femur.

The position of an axis is determined based on the plurality of locations (1704). For example, a cylinder can be extrapolated from the plurality of locations, and the axis can be a central axis of the cylinder. The cylinder can be determined relative to the reference, and thus the position of the axis can be determined relative to the reference.

Information indicating a position of an instrument is received (1706). The information can indicate the position of the instrument relative to the same reference relative to which the plurality of locations is indicated.

Information indicating the position of the instrument relative to the axis is provided (1708), for example, on a user interface. For example, a three-dimensional view of the femur can be displayed, with indications of the position of the axis and the position of the instrument.

Figure 41:
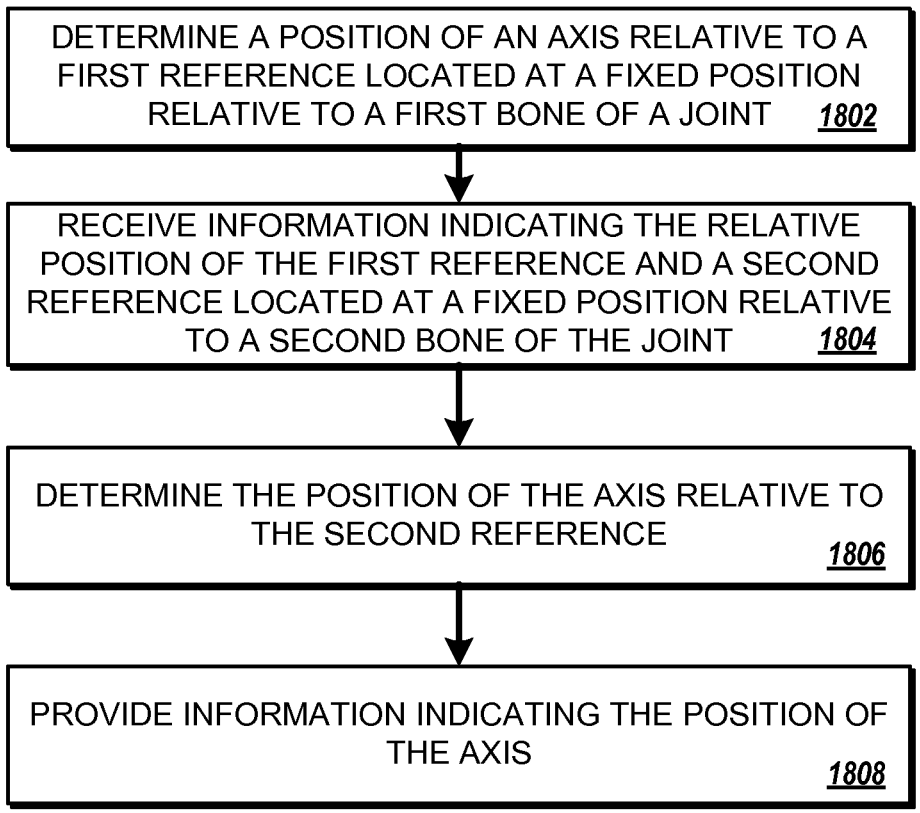

Referring to FIG. 41, a process 1800 can be performed, for example, by one of the control units 50, 550, to determine an alignment relative to a joint. The process 1800 can also include additional features described above, for example, features described with reference to FIGS. 21A and 21B.

A position of an axis is determined relative to a first reference, the first reference being located at a fixed position relative to a first bone of a joint (1802). Information indicating a relative position of the first reference and a second reference is received (1804). The second reference is located at a fixed position relative to a second bone of the joint. The position of the first reference relative to the second reference corresponds to a known position of the first bone relative to the second bone. For example, the first bone can be a femur, the second bone can be a pelvis, and the known position can be a neutral alignment of the femur relative to the pelvis. As another example, the first bone can be a humerus, the second bone can be a scapula, and the known position can be a neutral position of the humerus relative to the scapula.

The position of the axis is determined relative to the second reference (1806). The position of the axis is determined relative to the second reference based on (i) the relative position of the first reference and the second reference, and (ii) the position of the axis relative to the first reference. For example, an offset can be determined between the position of the second reference and the position of the axis when the first bone is in the known position relative to the second bone. Information indicating the position of the axis is provided (1808). For example, after dislocating the joint, information indicating the position of the axis relative to the second bone can be provided.

Figure 42:
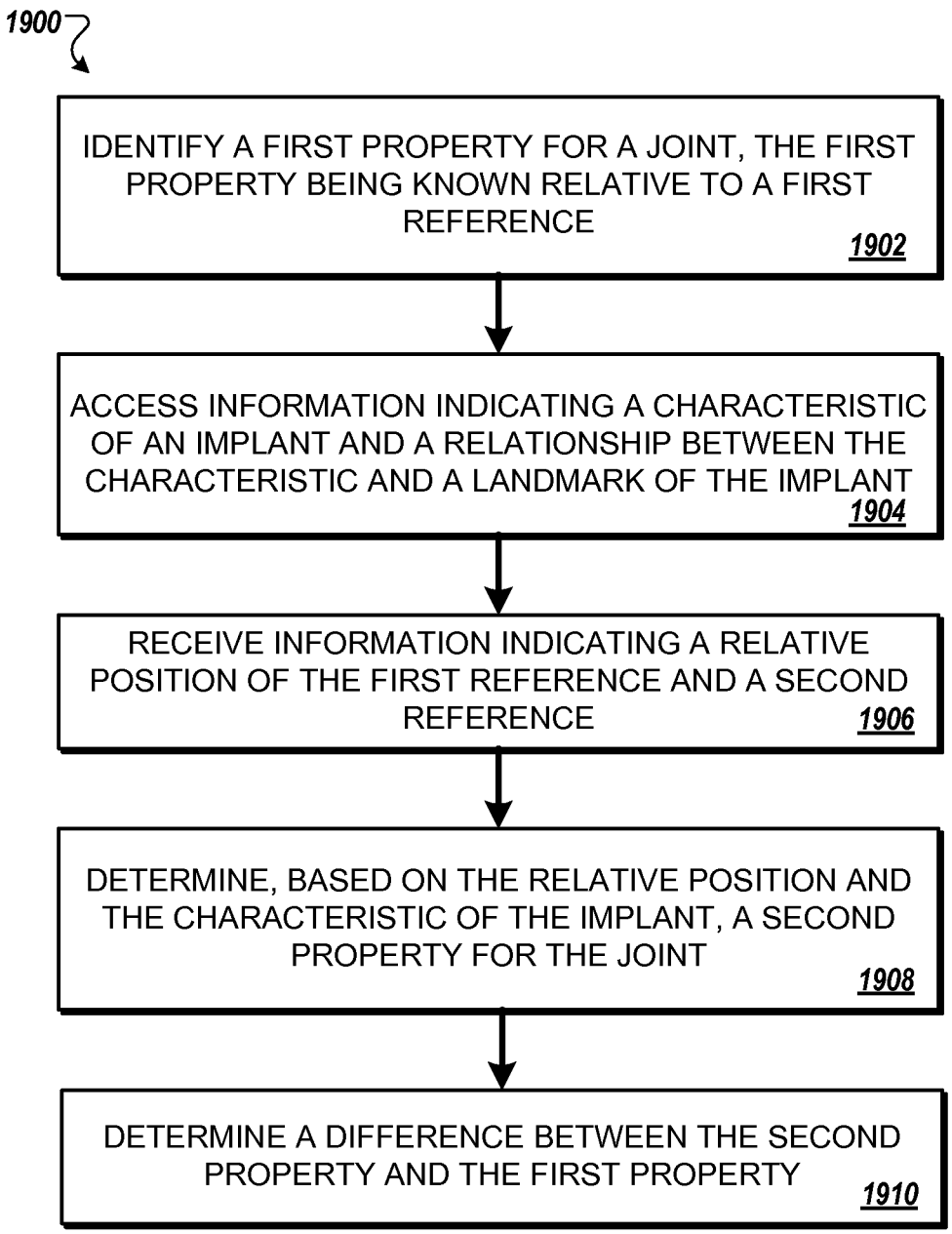

Referring to FIG. 42, a process 1900 can be performed, for example, by one of the control units 50, 550, to determine the suitability of an implant. The process 1900 can also include additional features described above, for example, features described with reference to FIGS. 22A, 22B, and 23.

A first property for a joint is identified (1902). The first property is known relative to a first reference located at a fixed position relative to a bone. Information is accessed indicating (i) a characteristic of an implant and (ii) a relationship between the characteristic and a landmark of the implant (1904). The characteristic of the implant can be, for example, one of a neck angle, a location corresponding to a joint center of rotation, a neck length, a dimension of the implant, or a position of an axis defined by the implant, and the known relationship relative to the landmark is a known position relative to the landmark. Information indicating a relative position of the first reference and a second reference is received (1906). The second reference is located a known position relative to the landmark, for example, at the landmark. A second property for the joint is determined based on the relative position and the characteristic of the implant (1908). The second property can be defined by the implant. A difference between the second property and the first property is determined (1910).

The process 1900 can also include providing information indicating the difference between the second property and the first property. The process 1900 can also include identifying a second implant calculated to define a third property for the joint such that a difference between the third property and the first property is less than the difference between the second property and the first property, and providing information identifying the second implant. Identifying the second implant can include identifying a desired characteristic based on the difference between the first property and the second property and the characteristic. For example, when the first property and the second property are neck lengths, and the difference between them indicates that neck length of the first implant is too short, the desired characteristic can be determined by adding the difference to the neck length of the first implant. Identifying the second implant can further include accessing data indicating characteristics of multiple implants, comparing the desired characteristic with one or more characteristics indicated by the accessed data, and selecting one or more implants or combinations of implants having a characteristic substantially equal to the desired characteristic.

Identifying a second implant can include identifying a model number or part number for the second implant. The first property and the second property can each be an angle of a neck, a length of a neck, a location of a joint center of rotation, or a position of an axis of a neck. For example, the first property can be the location of a natural center of rotation of the joint, and the second property can be a location of center of rotation of the joint defined by the implant when coupled to the bone.

As another example, the first property can be a neck angle of a natural femur, such as an angle between an axis through the neck of the femur and the longitudinal axis of the femur. The second property can be a neck angle defined by the implant, such as an angle of an axis through the neck of the implant and the longitudinal axis of the femur when the implant is coupled to the bone.

In some implementations, the bone is a femur, the first property is a position of an axis defined by a neck of the femur, the characteristic of the implant is the position of an axis defined by a neck of the implant, and the second property is the position of an axis defined by the neck of the implant when the implant is coupled to the femur.

Figure 43:
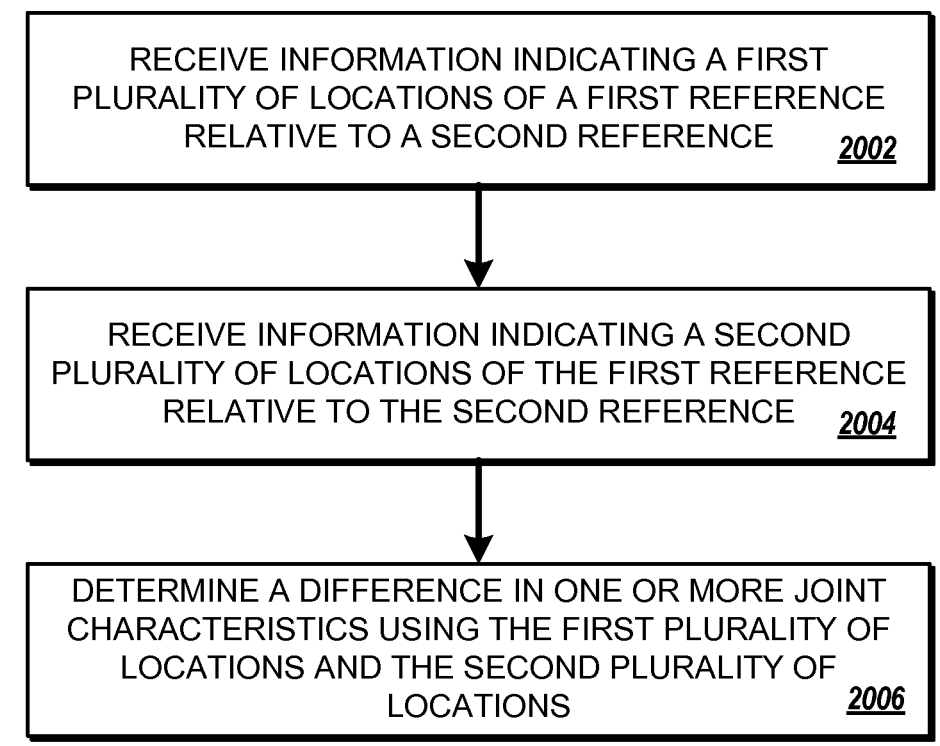

Referring to FIG. 43, a process 2000 can be performed, for example, by one of the control units 50, 550, to determine differences in joint characteristics. The process 2000 can include additional features described above, for example, features described with reference to FIGS. 24A and 24B.

Information indicating a first plurality of locations of a first reference relative to a second reference is received (2002). Information indicating a second plurality of locations of the first reference relative to the second reference (2004). The first plurality of locations and the second plurality of locations can be measured at different positions of a joint before and after a surgical procedure, respectively. The first plurality of locations and the second plurality of locations can be measured with the first reference located a known position relative to a bone of a joint, the second reference located a different known position relative to a different bone of the joint, such that movement of the joint A difference in one or more joint characteristics is determined using the first plurality of locations and the second plurality of locations (2006). A first three-dimensional surface can be extrapolated from the first plurality of locations to represent the range of motion at a first point in time. A second three-dimensional surface can be extrapolated from the second plurality of locations to represent the range of motion at a second point in time. The first surface and the second surface can be compared. The first surface and the second surface can be spheres, and the radii of the spheres can be compared to determine a difference in leg length. Points corresponding to the centers of the spheres can be compared to determine a change in the center of rotation of the joint. Changes in the center of rotation of the joint, differences in leg length, and other characteristics can be determined.

Based on the first plurality of locations and the second plurality of locations, for example, using identified differences between the first surface and the second surface, adjustments to the joint are calculated to cause the range of motion indicated by the first plurality of locations to have a particular relationship with the range of motion indicated by the second plurality of locations. For example, the particular relationship can be that the ranges of motion are equal in size, shape, and location, or have a particular offset from each other.

Figure 44:
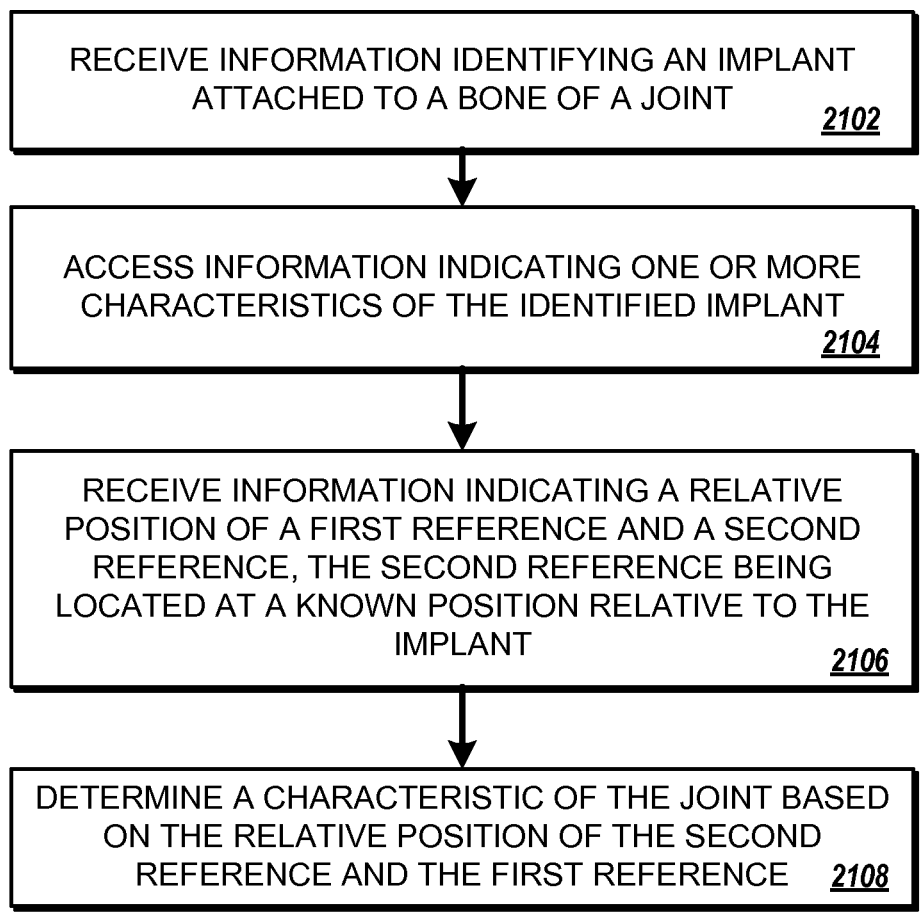

Referring to FIG. 44, a process 2100 can be performed, for example, by one of the control units 50, 550, to determine an alignment for a revision surgery. The process 2200 can include additional features described above, for example, features described with reference to FIGS. 25A, 25B, 26A, and 26B.

Information identifying an implant is received, the implant being attached to a bone of a joint (2102). Information indicating one or more characteristics of the identified implant is accessed (2104). Information indicating a relative position of a first reference and a second reference is received (2106). The first reference is located at a fixed position relative to the bone. The second reference is located at a known position relative to the implant, such as a landmark. A characteristic of the joint is determined based on the relative position of the second reference and the first reference (2108). The determination of characteristic can also be determined based on the known position of the second reference relative to the implant and the one or more characteristics of the implant. The characteristic of the joint can be, for example, the center of rotation of the joint. The characteristic of the joint can also be an axis defined by an implant or an axis along which an implant is installed.

In the systems 100, 500 described above, the control units 50, 550 can each include one or more storage devices, for example, a non-transitory computer readable medium, that store instructions that can be executed or interpreted. When executed by one or more processing devices of the control unit, the instructions cause the control unit to perform the operations described above.

Various implementations can include corresponding systems, apparatus, and computer programs, configured to perform the actions of the processes described in this document, encoded on computer storage devices. A system of one or more processing devices or one or more computers or can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

Implementations of the subject matter and the functional operations described in this specification, can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, an operating system, or a combination of one or more of them.

A number of implementations and alternatives have been described. Nevertheless, it will be understood that various modifications may be made without departing from the spirit and scope of the disclosure. For example, although some of the implementations above have been described with respect to surgical procedures for the hip joint, the above-described implementations may be employed for targeting other joints and operation sites of body, such as, for example, the shoulder joint. Additionally, the implementations described above may be employed for procedures other than arthroplasty. Accordingly, other implementations are within the scope of the following claims.

The invention claimed is:

1. A system, comprising:
   a guide having an outer contour adapted to substantially conform to a receiving portion of a joint, wherein the outer contour that is adapted to substantially conform to the receiving portion of the joint is formed prior to use of the guide, and the guide is adapted to mate with the receiving portion of the joint in a single orientation;
   a first reference device for attachment to a bone of the joint;
   a second reference device for coupling at a known alignment relative to the guide; and
   a control unit configured to communicate with the first reference device and the second reference device, the control unit being configured to determine the position of the axis relative to the first reference device based on data that indicates a position of the second reference device relative to the first reference device when the second reference device is in the known alignment relative to the guide and the guide is mated to the joint.

2. The system of claim 1, wherein the joint is a hip joint of a particular patient;
   and wherein the guide is a patient-specific guide having the outer contour defined for the hip joint of the particular patient, the outer contour being adapted to substantially conform to one or more portions of an acetabulum of the hip joint such that the guide mates with the acetabulum in a single orientation.

3. The system of claim 2, wherein a portion of the guide is adapted to conform to other features of a pelvis of the particular patient.

4. The system of claim 3, wherein the portion of the guide is adapted to conform to at least one of an acetabulum rim of the pelvis, a greater sciatic notch of the pelvis, a portion of an ilium of the pelvis, or the anterior inferior iliac spine of the pelvis.

5. The system of claim 1, wherein the outer contour of the guide that is adapted to substantially conform to the receiving portion of the joint has been formed by three-dimensional printing.

6. The system of claim 1, wherein the guide has been molded, cut, or machined to include the outer contour of the guide that is adapted to substantially conform to the receiving portion of the joint.

7. The system of claim 1, further comprising an electromagnetic field generator;
wherein the first reference device comprises a first electromagnetic field sensor, and the second reference device comprises the electromagnetic field generator or a second electromagnetic field sensor.

8. The system of claim 1, wherein the control unit is further configured to:
determine a position of an instrument relative to a center of rotation of the joint or a surface of the joint based on the information indicating a position of the instrument relative to the first reference;
calculate a reaming depth along the axis relative to the position of the instrument; and
provide information indicating the reaming depth.

9. The system of claim 8, wherein:
to calculate the reaming depth, the control unit is configured to:
access information indicating one or more characteristics of an implant;
determine a preferred reaming depth based on the one or more characteristics of the implant; and
determine a difference between a current position of the instrument and a preferred position for the instrument, the preferred position corresponding to the preferred reaming depth; and
to provide information indicating the reaming depth, the control unit is configured to provide information indicating the difference between the current position of the instrument and the preferred position of the instrument.

10. A system, comprising:
a guide having an outer contour adapted to substantially conform to a receiving portion of a joint, the guide defining an axis that has a known position relative to the joint when the guide is mated to the joint, wherein the outer contour that is adapted to substantially conform to the receiving portion of the joint is formed prior to use of the guide, and the guide is adapted to mate with the receiving portion of the joint in a single orientation;
a first reference device for attachment to a bone of the joint;
a second reference device for coupling at a known alignment relative to the guide; and
a control unit configured to communicate with the first reference device and the second reference device, the control unit being configured to determine the position of the axis relative to the first reference device based on data that indicates a position of the second reference device relative to the first reference device when the second reference device is in the known alignment relative to the guide and the guide is mated to the joint.

11. The system of claim 10, wherein the axis has a known inclination angle and a known anteversion angle relative to the joint when the guide is coupled to the joint.

12. The system of claim 10, wherein the second reference device is configured to be attached to the guide at a position having a known offset relative to the axis.

13. The system of claim 10, wherein:
the joint is a hip joint of a particular patient;
the axis is an acetabular impaction axis for the hip joint determined based on imaging data for the hip joint; and
the guide is a patient-specific guide having the outer contour defined for the particular patient, the outer contour being adapted to substantially conform to one or more portions of an acetabulum of the hip joint such that the guide mates with the acetabulum in a single orientation.

14. The system of claim 10, further comprising an electromagnetic field generator;
wherein the first reference device comprises a first electromagnetic field sensor, and the second reference device comprises the electromagnetic field generator or a second electromagnetic field sensor.

15. The system of claim 10, further comprising an infrared detector;
wherein the first reference device comprises a first fiducial, and the second reference device comprises a second fiducial.

16. The system of claim 10, wherein, to determine the position of the axis relative to the first reference device, the control unit is configured to determine the position of the axis in a reference frame, the first reference having a fixed position in the reference frame.

17. The system of claim 10, wherein the control unit is configured to:
determine a position of an instrument relative to the axis while the second reference device or a third reference device is coupled to the instrument; and
output, on a user interface, data indicating the position of the instrument relative to the axis.

18. The system of claim 10, wherein the control unit is further configured to:
determine a position of an instrument relative to a center of rotation of the joint or a surface of the joint based on the information indicating a position of the instrument relative to the first reference;
calculate a reaming depth along the axis relative to the position of the instrument; and
provide information indicating the reaming depth.

19. The system of claim 18, wherein:
to calculate the reaming depth, the control unit is configured to:
access information indicating one or more characteristics of an implant;
determine a preferred reaming depth based on the one or more characteristics of the implant; and
determine a difference between a current position of the instrument and a preferred position for the instrument, the preferred position corresponding to the preferred reaming depth; and
to provide information indicating the reaming depth, the control unit is configured to provide information indicating the difference between the current position of the instrument and the preferred position of the instrument.

* * * * *